United States Patent
Hellerstein

(10) Patent No.: US 8,084,016 B2
(45) Date of Patent: *Dec. 27, 2011

(54) MEASUREMENT OF BIOSYNTHESIS AND BREAKDOWN RATES OF BIOLOGICAL MOLECULES THAT ARE INACCESSIBLE OR NOT EASILY ACCESSIBLE TO DIRECT SAMPLING, NON-INVASIVELY, BY LABEL INCORPORATION INTO METABOLIC DERIVATIVES AND CATABOLITIC PRODUCTS

(75) Inventor: Marc K. Hellerstein, Kensington, CA (US)

(73) Assignee: The Regents of the University of California, Oakland, CA (US)

( * ) Notice: Subject to any disclaimer, the term of this patent is extended or adjusted under 35 U.S.C. 154(b) by 698 days.

This patent is subject to a terminal disclaimer.

(21) Appl. No.: 12/173,784

(22) Filed: Jul. 15, 2008

(65) Prior Publication Data
US 2009/0041661 A1    Feb. 12, 2009

Related U.S. Application Data

(63) Continuation of application No. 10/366,125, filed on Feb. 12, 2003, now Pat. No. 7,449,171.

(60) Provisional application No. 60/356,008, filed on Feb. 12, 2002.

(51) Int. Cl.
*C12Q 1/00*    (2006.01)
*A61K 49/00*    (2006.01)
*A61K 33/00*    (2006.01)

(52) U.S. Cl. ............. 424/9.1; 424/600; 435/4; 436/174; 436/173

(58) Field of Classification Search .................... None
See application file for complete search history.

(56) References Cited

U.S. PATENT DOCUMENTS

| | | | |
|---|---|---|---|
| 4,065,552 | A | 12/1977 | Costa |
| 4,332,784 | A | 6/1982 | Smith et al. |
| 4,889,126 | A | 12/1989 | Doddrell et al. |
| 4,940,658 | A | 7/1990 | Allen et al. |
| 5,026,909 | A | 6/1991 | Zolotarev et al. |
| 5,042,488 | A | 8/1991 | Ackerman |
| 5,167,948 | A | 12/1992 | Wenzel et al. |
| 5,209,919 | A | 5/1993 | Turteltaub et al. |
| 5,317,098 | A | 5/1994 | Shizuya et al. |
| 5,338,686 | A | 8/1994 | Hellerstein |
| 5,354,662 | A | 10/1994 | Stone et al. |
| 5,376,355 | A | 12/1994 | Turteltaub et al. |

(Continued)

FOREIGN PATENT DOCUMENTS

EP    0826377    3/1998

(Continued)

OTHER PUBLICATIONS

"NCBI Blast: Protein Sequence (17 letters)," located at <http://blast.ncbi.nlm.nih.gov/Blast.cgi> visited on May 29, 2008, 5 pages.

(Continued)

*Primary Examiner* — Allison Ford
(74) *Attorney, Agent, or Firm* — Morrison & Foerster LLP

(57) ABSTRACT

Methods of determining rate of biosynthesis or breakdown of biological molecules from metabolic derivatives and catabolic products are disclosed herein. In particular, methods of measuring the rates of biosynthesis and breakdown of biological molecules inaccessible or not easily accessible to direct sampling by sampling metabolic derivatives and catabolic products in accessible biological samples are disclosed herein.

39 Claims, 13 Drawing Sheets

U.S. PATENT DOCUMENTS

| | | | |
|---|---|---|---|
| 5,394,236 A | 2/1995 | Murnick |
| 5,432,058 A | 7/1995 | Lange, III et al. |
| 5,439,803 A | 8/1995 | Ross et al. |
| 5,506,147 A | 4/1996 | Kolhouse et al. |
| 5,597,548 A | 1/1997 | Sherry et al. |
| 5,665,377 A | 9/1997 | Gonella et al. |
| 5,665,562 A | 9/1997 | Cook |
| 5,783,445 A | 7/1998 | Murnick |
| 5,855,921 A | 1/1999 | Somlyai et al. |
| 5,910,403 A | 6/1999 | Hellerstein |
| 5,916,537 A | 6/1999 | Kajiwara et al. |
| 5,922,554 A | 7/1999 | Fielding et al. |
| 5,924,995 A | 7/1999 | Klein et al. |
| 5,961,470 A | 10/1999 | Wagner et al. |
| 6,010,846 A | 1/2000 | Hellerstein |
| 6,031,228 A | 2/2000 | Abramson |
| 6,071,245 A | 6/2000 | Kohno et al. |
| 6,117,656 A | 9/2000 | Seed |
| 6,284,219 B1 | 9/2001 | Ajami et al. |
| 6,329,208 B1 | 12/2001 | Jones et al. |
| 6,355,416 B1 | 3/2002 | Abramson |
| 6,461,806 B1 | 10/2002 | Hellerstein |
| 6,461,870 B2 | 10/2002 | Yatscoff et al. |
| 6,468,802 B1 | 10/2002 | Yatscoff et al. |
| 6,599,750 B2 | 7/2003 | Yatscoff et al. |
| 6,602,715 B2 | 8/2003 | Yatscoff et al. |
| 6,610,270 B1 | 8/2003 | Ajami |
| 6,625,547 B1 | 9/2003 | Korzekwa et al. |
| 6,642,059 B2 | 11/2003 | Chait et al. |
| 6,653,076 B1 | 11/2003 | Franza, Jr. et al. |
| 6,653,090 B1 | 11/2003 | Lopaschuk |
| 6,670,194 B1 | 12/2003 | Aebersold et al. |
| 6,680,203 B2 | 1/2004 | Dasseux et al. |
| 6,764,817 B1 | 7/2004 | Schneider |
| 6,783,751 B2 | 8/2004 | Heumann |
| 6,808,875 B2 | 10/2004 | Hellerstein |
| 6,835,927 B2 | 12/2004 | Becker et al. |
| 6,849,396 B2 | 2/2005 | Schneider |
| 6,872,575 B2 | 3/2005 | Regnier |
| 6,887,712 B1 | 5/2005 | Medford et al. |
| 6,902,719 B2 | 6/2005 | Wagner |
| 6,906,320 B2 | 6/2005 | Sachs et al. |
| 7,001,587 B2 | 2/2006 | Hellerstein |
| 7,022,834 B2 | 4/2006 | Hellerstein |
| 7,048,907 B2 | 5/2006 | Groman et al. |
| 7,057,168 B2 | 6/2006 | Miller et al. |
| 7,084,396 B2 | 8/2006 | Schneider |
| 7,255,850 B2 | 8/2007 | Hellerstein |
| 7,256,047 B2 | 8/2007 | Malloy et al. |
| 7,262,020 B2 | 8/2007 | Hellerstein |
| 7,307,059 B2 | 12/2007 | Hellerstein |
| 7,357,913 B2 | 4/2008 | Hellerstein |
| 7,410,633 B2 | 8/2008 | Hellerstein |
| 7,449,171 B2 | 11/2008 | Hellerstein |
| 7,504,233 B2 | 3/2009 | Hellerstein |
| 2003/0068634 A1 | 4/2003 | Hellerstein |
| 2003/0119069 A1 | 6/2003 | Schneider et al. |
| 2003/0133871 A1 | 7/2003 | Hellerstein |
| 2003/0148533 A1 | 8/2003 | Malloy et al. |
| 2003/0180710 A1 | 9/2003 | Lee et al. |
| 2003/0180800 A1 | 9/2003 | Lee et al. |
| 2003/0211036 A1 | 11/2003 | Degani et al. |
| 2003/0224420 A1 | 12/2003 | Hellerstein et al. |
| 2003/0228259 A1 | 12/2003 | Hellerstein |
| 2004/0081994 A1 | 4/2004 | Hellerstein |
| 2004/0115131 A1 | 6/2004 | Hellerstein |
| 2004/0121305 A1 | 6/2004 | Wiegand et al. |
| 2004/0152994 A1 | 8/2004 | Meier-Augenstein |
| 2004/0191916 A1 | 9/2004 | Gross et al. |
| 2004/0253647 A1 | 12/2004 | Mathews et al. |
| 2005/0003375 A1 | 1/2005 | Franza et al. |
| 2005/0014181 A1 | 1/2005 | Galis et al. |
| 2005/0092910 A1 | 5/2005 | Geromanos et al. |
| 2005/0118724 A1 | 6/2005 | Bateman et al. |
| 2005/0153346 A1 | 7/2005 | Schneider |
| 2005/0175982 A1 | 8/2005 | Iwatani et al. |
| 2005/0201937 A1 | 9/2005 | Hellerstein |
| 2005/0202406 A1 | 9/2005 | Hellerstein |
| 2005/0221278 A1 | 10/2005 | Iwatani et al. |
| 2005/0238577 A1 | 10/2005 | Hellerstein |
| 2005/0238581 A1 | 10/2005 | Kurland et al. |
| 2005/0255509 A1 | 11/2005 | Hellerstein et al. |
| 2005/0281745 A1 | 12/2005 | Lee et al. |
| 2006/0008796 A1 | 1/2006 | Hellerstein |
| 2006/0020440 A1 | 1/2006 | Hellerstein |
| 2006/0094057 A1 | 5/2006 | Hellerstein |
| 2006/0100903 A1 | 5/2006 | Lee et al. |
| 2006/0105322 A1 | 5/2006 | Iwatani et al. |
| 2006/0105339 A1 | 5/2006 | Hellerstein |
| 2006/0120961 A1 | 6/2006 | Schneider et al. |
| 2006/0251576 A1 | 11/2006 | Hellerstein |
| 2006/0280682 A1 | 12/2006 | Hellerstein |
| 2007/0248540 A1 | 10/2007 | Hellerstein |
| 2008/0003179 A1 | 1/2008 | Hellerstein |
| 2009/0041661 A1 | 2/2009 | Hellerstein |

FOREIGN PATENT DOCUMENTS

| | | |
|---|---|---|
| JP | 2001-211782 A | 8/2001 |
| JP | 2003-79270 A | 3/2003 |
| SU | 968036 | 10/1982 |
| WO | WO-90/11371 | 10/1990 |
| WO | WO-93/20800 | 10/1993 |
| WO | WO-93/25705 | 12/1993 |
| WO | WO-95/13096 | 5/1995 |
| WO | WO-98/51820 | 11/1998 |
| WO | 00/12535 A2 | 3/2000 |
| WO | WO-00/13025 | 3/2000 |
| WO | WO-00/63683 | 10/2000 |
| WO | WO-01/80715 | 11/2001 |
| WO | WO-01/84143 | 11/2001 |
| WO | WO-03/061479 | 7/2003 |
| WO | WO-03/068919 | 8/2003 |
| WO | WO-03/087314 | 10/2003 |
| WO | WO-2004/003493 | 1/2004 |
| WO | 2004/016156 A2 | 2/2004 |
| WO | WO-2004/011426 | 2/2004 |
| WO | WO-2004/021863 | 3/2004 |
| WO | WO-2004/024941 | 3/2004 |
| WO | WO-2004/025270 | 3/2004 |
| WO | WO-2004/042360 | 5/2004 |
| WO | 20041016156 A3 | 6/2004 |
| WO | WO-2005/009597 | 2/2005 |
| WO | WO-2005/015155 | 2/2005 |
| WO | WO-2005/033652 | 4/2005 |
| WO | WO-2006/050130 | 5/2006 |
| WO | WO-2006/081521 | 8/2006 |
| WO | WO-2006/107814 | 10/2006 |

OTHER PUBLICATIONS

"New Diagnostic Technique Could Help Treat AIDS," *Agence France-Presse,* Dow Jones News/Retrieval, Feb. 17, 1998, pp. 1-2.

Ackermans, M. T. et al. (2001). "The Quantification of Gluconeogenesis in Healthy Men by 2H2O and [2-13C]Glycerol Yields Different Results: Rates of Gluconeogenesis in Healthy Men Measured with 2H2O are Higher than those Measured with [2-13C]Glycerol," *The Journal of Clinical Endocrinology & Metabolism* 86(5):2220-2226.

Adami, H. O. et al. (1995). "The Aetiology and Pathogenesis of Human Breast Cancer," *Mutation Research* 333:29-35.

Airhart, J. et al. (1974). "Compartmentation of Free Amino Acids for Protein Synthesis in Rat Liver," *The Biochemical Journal* 140:539-545.

Ajie, H. O. et al. (1995). "In Vivo Study of the Biosynthesis of Long-Chain Fatty Acids Using Deuterated Water," *The American Journal of Physiology* 269:E247-E252.

Anderson, R.W. et al. (1998). "Direct HIV Cytopathicity Cannot Account for CD4 Decline in AIDS in the Presence of Homeostasis: A Worst-Case Dynamic Analysis," *Journal of Acquired Immune Deficiency Syndromes and Human Retrovirology* 17:245-252.

Antelo, Fernando et al. (2002) "Adipose Triglyceride (TG) Turnover and De Novo Lipogenesis (DNL) in Humans: Measurement by Long-Term 2H2O Labeling and Mass Isotopomer Distribution Analysis (MIDA)" *Experimental Biology* 16 [Meeting Abstract 361.10]: A400.

Asher, E. et al. (1995). "Evaluation of Cell Death in EBV-Transformed Lymphocytes Using Agarose Gel Electrophoresis, Light Microscopy and Electron Microscopy. II. Induction of Non-Classic Apoptosis ("Para-Apoptosis") by Tritiated Thymidine," *Leukemia & Lymphoma* 19:107-119.

Attardi, G. et al. (1988). "Biogenesis of Mitochondria," *Annual Review of Cell Biology* 4:289-333.

Australian Patent Office Search Report mailed Aug. 26, 2005, for Singapore patent application No. SG 200500571-5, filed Jul. 25, 2003, 5 pages.

Austrian Search Report and Written Opinion mailed Aug. 5, 2009, for SG Application No. 200717391-7 filed May 3, 2006, 7 pages.

Bach, S. P. et al. (2000). "Stem Cells: The Intestinal Stem Cell as a Paradigm," *Carcinogenesis* 21(3):4469-476.

Backhouse, B. et al. (Mar. 1982). "Effects of haloperidol on cell proliferation in the early postnatal rat brain," *Neuropathology and Applied Neurobiology* 8(2):109-116.

Bandsma, R. H. et al. (1998). "Contribution of Newly Synthesized Cholesterol to Rat Plasma and Bile Determined by Mass Isotopomer Distribution Analysis: Bile-Salt Flux Promotes Secretion of Newly Synthesized Cholesterol into Bile," *The Biochemical Journal* 329:699-703.

Bandsma, R. H. et al. (2000) "The Contribution of Newly Synthesized Cholesterol to Bile Salt Synthesis in Rats Quantified by Mass Isotopomer Distribution Analysis," *Biochemica et Biophysica Acta* 1483:343-351.

Bertani, R. et al. (2002) "Measurement of Total Body Water (TBW) Through In Vivo Dilution of Tracer Compounds: Use of D2O and its Determination by FT Infrared Spectroscopy," *Annali Di Chimica* 92:135-138.

Bickenbach, J. R. (1981). "Identification and Behavior of Label-Retaining Cells in Oral Mucosa and Skin," *Journal of Dental Research* pp. 1611-1620.

Bier, D. M. (1997). "Stable Isotopes in Biosciences, their Measurement and Models for Amino Acid Metabolism," *European Journal of Pediatrics* 156:S2-S8.

Bier, D. M. (Nov. 1987). "The Use of Stable Isotopes in Metabolic Investigation," *Balliere's Clinical Endocrinology and Metabolism* 1(4):817-836.

Bingham, S.A. (1994). "The Use of 24-h Urine Samples and Energy Expenditure to Validate Dietary Assessments," *The American Journal of Clinical Nutrition* 59(suppl):227S-231S.

Black, G. E. et al. (2001). "Labeling DNA with Stable Isotopes: Economical and Practical Considerations," *Bio Techniques* 30:134-138, 140.

Blair, S. N. et al. (1995). "Changes in Physical Fitness and All-Cause Mortality. A Prospective Study of Healthy and Unhealthy Men," *JAMA* 273: 1093-1098.

Blau, K. and Halket, J. eds. (1993) *Handbook of Derivatives for Chromatography*, 2nd Edition, John Wiley & Sons Ltd., England.

Bonotto, S. et al. (1978). "Study of the Distribution and Biological Effects of 3H in the Algae Acetabularia, Chlamydomonas and Porphyra," *Current Topics in Radiation Research Quarterly* 12:115-132.

Boros, L. G. et al. (2001). "Genistein Inhibits Nonoxidative Ribose Synthesis in MIA Pancreatic Adenocarcinoma Cells: A New Mechanism of Controlling Tumor Growth," *Pancreas* 22(1):1-7.

Boros, L. G. et al. (Mar. 2002). "Metabolic Profiling of Cell Growth and Death in Cancer: Applications in Drug Discoverer," *Drug Discovery Today* 7(6):364-372.

Bravo, E. et al. (1994). "Decreased Hepatic Uptake and Processing of High Density Lipoprotein Unesterified Cholesterol and Cholesteryl Ester with Age in the Rat," *Journal of Biochemistry* 116:1088-1095.

Brown, A. S. et al. (1998). "Treating Patients with Documented Atherosclerosis to National Cholesterol Education Program-Recommended Low-Density-Lipoprotein Cholesterol Goals with Atorvastatin, Fluvastatin, Lovastatin and Simvastatin," *Journal of the American College of Cardiology* 32:665-672.

Bucy, R.P. et al. (1998) "Analysis of Lymph Node Biopsies in HIV Infected Patients Before and After Haart" Abstract, *5th Conference on Retroviruses and Opportunistic Infections*, Session 66 519:177.

Caldwell, K.A. et al. (1993) "Quantification of Peptide Isotopomer Abundances and Determination of Protein (sic) Turnover Rates by Using Mase Isotopomer Distribution Analysis" Abstract, *41st Annual Amer. Society Mass Spectrometry on Mass Spectrometry*, p. 331a.

Cassella, C.R. et al. (1997) "Mechanisms of Lymphocyte Killing by HIV," *Current Opinion in Hematology* 4:24-31.

Cesar, D. et al. (1998) "Direct Measurement of CD4+ and CD8+ T Cell Proliferation Rates in Vivo in AIDS Patients Using a Stable Isotope-Mass Spectrometric Technique" Abstract, *5th Conference on Retroviruses and Opportunistic Infections*, Chicago Illinois.

Chinkes, D. L. et al. (1996). "Comparison of Mass Isotopomer Dilution Methods Used to Compute VLDL Production In Vivo," *The American Journal of Physiology* 271:E373-E383.

Christiansen, M. P. et al. (Oct. 2000) "Effect of Dietary Energy Restriction on Glucose Production and Substrate Utilization in Type 2 Diabetes," *Diabetes* 49:1691-1699.

Clarke, R. B. (2005). "Isolation and Characterization of Human Mammary Stem Cells," *Cell Proliferation* 38:375-386.

Clayton, D. A. (1991). "Replication and Transcription of Vertebrate Mitochondrial DNA," *Annual Review of Cell Biology* 7:453-478.

Cohen, A. et al. (Oct. 25, 1983) "Purine and Pyrimidine Metabolism in Human T Lymphocytes. Regulation of Deoxyribonucleotide Metabolism," *The Journal of Biological Chemistry* 258(20):12334-12340.

Cohen, J. (1998) "Failure Isn't What It Used to Be . . . But Neither is Success," *Science* 279:1133-1134.

Collins, M. et al. (Mar. 15, 2000) "A Method for Measuring Mitochondrial Proliferation in Vivo Using 2H2O Incorporation Into Mitochondria DNA," *FASEB Journal* 14(4):A620.

Collins, M. L. et al. (2003). "Measurement of Mitochondrial DNA Synthesis In Vivo Using a Stable Isotope-Mass Spectrometric Technique," *Journal of Applied Physiology* 94:2203-2211.

Connors, M. et al. (1997). "HIV Infection Induces Changes in CD4+ T-Cell Phenotype and Depletions Within the CD4+ T-Cell Repertoire that are Not Immediately Restored by Antiviral or Immune-Based Therapies," *Nature Medicine* 3:533-540.

Conrads, Thomas P. et al. (Jan. 2002). "Stable Isotope Labeling in Proteomics" *The Synthesis Cambridge Isotope Laboratories* 3 (2):1-3.

Craig, S. B. et al. (1996). "The Impact of Physical Activity on Lipids, Lipoproteins, and Blood Pressure in Preadolescent Girls," *Pediatrics* 98:389-395.

Crain, P. F. (1990). "Preparation and Enzymatic Hydrolysis of DNA and RNA for Mass Spectrometry," *Methods in Enzymology* 193:782-790.

Dalvie, D. (2000). "Recent Advances in the Applications of Radioisotopes in Drug Metabolism, Toxicology and Pharmacokinetics," *Current Pharmaceutical Design* 6:1009-1028.

Davis, A. et al. (Jul. 2000). "Effect of Pinitol Treatment on Insulin Action in Subjects with Insulin Resistance," *Diabetes Care* 23(7):1000-1005.

Deeks, S. et al. (1998) "Viral Load and CD4+ T Cell Changes in Patients Failing Potent Protease Inhibitor Therapy" Abstract, *5th Conference on Retroviruses and Opportunistic Infections*, Session 53, 419:158.

Deeks, S. G. et al. (Feb. 1, 2002). "CD4+ T Cell Kinetics and Activation in Human Immunodeficiency Virus-Infected Patients who Remain Viremic Despite Long-Term Treatment with Protease Inhibitor-Based Therapy," *The Journal of Infectious Diseases* 185:315-323.

Dekker, E et al. (1997). "Glucose Homeostasis in Children with Falciparum Malaria: Precursor Supply Limits Gluconeogenesis and Glucose Production" *J Clin Endocrinol Metabol* 82: 2514-2521.

Di Buono, M. et al. (2000). "Comparison of Deuterium Incorporation and Mass Isotopomer Distribution Analysis for Measurement of Human Cholesterol Biosynthesis," *Journal of Lipid Research* 41:1516-1523.

Dimitrov, D.S. et al. (1995) "Scientific Correspondence," *Nature* 375:194-195.

Emken, E. A. (1994). "Metabolism of Dietary Stearic Acid Relative to Other Fatty Acids in Human Subjects," *The American Journal of Clinical Nutrition* 60(Suppl):1023S-1028S.

Emken, Edward A. et al. (1983) "Incorporation of deuterium-labeled trans= and cis-13-octadeconoic acids in human plasma lipids," *Journal of Lipid Research* 24: 34-41.

Etnier, E. L. et al. (1984). "Metabolism of Organically Bound Tritium in Man," *Radiation Research* 100:487-502.

Fagerquist, C. K. et al. (1999). "Molecular Ion Fragmentation and its Effects on Mass Isotopomer Abundances of Fatty Acid Methyl Esters Ionized by Electron Impact," 6*Journal of the American Society of Mass Spectrometry* 10:430-439.

Fagerquist, C. K. et al. (2001). "Elimination of the Concentration Dependence in Mass Isotopomer Abundance Mass Spectrometry of Methyl Palmitate Using Metastable Atom Bombardment," *Journal of the American Society of Mass Spectrometry* 12:754-761.

Futami, J. et al. (1999). "An Application of the On-line Respiratory Mass Spectrometer to the Detection of Helicobacter pylori Infection Using 13C-Labeled Urea," *Journal of the Mass Spectrometry Society of Japan* 47(6):386-388.

Gasparini, P. et al. (Mar. 1989). "Amplification of DNA from Epithelial Cells in Urine," *The New England Journal of Medicine* 320(12):809.

Gerling, B. et al. (1997). "Prediction of Liver Fibrosis According to Serum Collagen VI Level in Children with Cystic Fibrosis," *The New England Journal of Medicine* 336(22):1611:1612.

Gorochov, G. et al. (1998) "Perturbation of CD4+ and CD8+ T-Cell Repertoires During Progression to AIDS and Regulation of the CD4+ Repertoire During Antiviral Therapy," *Nature Medicine* 4:215-221.

Goz, B. (1977). "The Effects of Incorporation of 5-Halogenated Deoxyuridines into the DNA of Eukaryotic Cells," *Pharmacological Reviews* 29:249-272.

Gratzner, H.G. (1982). "Monoclonal Antibody to 5-Bromo- and 5-Iododeoxyuridine: A New Reagent for Detection of DNA Replication," *Science* 218:474-475.

Guo, Z. K. et al. (2000). "De Novo Lipogenesis in Adipose Tissue of Lean and Obese Women: Application of Deuterated Water and Isotope Ratio Mass Spectrometry," *International Journal of Obesity and Related Metabolic Disorders* 24:932-937.

Gygi, Steven et al. (2000) "Using Mass Spectrometry for Quantitative Proteomics" *Proteomics: A Trends Guide*: 31-36.

Hansen, A. P. et al. (1992). "A Practical Method for Uniform Isotopic Labeling of Recombinant Proteins in Mammalian Cells," *Biochemistry* 31:12713-12718.

Heck, S. D. et al. (Apr. 1996). "Posttranslational Amino Acid Epimerization: Enzyme-Catalyzed Isomerization of Amino Acid Residues in Peptide Chains," *Proceedings of the National Academy of Sciences of the United States of America* 93:4036-4039.

Hellerstein, M. et al. (1999) "Directly Measured Kinetics of Circulating T Lymphocytes in Normal and HIV-1-Infected Humans," *Nature Medicine* 5:83-89.

Hellerstein, M. K. (1995). "Methods for Measurement of Fatty Acid and Cholesterol Metabolism," *Current Opinion in Lipidology* 6:172-181.

Hellerstein, M. K. (1996). "Synthesis of Fat in Response to Alterations in Diet: Insights from New Stable Isotope Methodologies," *Lipids* 31(Supp):S117-5125.

Hellerstein, M. K. (1999). "Measurement of T-Cell Kinetics: Recent Methodologic Advances," *Trends Immunology Today* 20(10):438-441.

Hellerstein, M. K. (1999). "The Changing Face of AIDS: Translators Needed," *The American Journal of Clinical Nutrition* 70:787-788.

Hellerstein, M. K. (2001) "No Common Energy: de Novo Lipogenesis as the Road Less Traveled," *The American Journal of Clinical Nutrition* 74:707-708.

Hellerstein, M. K. (2002). "Carbohydrate-Induced Hypertriglyceridemia: Modifying Factors and Implications for Cardiovascular Risk," *Curr Opin Lipidol* 13:33-40.

Hellerstein, M. K. (2004). "New stable isotope-mass spectrometric techniques for measuring fluxes through intact metabolic pathways in mammalian systems: introduction of moving pictures into functional genomics and biochemical phenotyping," *Metabolic Engineering* 6:85-100.

Hellerstein, M. K. et al. (1986). "Glycoconjugates as Noninvasive Probes of Intrahepatic Metabolism: Pathways of Glucose Entry into Compartmentalized Hepatic UDP-glucose Pools during Glycogen Accumulation," *Proceedings of the National Academy of Sciences of the United States of America* 83(18):7044-7048.

Hellerstein, M. K. et al. (1992). "Mass Isotopomer Distribution Analysis: A Technique for Measuring Biosynthesis and Turnover of Polymers," *The American Journal of Physiology* 263:E988-E1001.

Hellerstein, M. K. et al. (1993). "Model for Measuring Absolute Rates of Hepatic de Novo Lipogenesis and Reesterification of Free Fatty Acids," *The American Journal of Physiology* 265:E814-E820.

Hellerstein, M. K. et al. (1994). "Effects of Cigarette Smoking and its Cessation on Lipid Metabolism and Energy Expenditure in Heavy Smokers," *J. Clin. Invest.* 93:265-272.

Hellerstein, M. K. et al. (1997). "Altered Fluxes Responsible for Reduced Hepatic Glucose Production and Gluconeogenesis by Exogenous Glucose in Rats," *The American Journal of Physiology* 272:E163-E172.

Hellerstein, M. K. et al. (1997). "Measurement of Hepatic Ra UDP-glucose in Vivo in Rats: Relation to Glycogen Deposition and Labeling Patterns," *The American Journal of Physiology* 272:E155-E162.

Hellerstein, M. K. et al. (1997). "T Cell Turnover in HIV-1 Disease," *Immunity* 7:583-589.

Hellerstein, M. K. et al. (1999). "Mass Isotopomer Distribution Analysis at Eight Years: Theoretical, Analytic, and Experimental Considerations," *The American Journal of Physiology* 276:E1146-E1170.

Hellerstein, M. K. et al. (2002) "Measurement of Synthesis Rates of Slow-turnover Proteins from 2H20 Incorporation into Non-essential Amino Acids (NEAA) and Application of Mass Isotopomer Distribution Analysis (MIDA)," *FASEB Journal Experimental Biology 2002: Meeting Abstracts* 16:A256.

Hellerstein, M. K. et al. (Sep. 1997). "Hepatic Gluconeogenic Fluxes and Glycogen Turnover During Fasting in Humans. A Stable Isotope Study," *The Journal of Clinical Investigation* 100(5):1305-1319.

Hellerstein, M.K. et al. (1994) "Mass Isotopomer Distribution Analysis for Measuring Fluxes Through Intracellular Metabolic Pathways and Biosynthetic Rates of Polymers" *IFAC Modeling and Control in Biomedical Systems*, pp. 353-359.

Hellerstein, Marc K. (2003) "In Vivo Measurement of Fluxes Through Metabolic Pathways: The Missing Link in Functional Genomics and Pharaceutical Research," *Annu. Rev. Nutr.* 23:379-402.

Ho, D. D. et al. (1995). "Rapid Turnover of Plasma Virions and CD4 Lymphocytes in HIV-1 Infection," *Nature* 373:123-126.

Hoh, R. et al. (1998). "De Novo Lipogenesis Predicts Short-Term Body-Composition Response by Bioelectrical Impedance Analysis to Oral Nutritional Supplements in HIV-Associated Wasting," *The American Journal of Physiology* 68:154-163.

Hsieh, E. A. et al. (2004). "Dynamics of Keratinocytes in Vivo Using 2H2O Labeling: A Sensitive Marker of Epidermal Proliferation State," *J Invest Dermatol* 123:530-536.

Hudgins, L. C. et al. (1996). "Human Fatty Acid Synthesis is Stimulated by a Eucaloric Low Fat, High Carbohydrate Diet," *J. Clin. Invest.* 97(9):2081-2091.

Hudgins, L. C. et al. (2000). "Relationship Between Carbohydrate-Induced Hypertriglyceridemia and Fatty Synthesis in Lean and Obese Subjects," *J. Lipid Res.* 41:595-604.

Hulzebos, C. V. et al. (2001). "Measurement of Parameters of Cholic Acid Kinetics in Plasma using a Microscale Stable Isotope Dilution Technique: Application to Rodents and Humans," *Journal of Lipid Research* 42:1923-1929.

Humphrey, T. J. et al. (1975). "A New Method for the Measurement of Protein Turnover," *Biochem. J.* 148:119-127.

Humphrey, T. J. et al. (1976) "A Sensitive Method for Measuring Protein Turnover Based on the Measurement of 2-3H-labeled Amino Acids in Proteins," *Biochem. J.* 156:561-568.

International Search Report and Written Opinion mailed Aug. 8, 2006, for international application No. PCT/US05/10429, filed Mar. 29, 2005, 16 pages.

International Search Report and Written Opinion mailed Feb. 5, 2008, for PCT Application No. PCT/US2006/017167 filed May 3, 2006, 11 pages.

International Search Report and Written Opinion mailed Oct. 11, 2007, for PCT Application No. PCT/US05/05660 filed 22, 2005, 11 pages.

International Search Report mailed Aug. 1, 2005, for PCT application No. PCT/US2005/08265, filed Mar. 11, 2005, 4 pages.

International Search Report mailed Aug. 18, 2004, for PCT application PCT/US03/23340, filed Jul. 25, 2003, 3 pages.
International Search Report mailed Jul. 8, 2004, for PCT patent application No. PCT/US03/27623 filed on Sep. 4, 2003, 3 pages.
International Search Report mailed on Apr. 13, 2004, for PCT application No. PCT/US03/20052 filed on Jun. 25, 2003, 2 pages.
International Search Report mailed on Apr. 4, 2005, for PCT application No. PCT//US04/21063 filed on Jun. 29, 2004, 2 pages.
International Search Report mailed on Aug. 18, 2004, for PCT application PCT/US03/29526 filed Sep. 16, 2003, 1 page.
International Search Report mailed on Aug. 20, 2004, for PCT application No. PCT/US03/10554 filed on Apr. 4, 2003, 4 pages.
International Search Report mailed on Jan. 19, 2005, for PCT application No. PCT/US03/29361 filed on Sep. 15, 2003, 3 pages.
International Search Report mailed on Jul. 9, 2004, for PCT application No. PCT/US03/35107 filed on Nov. 4, 2003, 2 pages.
International Search Report mailed on Jun. 29, 2004, for PCT application No. PCT/US03/04183 filed on Feb. 12, 2003, 4 pages.
International Search Report mailed on Mar. 25, 2005, for PCT application No. PCT/US04/39722 filed on Nov. 24, 2004, 2 pages.
Iyengar, V. et al. (1991). "Human Stools as a Source of Viable Colonic Epithelial Cells," *The FASEB Journal* 5:2856-2859.
James, J.S. (1998) "Clinical Implications of Virological Failure: Interview with Steven Deeks, M.D., San Francisco General Hospital," *AIDS Treatment News*, 289:6-7.
Jennings, G et al. (Jul. 1999) "The Use of Infrared Spectrophotometry for Measuring Body Water Spaces," *Clinical Chemistry* 45(7): 1077-1081.
Jones, J. G. (2001). "An Integrated 2H and 13C NMR Study of Gluconeogenesis and TCA Cycle Flux in Humans," *American Journal of Physiology-Endocrinology and Metabolism* 281:E848-856.
Jones, P. J. J. et al. (1990). "Evidence for Diurnal Periodicity in Human Cholesterol Synthesis," *Journal of Lipid Research* 31:667-673.
Jones, Peter J.H. et al. (1994). "Interaction of Dietary Fat Saturation and Cholesterol Level on Cholesterol Synthesis Measured Using Deuterium Incorporation," *Journal of Lipid Research* 35: 1093-1101.
Jung, Hye Rim. et al. (1999) "Metabolic Adaptations to Dietary Fat Malabsorption in Chylomicron-Deficient Mice," *Biochem. J.* 343: 473-478.
Jungas, Robert L. (1968) "Fatty Acid Synthesis in Adipose Tissue Incubated in Tritiated Water," *Biochemistry* 7(10): 3708-3717.
Katz, J. et al. (1976). "Futile Cycles in the Metabolism of Glucose," *Curr Top Cell Regul* 10: 237-89.
Kelleher, Joanne K. et al. (1992) "Model Equations for Condensation Biosynthesis Using Stable Isotopes and Radioisotopes," *Am. J. Physiol.* 262: E118-E125.
Khairallah, E. A. et al. (1976). "Assessment of Protein Turnover in Perfused Rat Liver: Evidence for Amino Acid Compartmentation from Differential Labeling of Free and tRNA-bound Valine," *J Biol Chem* 251(5): 1375-1384.
Kim, J. et al. (2000) "A New Stable Isotope-Mass Spectrometric (MS) Method to Measure Proliferation Rates of Colon Epithelial Cells," *FASEB Journal* 14(4): A718.
Lammert, Ole et al. (2000) "Effects of Isoenergetic Overfeeding of Either Carbohydrate or Fat in Young Men," *British Journal of Nutrition* 84:233-245.
Lee, Chong Do et al. (1999) "Cardiorespiratory Fitness, Body Composition, and All-Cause and Cardiovascular Disease Mortality in Men 1-3," *Am J Clin Nutr* 69:373-380.
Lefebvre, P. J. (Jan. 1979). "Naturally Labeled 13C-Glucose: A New Tool to Measure Oxidation Rates of Exogenous Glucose," *Diabetes* 28(Supp. 1): 63-65.
Leung, Gordon K. et al. (2000) "A Deficiency of Microsomal Triglyceride Transfer Protein Reduces Apolipoprotein B Secretion," *The Journal of Biological Chemistry* 275(11):7515-7520.
Lewanczuk, Richard Z. et al. (2004) "Comparison of the [13 C] Glucose Breath Test to the Hyperinsulinemic-Euglycemic Clamp When Determining Insulin Resistance," *Diabetes Care* 27(2):441-447.

Lipkin, M. (1987) "Proliferation and Differentiation of Normal and Diseased Gastrointestinal Cells," *In Physiology of the Gastrointestinal Tract*, L.R. Johnson ed., Raven Press, New York, pp. 255-284.
Lipkin, M. et al. (1963). "Cell Proliferation Kinetics in the Gastrointestinal Tract of Man. I. Cell Renewal in Colon and Rectum," *Journal of Clinical Investigations* 42(6):767-776.
Lutton, C. et al. (1990) "Critical analysis of the Use of 14C-acetate for Measuring In Vivo Rat Cholesterol Synthesis," *Reprod Nutr Dev* 30: 71-84.
MacAllan, Derek C. et al. (1998) "Measurement of Cell Proliferation by Labeling of DNA with Stable Isotope-Labeled Glucose: Studies in Vitro, in Animals, and in Humans," *Proc. Natl. Acad. Sci.* 95: 708-713.
Maentausta, O. et al. (1979). "Radioimmunoassay of Conjugated Cholic Acid, Chenodeoxycholic Acid, and Deoxycholic Acid from Human Serum, with Use of 125I-Labeled Ligands," *Clin. Chem.* 25(2): 264-268.
Malberg, J. et al. (Dec. 15, 2000). "Chronic antidepressant treatment increases neurogenesis in adult rat hippocampus," *J Neuroscience* 20(24):9104-9110.
Margolick, J.B. et al. (1995) "Failure of T-cell Homeostasis Preceding AIDS in HIV-1 Infection," *Nature Medicine* 1(7):674-680.
Maric, D. et al. (2000). "Functional Ionotropic Glutamate Receptors Emerge During Terminal Cell Division and Early Neuronal Differentiation of Rat Neuroepithelial Cells," *Journal of Neuroscience Research* 61(6):652-662.
Marin, S. et al. (2004). "Dynamic Profiling of the Glucose Metabolic Network in Fasted Rat Hepatocytes using [1,2-13C2]Glucose," *Biochemical Journal* 381:287-294.
Martin et al. (1998). "Discovery of a human liver glycogen phosphorylase inhibitor that lowers blood glucose in vivo," *Proc. Natl. Acad. Sci. USA* 95(4):1776-1781.
Mathur-De Vré, R. et al. (1984) "Molecular Aspects of Tritiated Water and Natural Water in Radiation Biology," *Prog. Biophys. Molec. Biol.* 43: 161-193.
McCloskey, J.A. (1990) "ElectronIonization Mass Spectra of Trimethylsilyl Derivatives of Nucleosides," *Meth. Enz.* 193:825-841.
McCune, J.M. (1997). "Thymic Function in HIV-1 Disease," *Seminars in Immunology* 9:397-404.
McCune, Joseph M. et al. (2000) "Factors Influencing T-Cell Turnover in HIV-1-Seropositive Patients," *J. Clin. Invest.* 105:R1-R8.
McLean, A.R. et al. (1995) "In Vivo Estimates of Division and Death Rates of Human T Lymphocytes," *Proc. Natl. Acad. Sci USA* 92:3707-3711.
Meier, P.R. et al. (Mar. 1981) "Rates of Protein Synthesis and Turnover in Fetal Life," *Am J Physiol.* 240(3):E320-E324.
Mellors, J.W. et al. (1995) "Quantitation of HIV-1 RNA in Plasma Predicts Outcome after Seroconversion," *Ann. Intern. Med.* 122:573-579.
Mellors, J.W. et al. (1996) "Prognosis in HIV-1 Infection Predicted by the Quantity of Virus in Plasma," *Science* 272:1167-70.
Messmer, Bradley T. et al. (Feb. 10, 2005) "In Vivo Measurements Document the Dynamic Cellular Kinetics of Chronic Lymphocytic Leukemia B Cells," *J. Clin. Invest.* doi:10.1172/JCI200523409.
Mewissen, D.J. et al. (1977). "Comparative Incorporation of Tritium from Tritiated Water Versus Tritiated Thymidine, Uridine or Leucine," *Curr Top Rad Res Quart* 12: 225-254.
Michie, C.A. et al. (1992) "Lifespan of Human Lymphocyte Subsets Defined by CD45 Isoforms," *Nature* 360:264-265.
Mikkola, T. S. et al. (2003). "Serum Cholesterol Efflux Potential is an Independent Predictor of Coronary Artery Atherosclerosis," *Atherosclerosis* 170:31-38.
Mindham, M. A. et al. (1994). "Application of Simultaneous Spleen and Liver Perfusion to the Study of Reverse Cholesterol Transport," *Biochemical Journal* 302:207:213.
Misell, L. et al. (2000) "A new in Vivo Stable Isotope Method for Measuring Mammary Epithelial Cell Proliferation," *FASEB Journal Experimental Biology* 2000 14(4), Meeting Abstract 550.5: A786.
Mohri, Hiroshi et al. (2001) "Increased Turnover of T Lymphocytes in HIV-1 Infection and its Reduction by Antiretroviral Therapy," *J. Exp. Med.* 194(9): 1277-1287.

Morris, Rebecca J. et al. (1997). "Evidence that a Slowly Cyling Subpopulation of Adult Murine Epidermal Cells Retains Carcinogen," *Cancer Research* 46: 3061-3066.

Morris, Rebecca J. et al. (1997). "Evidence that Cutaneous Carcinogen-initiated Epithelial Cells from Mice are Quiescent Rather than Actively Cyling," *Cancer Research* 57:3436-3443.

Morsches, Bernhard (1976). "Tierexperimentelle Untersuchungen uber die Beziehungen zwischen der Hydroxyprolinausscheidung im Urin und den Hydroxyprolinfraktionen im Serum," *Der Hautarzt* 27: 234-242.

Mosier, D.E. (1995) "CD4.sup.+ Cell Turnover," *Nature* 375:193-194.

Murali-Krishna, K. et al. (1998) "Counting Antigen-Specific CD8 T Cells: A Reevaluation of Bystander Activation during Viral Infection," *Immunity* 8:177-187.

Nagasaka, S. et al. (May 1999). "Endogenous Glucose Production and Glucose Effectiveness in Type 2 Diabetic Subjects Derived From Stable-Labeled Minimal Modal Approach," *Diabetes* 48:1054-1056.

Naik, S. U. et al. (2006). "Pharmacological Activation of Liver X Receptors Promotes Reverse Cholesterol Transport In Vivo," *Circulation* 113:90-97.

Nanjee, M. N. et al. (2001). "Intravenous apoA-I/lecithin Discs Increase Pre-Beta-HDL Concentration in Tissue Fluid and Stimulate Reverse Cholesterol Transport in Humans," *Journal of Lipid Research* 42:1586-1593.

Neese, R. A. et al. (1993) "Measurement of Endogenous Synthesis of Plasma Cholesterol in Rats and Humans Using MIDA," *Am. J. Physiol.* 264: E139-E147.

Neese, R. A. et al. (Nov. 2002) "Measurement in Vivo of Proliferation Rates of Slow Turnover Cells by 2H2O Labeling of the Deoxyribose Moiety of DNA," *PNAS* 99(24): 15345-15350.

Neese, Richard A. et al. (1995) "Gluconeogenesis and Intrahepatic Those Phosphate Flux in Response to Fasting or Substrate Loads," *Journal of Biological Chemistry* 270(24): 14452-14463.

Neese, Richard A. et al. (2001) "Advances in the Stable Isotope-Mass Spectrometric Measurement of DNA Synthesis and Cell Proliferation," *Analytical Biochemistry* 298(2):189-195.

Ong, Shao-En et al. (2002) "Stable Isotope Labeling by Amino Acids in Cell Culture, SILAC, as a Simple and Accurate Approach to Expression Proteomics," *Molecular and Cellular Proteomics* 1: 376-386.

Oshima, M. et al. (2002). "COX Selectivity and Animal Models for Colon Cancer," *Current Pharmaceutical Design* 8:1021-1034.

Ouguerram, K. et al. (Jan. 2002) "A New Labeling Approach Using Stable Isotopes to Study In Vivo Plasma Cholesterol Metabolism in Humans," *Metabolism* 51(1): 5-11.

Oyaizu, N. et al. (1995) "Role of Apoptosis in HIV Disease Pathogenesis," *J. of Clinical Immunology* 15(5):217-231.

Paku, S. (Apr. 2001). "Origin and Structural Evolution of the Early Proliferating Oval Cells in Rat Liver," *American Journal of Pathology* 158(4):1313-1323.

Palmer, L.D. et al. (1997). "Telomere Length, Telomerase Activity, and Replicative Potential in HIV Infection: Analysis of CD4+ and CD8+ T Cells from HIV-discordant Monozygotic Twins," *J. Experimental Medicine* 185(7):1381-1386.

Panteleo, Giuseppe (1999) "Unraveling the Strands of HIV's Web," *Nature Medicine* 5(1): 27-28.

Papageorgopoulos, C. et al.(1993) "Toward the Measurement of Protein Synthesis by Mass Isotopomer Distribution Analysis (MIDA):Resolution of Isotopomers in a [d.sub.3 ]-Leucine Enriched Synthetic Oligopeptide Using Electrospray/Quadrupole Mass Spectrometry (ESI/MS)," Abstract, *Federation of American Societies for Experimental Biology* 1022:A177.

Papageorgopoulos, Christina et al. (1999) "Measuring Protein Synthesis by Mass Isotopomer Distribution Analysis (MIDA)," *Analytical Biochemistry* 267: 1-16.

Park, S. S., et al. (1997). "Measurement of Small Intestinal Cell Turnover with [6,6, 2H2] Glucose," *Berkeley Scientific*, Abstract 10:41-43.

Parks, Elizabeth J. et al. (1999) "Effects of a Low-Fat, High-Carbohydrate Diet on VLDL-Triglyceride Assembly, Production, and Clearance," *J. Clin. Invest.* 104(8): 1087-1096.

Parks, Elizabeth J. et al. (2000) "Carbohydrate-induced Hypertriacylglycerolemia: Historical Perspective and Review of Biological Mechanisms," *Am. J. Nutr.* 71: 412-433.

Parks, Elizabeth J. et al. (2000) "Dependence of Plasma a-Tocopherol Flux on Very Low-Density Triglyceride Clearance in Humans," *Free Radical Biology & Medicine* 29(11): 1151-1159.

Paša-Tolic, Ljiljana et al. (1999) "High Throughput Proteome-Wide Precision Measurements of Protein expression Using Mass Spectrometry," *J. Am. Chem. Soc.* 121: 7949-7950.

Patsalos, P. N. et al. (Oct. 1980). "Pattern of Myelin Breakdown During Sciatic Nerve Wallerian Degeneration: Reversal of the Order of Assembly," *The Journal of Cell Biology* 87:1-5.

Patterson, Bruce W. et al. (1993) "Concentration Dependence of Methyl-Palmitate Isotope Ratios by Electron Impact Ionization Gas Chromatography/Mass Spectrometry," *Biol. Mass Spectrom.* 22: 481-486.

Patterson, Bruce W. et al. (Aug. 1997). "Measurement of Very Low Stable Isotope Enrichments by Gas Chromatography/Mass Spectrometry: Application to Measurement of Muscle Protein Synthesis," *Metabolism* 46(8): 943-948.

Patton, G.M. et al. (Jul. 1979). "Measurements of Fatty Acid Synthesis by Incorporation of Deuterium from Deuterated Water," *Biochemistry* 18(14):3186-3188.

Perelson, A.S. et al.(1996) "HIV-1 Dynamics in Vivo: Virion Clearance Rate, Infected Cell Life-Span, and Viral Generation Time," *Science* 271:1582-1586.

Perelson, A.S. et al.(1997). "Decay Characteristics of HIV-1-Infected Compartments During Combination Therapy," *Nature* 387:188-191.

Perochon, E. et al. (1997). "Radiolabeling of the Lipids of Chinese Hamster Ovary Cells with the Probe [3-(Trifluoromethyl)-3-(m-[125]iodophenyl)diazirine]," *Analytical Biochemistry* 254:109-118.

Pozharisski, K.M. et al. (1980) "Study of Kinetics of Epithelial Cell Populations in Normal Tissues of the Rat's Intestines and in Carcinogenesis," *Exp. Path., Bd.* 18:387-406.

Previs, Stephen F. et al. (2001) "Estimation of Protein Turnover In Vivo Using D2O" *Diabetes Abstract Book*, 61st Scientific Sessions 50[Supplement 2]: A301.

Propper, D. J. et al. (Jan. 2003). "Use of Positron Emission Tomography in Pharmacokinetic Studies to Investigate Therapeutic Advantage in a Phase I Study of 120-Hour Intravenous Infusion XR5000," *Journal of Clinical Oncology* 21(2):203-210.

Ravichandran, L.V. et al., (Jun. 1991) "In vivo labeling studies on the biosynthesis and degradation of collagen in experimental myocardial infarction," *Biochemistry Journal* 24(3): 405-414.

Reichard, P. (1978). "From Deoxynucleotides to DNA Synthesis," *Federation Proceedings* 37(1):9-14.

Reichard, P. (1988) "Interactions Between Deoxyribonucleotide and DNA Synthesis," *Ann. Rev. Biochem.* 57:349-374.

Rittenberg, D. et al. (Feb. 1937). "Deuterium as an Indicator in the Study of Intermediary Metabolism—VIII. Hydrogenation of Fatty Acids in the Animal Organism," *Journal ry of Biological Chemistry* 117:485-490.

Rittenberg, D. et al. (Sep. 1937). "Deuterium as an Indicator in the Study of Intermediary Metabolism—X. The Metabolism of Butyric and Caproic Acids," *Journal of Biological Chemistry* 120:503-510.

Rittler, P. et al. (2003). "Effect of Tumor Removal on Mucosal Protein Synthesis in Patients with Colorectal Cancer," *American Journal of Physiology-Endocrinology and Metabolism* 284:E1018-E1021.

Roberts, S.B. (1989) "Use of the Doubly Labeled Water Method for Measurement of Energy Expenditure, Total Body Water, Water Intake, and Metabolizable Energy Intake in Humans and Small Animals," *Can. J. Physiol. Pharmacol.* 67(10): 1190-1198.

Robin, Eugene D. et al. (1988). "Mitochondria DNA Molecules and Virtual Number of Mitochondria per Cell in Mammalian Cells," *Journal of Cellular Physiology* 136:507-513.

Robosky, L. C. (2002). "In Vivo Toxicity Screening Programs Using Metabonomics," *Combinatorial Chemistry & High Throughput Screening* 5:651-662.

Rocha, B. et al. (1990) "Accumulation of Bromodeoxyuridine-Labelled Cells in Central and Peripheral Lymphoid Organs: Minimal Estimates of Production and Turnover Rates of Mature Lymphocytes," *Eur. J. Immunol.* 20:1697-1708.

Roda, Aldo et al. (1980). "Results with Six 'Kit' Radioimmunoassays for Primary Bile Acids in Human Serum Intercompared," *Clin. Chem.* 26(12): 1677-1682.

Roederer, M. (Jul. 1995) "T-Cell Dynamics of Immunodeficiency," *Nature Medicine* 1(7):621-622.

Rooyackers, Olav E. et al. (Oct. 1996) "Tracer Kinetics Are of Limited Value to Measure In Vivo Protein Synthesis and Degradation Rates in Muscle of Anesthetized Rats," *Metabolism* 45(10): 1279-1283.

Rosin, M. P. et al. (Dec. 1, 1997). "The Use of Exfoliative Cell Samples to Map Clonal Genetic Alterations in the Oral Epithelium of High-Risk Patients," *Cancer Research* 57:52585260.

Royale, G. T. et al. (1981). "Techniques for Investigating Substrate Metabolism in Patients," *Annals of the Royal College of Surgeons of England* 63:415-419.

Sakurai, Y. (1996). "The Meanings of Measuring Biological Metabolism Using a Stable Isotope Labeled Tracer: The Difference in Metabolism Between a Healthy Human and a Patient in Surgically Serious Condition," *Medical Journal of Fukita Academy* 20(1):9-21. [Need English translation.].

Santarelli, L. et al. (Oct. 8, 2003). "Requirement of hippocampal neurogenesis for the behavioral effects of antidepressants," *Science* 301:805-809.

Sawada, S. et al. (1995) "Comparison of Autoradiography, Liquid Scintillation Counting and Immunoenzymatic Staining of 5-bromo-2'-deoxyuridine for Measurement of Unscheduled DNA Synthesis and Replicative DNA Synthesis in Rat Liver," *Mutation Research* 344:109-116.

Scalise, K. (Feb. 11-17, 1998) "Tracking T-Cells in AIDS Patients: A Safe Reliable Method of Measuring Human Cell Generation Rates," *Berkeleyan* p. 3.

Scheibner, J et al. (1993) "Bile Acid Synthesis from Newly Synthesized Vs. Preformed Cholesterol Precursor Pools in the Rat," *Hepatology* 17: 1095-1102.

Scheibner, J et al. (1999) "Complex Feedback Regulation of Bile Acid Synthesis in the Hamster: The Role of Newly Synthsized Cholesterol," *Hepatology* 30: 230-237.

Schneiter, P. et al. (1998). "Kinetics of Dexamethasone Induced Alterations of Glucose Metabolism in Healthy Humans," *American Journal of Physiology* pp. E806-E813.

Schoenheimer, R. et al. (Mar. 1936). "Deuterium as an Indicator in the Study of Intermediary Metabolism—V. The Desaturation of Fatty Acids in Organism," *Journal of Biological Chemistry* 113:505-510.

Schwarz, Jean-Marc et al. (1995) "Short-Term Alterations in Carbohydrate Energy Intake in Humans," *J. Clin. Invest.* 96: 2735-2743.

Shevchenko, Andrej et al. (1997) "Rapid 'de Novo' Peptide Sequencing by a Combination of Nanoelectrospray, Isotopic Labeling and a Quadrupole/Time-of-flight Mass Spectrometer," *Rapid Commun. Mass Spectrom.* 11: 1015-1024.

Shigenaga, M.K. et al. (1994) "Assays of Oxidative DNA Damage Biomarkers 8-Oxo-2'deoxyguanosine and 8-Oxoguanine in Nuclear DNA and Biological Fluids by High-Performance Liquid Chromatography with Electrochemical Detection," *Methods in Enzymology* 234:16-33.

Siler, Scott Q. et al. (1998) "The Inhibition of Gluconeogenesis Following Alcohol in Humans," *Am. J. Physiol.* 275: E897-E907.

Siler, Scott Q. et al. (1998) "VLDL-Triglyceride Production After Alcohol Ingestion, Studied Using [2-13C1] Glycerol," *J. Lipid Res.* 39: 2319-2328.

Smith, et al. (1983) "The Phosphogluconate Odixative Pathway," in *Principles of Biochemistry*, 7th edition, McGraw-Hill Book Company, pp. 417-423.

Sosa-Peinado, A. et al. (Jul. 2000). "Overexpression and Biosynthetic Deuterium Enrichment of TEM-1 Beta-Lactamase for Structural Characterization by Magnetic Resonance Methods," *Protein Expression and Purification* 19(2):235-245.

Sprent, J. et al. (1995) "CD4+ Cell Turnover," *Nature* 375:194.

Stingl et al. (2001). *Breast Can Res and Treatment*, 67:93-109.

Stingl et al. (Feb. 2006). *Nature* 439:993-997.

Sunter, J.P. et al. (1978). "Cell Population Kinetics in the Epithelium of the Colon of the Male Rat." *Virchows Archiv. B Cell Path.* 26: 275-287.

Supplementary European Search Report mailed Jul. 28, 2009, for EP Application No. 04809469.2 filed Jun. 29, 2004, 4 pages.

Supplementary European Search Report mailed Jun. 30, 2009, for EP Application No. 05725448.4 filed Mar. 11, 2005, 7 pages.

Supplementary European Search Report mailed Sep. 19, 2008, for EP Application No. 05733311.4 filed Feb. 2, 2005, 9 pages.

Supplementary Partial European Search Report mailed Aug. 17, 2005, for EP Application No. 03749756.7 filed Sep. 15, 2003, 6 pages.

Supplementary Partial European Search Report mailed Jul. 25, 2006, for EP Application No. 02806603.3 filed Oct. 23, 2002, 5 pages.

Supplementary Partial European Search Report mailed Mar. 9, 2006, for European Patent Application No. EP 03713429.3, filed Feb. 12, 2003, 6 pages.

Supplementary Partial European Search Report mailed Sep. 22, 2006, for European patent application No. EP 03768624.3, filed Nov. 4, 2003, 4 pages.

Teixeira, L et al. (2001) "Poor CD4 T Cell Restoration After Supression of HIV-1 Replication May Reflect Lower Thymic Function," *AIDS* 15(14):1749-1756.

Tint, G.S. et al. (1974). "Transformation of 5α-cholest-7-en-3β-ol to Cholesterol and Cholestanol in Cerebrotendinous Xanthomatosis," *Journal of Lipid Research* 15: 256-262.

Traber, P.G. et al. (1991) "Isolation of Intestinal Epithelial Cells for the Study of Differential Gene Expression Along the Crypt-Villus Axis," *Am. J. Physiol.* 260:G895-G903.

Trappe, T. A. et al. (2002) "Effect of Ibuprofen and Acetaminophen on Postexercise Muscle Protein Synthesis," *Am J Physiol Endocronol Metab* 282: E551-E556.

Turner, S. M. (2006). "Stable Isotopes, Mass Spectrometry, and Molecular Fluxes: Applications to Toxicology," *Journal of Pharmacological and Toxicological Methods* 53:75-85.

Turner, S. M. et al. (2005). "Emerging Applications of Kinetic Biomarkers in Preclinical and Clinical Drug Development," *Current Opinion in Drug Discovery & Development* 8(1): 115-126.

Turner, Scott M. et al. (2002) "Measurement of Triglyceride (TG) Synthesis in Vivo 2H2O Incorporation into TG-Glycerol and Application of Mass Isotopomer Distribution Analysis (MIDA)," *Experimental Biology* 2002 16[Meeting Abstract 361.9]: A400.

U.S. Office Action mailed on Jun. 26, 2006, for U.S. Appl. No. 10/366,125, filed Feb. 12, 2003, 11 pages.

U.S. Office Action mailed on Mar. 5, 2007, for U.S. Appl. No. 10/366,125, filed Feb. 12, 2003, 6 pages.

U.S. Office Action mailed on Oct. 18, 2005, for U.S. Appl. No. 10/366,125, filed Feb. 12, 2003, 29 pages.

Van Hinsbergh, V.W.M. et al. (1978). "Palmitate Oxidation by Rat Skeletal Muscle Mitochondria," *Archives of Biochemistry and Biophysics* 190(2): 762-771.

Van Loan, Marta D. et al. (1999) "Monitoring Changes in Fat-Free Mass in HIV-Positive Men With Hypotestosteronemia and AIDS Wasting Syndrome Treated With Gonadal Hormone Replacement Therapy," *AIDS* 13:241-248.

Veenstra, Timothy D. et al. (2000) "Proteome Analysis Using Selective Incorporation of Isotopically Labeled Amino Acids," *J. Am. Soc. Mass. Spectrom.* 11: 78-82.

Veerkamp, Jacques H. et al. (1986) "14CO2 Production Is No Adequate Measure of [14C]Fatty Acid Oxidation," *Biochemical Medicine and Metabolic Biology* 35: 248-259.

Véniant, Murielle M. et al. (2000) "Defining the Atherogenicity of Large and Small Lipoproteins Containing Apolipoproteins B100," *J. Clin. Invest.* 106(12): 1501-1510.

Wadke, M. et al. (Jul. 1973). "Fatty Acid Synthesis by Liver Perfused with Deuterated and Tritiated Water," *Biochemistry* 12(14):2619-2624.

Wain-Hobson, S. (1995) "Virological Mayhem, " *Nature* 373:102.

Waldeman, F.M. et al. (1991) "A Comparison Between Bromodeoxyuridine and 3 H THymidine Labeling in Human Breast Tumors," *Modern Path.* 4(6):718-722.

Wang, Wei et al. (2000) "Effects of Nicotinic Acid on Fatty Acid Kinetics, Fuel Selection, and Pathways of Glucose Production in Women," *Am. J. Physiol. Endocrinol. Metab.* 279: E50-E59.

Waterlow, J.C. (1980) "Protein Turnover in the Whole Animal," *Invest. Cell Pathol.* 3: 107-119.

Wei, X et al. (1995) "Viral Dynamics in Human Immunodeficiency Virus Type 1 Infection," *Nature* 373:117-122.

Whittmann and Heinzle (2001). "Application of MALDI-TOF MS to lysine-producing *Corynebacterium glutamicum*: a novel approach for metabolic flux analysis," *Eur. J. Biochem.* 268:2441-2455.

Winett, Richard et al. (2000) "Exercise Regimens for Men With HIV," *JAMA* 28441 175-6.

Wolf, George (1995) "The Effect of Fasting and Fructose and Glucose Infusion on Gluconeogenesis and Triose Phosphate Flux in Rats in Vivo," *Nutrition Reviews* 53(10): 299-302.

Wolfe, R. (1990) "Isotopic Measurement of Glucose and Lactate Kinetics," *Ann. Med.* 22:163-170.

Wolfe, R. et al. (1984). "Glucose Metabolism in Humans," *ACS Symposium Series* 258, Chapter 12, Turnund et al. ed., pp. 175-189.

Wolthers et al. (1998) "Rapid CD4+ T-Cell Turnover in HIV-1 Infection: a Paradigm Revisited," *Immunol. Today* 19(1):44-48.

Wolthers, K. C. et al. (1996) "T Cell Telomere Length in HIV-1 Infection: No Evidence for Increased CD4+ T Cell Turnover," *Science* 274:1543-1547.

Wong, M-L et al. (Jan. 30, 2004). "From monoamines to genomic targets: a paradigm shift for drug discovery in depression, " *Nature Reviews: Drug Discovery* 3(2): 136-151.

Wood, H. G. et al. (1963) "Estimation of Pathways of Carbohydrate Metabolism," *Biochemische Zeitschrift* 338:809-847.

Written Opinion mailed Jul. 14, 2006, by the Australian Patent Office for Singapore patent application No. 200502593-7, filed Nov. 4, 2003, 5 pages.

Zhang, B.-L. et al. (2006). "Deuterium NMR Study of of Hydrogen in Fatty Acids Produced In Vivo in Chicken," *European Journal of Lipid Science and Technology* 108:125-133.

Zhang, Z-Q. et al. (Feb. 1998) "Kinetics of CD4+ T Cell Repopulation of Lymphoid Tissues after Treatment of HIV-1 Infection," *Proc. Natl. Acad. Sci. USA* 95:1154-1159.

Zilversmit, D.B. et al. (1943) "On the Calculation of 'Turnover Time' and 'Turnover Rate' from Experiments Involving the Use of Labeling Agents," *J. of General Physiology* 26(3):325-331.

McFarland et al., "Inhibition of DNA synthesis in neonatal rat brain regions caused by acute nicotine administration", Developmental Brain Research, vol. 58, No. 2, Feb. 22, 1991, pp. 223-229.

Ramakers et al., "Chronic suppression of bioelectric activity and cell survival in primary cultures of rat cerebral cortex: biochemical observations", European Journal of Neuroscience, vol. 3, No. 2, Feb. 1991, pp. 154-161.

European Search Report received for EP Patent Application No. 04812281.6, mailed on Oct. 6, 2010, 4 pages.

Hellerstein et al., "Subpopulations of long-lived and short-lived T cells in advanced HIV-1 infection", The Journal of Clinical Investigation, vol. 112, No. 6, Sep. 2003, pp. 956-966.

Siler et al., "De novo lipogenesis, lipid kinetics, and whole-body lipid balances in humans after acute alcohol consumption)-3", The American Journal of Clinical Nutrition, vol. 70, 1999, pp. 928-936.

Bantscheff et al., "Quantitative mass spectrometry in proteomics: a critical review", Analytical and Bioanalytical Chemistry, vol. 389, 2007, pp. 1017-1031.

Extended European Search Report received for European Patent Application No. 06759050.5, mailed on Mar. 31, 2011, 7 pages.

Wang et al., "Validation of a Single-Isotope-Labeled Cholesterol Tracer Approach for Measuring Human Cholesterol Absorption", Lipids, vol. 39, No. 1, 2004, pp. 87-91.

Jones et al., "Modulation of plasma lipid levels and cholesterol kinetics by phytosterol versus phytostanol esters", Journal of Lipid Research, vol. 41, 2000, pp. 697-705.

Extended European Search Report received for European Patent Application No. 06784805.1, mailed on Mar. 21, 2011, 7 pages.

Shen et al., "Purification of oligodendrocyte and its myelination to the demyelinated culture model in vitro", Acta Histochem. Cytochem., vol. 35, No. 2, 2002, p. 123.

Murphy et al., "A new Sensitive In Vivo Diagnostic Test of Insulin Resistance: The Deuterated Oral Glucose Tolerance Test (2H-OGTT)", Diabetes, American Diabetes Association, vol. 53, No. Suppl. 02, Jan. 1, 2004, 2 pages.

Office Action received for European Patent Application No. 06759050.5, mailed on Apr. 19, 2011, 1 page.

Office Action received for European Patent Application No. 06784805.1, mailed on Apr. 7, 2011, 1 page.

FIGURE 8B

SEQUENCE LISTING

<160> NUMBER OF SEQ ID NOS: 28

<210> SEQ ID NO 1
<211> LENGTH: 17
<212> TYPE: PRT
<213> ORGANISM: Homo sapiens

<400> SEQUENCE: 1

Gln Leu Ser Tyr Gly Tyr Asp Glu Lys Ser Thr Gly Gly Ile Ser Val
1               5                   10                  15

Pro

<210> SEQ ID NO 2
<211> LENGTH: 8
<212> TYPE: PRT
<213> ORGANISM: Homo sapiens

<400> SEQUENCE: 2

Gln Tyr Asp Gly Lys Gly Val Gly
1               5

<210> SEQ ID NO 3
<211> LENGTH: 11
<212> TYPE: PRT
<213> ORGANISM: Homo sapiens

<400> SEQUENCE: 3

Gln Tyr Asp Gly Lys Gly Val Gly Leu Gly Pro
1               5                   10

<210> SEQ ID NO 4
<211> LENGTH: 19
<212> TYPE: PRT
<213> ORGANISM: Homo sapiens

<400> SEQUENCE: 4

Gln Met Ala Gly Gly Phe Asp Glu Lys Ala Gly Gly Ala Gln Leu Gly
1               5                   10                  15

Val Met Gln

-continued

```
<210> SEQ ID NO 5
<211> LENGTH: 14
<212> TYPE: PRT
<213> ORGANISM: Homo sapiens

<400> SEQUENCE: 5

Gln Tyr Asp Ser Tyr Asp Val Lys Ser Gly Val Ala Val Gly
 1               5                  10

<210> SEQ ID NO 6
<211> LENGTH: 26
<212> TYPE: PRT
<213> ORGANISM: Homo sapiens

<400> SEQUENCE: 6

Ser Ala Gly Phe Asp Phe Ser Phe Leu Pro Gln Pro Pro Gln Glu Lys
 1               5                  10                  15

Ala His Asp Gly Gly Arg Tyr Tyr Arg Ala
             20                  25

<210> SEQ ID NO 7
<211> LENGTH: 12
<212> TYPE: PRT
<213> ORGANISM: Homo sapiens

<400> SEQUENCE: 7

Tyr Asp Phe Gly Tyr Asp Gly Asp Phe Tyr Arg Ala
 1               5                  10

<210> SEQ ID NO 8
<211> LENGTH: 6
<212> TYPE: PRT
<213> ORGANISM: Homo sapiens

<400> SEQUENCE: 8

Glu Lys Gly Pro Asp Pro
 1               5

<210> SEQ ID NO 9
<211> LENGTH: 3
<212> TYPE: PRT
<213> ORGANISM: Homo sapiens

<400> SEQUENCE: 9

Gly Val Lys
 1

<210> SEQ ID NO 10
<211> LENGTH: 24
<212> TYPE: PRT
<213> ORGANISM: Homo sapiens

<400> SEQUENCE: 10

Ile Asp Met Ser Ala Phe Ala Gly Leu Gly Pro Arg Glu Lys Gly Pro
 1               5                  10                  15

Asp Pro Leu Gln Tyr Met Arg Ala
             20

<210> SEQ ID NO 11
<211> LENGTH: 25
<212> TYPE: PRT
<213> ORGANISM: Homo sapiens

<400> SEQUENCE: 11

Cys Gly Gly Val Gly Ala Ala Ala Ile Ala Gly Ile Gly Gly Glu Lys
```

-continued

```
                1               5                  10                  15
Ala Gly Gly Phe Ala Pro Tyr Tyr Gly
            20                  25

<210> SEQ ID NO 12
<211> LENGTH: 139
<212> TYPE: PRT
<213> ORGANISM: Homo sapiens

<400> SEQUENCE: 12

Gln Glu Glu Gly Gln Val Glu Gly Gln Asp Glu Asp Ile Pro Pro Ile
1               5                   10                  15

Thr Cys Val Gln Asn Gly Leu Arg Tyr His Asp Arg Asp Val Trp Lys
            20                  25                  30

Pro Glu Pro Cys Arg Ile Cys Val Cys Asp Asn Gly Lys Val Leu Cys
        35                  40                  45

Asp Asp Val Ile Cys Asp Glu Thr Lys Asn Cys Pro Gly Ala Glu Val
    50                  55                  60

Pro Glu Gly Glu Cys Cys Pro Val Cys Pro Asp Gly Ser Glu Ser Pro
65                  70                  75                  80

Thr Asp Gln Glu Thr Thr Gly Val Glu Gly Pro Lys Gly Asp Thr Gly
                85                  90                  95

Pro Arg Gly Pro Arg Gly Pro Ala Gly Pro Pro Gly Arg Asp Gly Ile
            100                 105                 110

Pro Gly Gln Pro Gly Leu Pro Gly Pro Pro Gly Pro Pro Gly Pro Pro
        115                 120                 125

Gly Pro Pro Gly Leu Gly Gly Asn Phe Ala Pro
    130                 135

<210> SEQ ID NO 13
<211> LENGTH: 246
<212> TYPE: PRT
<213> ORGANISM: Homo sapiens

<400> SEQUENCE: 13

Asp Asp Ala Asn Val Val Arg Asp Arg Asp Leu Glu Val Asp Thr Thr
1               5                   10                  15

Leu Lys Ser Leu Ser Gln Gln Ile Glu Asn Ile Arg Ser Pro Glu Gly
            20                  25                  30

Ser Arg Lys Asn Pro Ala Arg Thr Cys Arg Asp Leu Lys Met Cys His
        35                  40                  45

Ser Asp Trp Lys Ser Gly Glu Tyr Trp Ile Asp Pro Asn Gln Gly Cys
    50                  55                  60

Asn Leu Asp Ala Ile Lys Val Phe Cys Asn Met Glu Thr Gly Glu Thr
65                  70                  75                  80

Cys Val Tyr Pro Thr Gln Pro Ser Val Ala Gln Lys Asn Trp Tyr Ile
                85                  90                  95

Ser Lys Asn Pro Lys Asp Lys Arg His Val Trp Phe Gly Glu Ser Met
            100                 105                 110

Thr Asp Gly Phe Gln Phe Glu Tyr Gly Gly Gln Gly Ser Asp Pro Ala
        115                 120                 125

Asp Val Ala Ile Gln Leu Thr Phe Leu Arg Leu Met Ser Thr Glu Ala
    130                 135                 140

Ser Gln Asn Ile Thr Tyr His Cys Lys Asn Ser Val Ala Tyr Met Asp
145                 150                 155                 160

Gln Gln Thr Gly Asn Leu Lys Lys Ala Leu Leu Leu Lys Gly Ser Asn
                165                 170                 175
```

-continued

```
Glu Ile Glu Ile Arg Ala Glu Gly Asn Ser Arg Phe Thr Tyr Ser Val
            180                 185                 190

Thr Val Asp Gly Cys Thr Ser His Thr Gly Ala Trp Gly Lys Thr Val
        195                 200                 205

Ile Glu Tyr Lys Thr Thr Lys Thr Ser Arg Leu Pro Ile Ile Asp Val
210                 215                 220

Ala Pro Leu Asp Val Gly Ala Pro Asp Gln Glu Phe Gly Phe Asp Val
225                 230                 235                 240

Gly Pro Val Cys Phe Leu
                245

<210> SEQ ID NO 14
<211> LENGTH: 55
<212> TYPE: PRT
<213> ORGANISM: Homo sapiens

<400> SEQUENCE: 14

Leu Gln Glu Glu Thr Val Arg Lys Gly Pro Ala Gly Asp Arg Gly Pro
1               5                   10                  15

Arg Gly Glu Arg Gly Pro Pro Gly Pro Pro Gly Arg Asp Gly Glu Asp
                20                  25                  30

Gly Pro Thr Gly Pro Pro Gly Pro Pro Gly Pro Pro Gly Pro Pro Gly
            35                  40                  45

Leu Gly Gly Asn Phe Ala Ala
        50                  55

<210> SEQ ID NO 15
<211> LENGTH: 265
<212> TYPE: PRT
<213> ORGANISM: Homo sapiens

<400> SEQUENCE: 15

Gly Val Ser Gly Gly Tyr Asp Phe Gly Tyr Asp Gly Asp Phe Tyr
1               5                   10                  15

Arg Ala Asp Gln Pro Arg Ser Ala Pro Ser Leu Arg Pro Lys Asp Tyr
                20                  25                  30

Glu Val Asp Ala Thr Leu Lys Ser Leu Asn Asn Gln Ile Glu Thr Leu
            35                  40                  45

Leu Thr Pro Glu Gly Ser Arg Lys Asn Pro Ala Arg Thr Cys Arg Asp
50                  55                  60

Leu Arg Leu Ser His Pro Glu Trp Ser Ser Gly Tyr Tyr Trp Ile Asp
65                  70                  75                  80

Pro Asn Gln Gly Cys Thr Met Glu Ala Ile Lys Val Tyr Cys Asp Phe
                85                  90                  95

Pro Thr Gly Glu Thr Cys Ile Arg Ala Gln Pro Glu Asn Ile Pro Ala
            100                 105                 110

Lys Asn Trp Tyr Arg Ser Ser Lys Asp Lys His Val Trp Leu Gly
        115                 120                 125

Glu Thr Ile Asn Ala Gly Ser Gln Phe Glu Tyr Asn Val Glu Gly Val
130                 135                 140

Thr Ser Lys Glu Met Ala Thr Gln Leu Ala Phe Met Arg Leu Leu Ala
145                 150                 155                 160

Asn Tyr Ala Ser Gln Asn Ile Thr Tyr His Cys Lys Asn Ser Ile Ala
                165                 170                 175

Tyr Met Asp Glu Glu Thr Gly Asn Leu Lys Lys Ala Val Ile Leu Gln
            180                 185                 190
```

```
Gly Ser Asn Asp Val Glu Leu Val Ala Glu Gly Asn Ser Arg Phe Thr
            195                 200                 205

Tyr Thr Val Leu Val Asp Gly Cys Ser Lys Lys Thr Asn Glu Trp Gly
    210                 215                 220

Lys Thr Ile Ile Glu Tyr Lys Thr Asn Lys Pro Ser Arg Leu Pro Phe
225                 230                 235                 240

Leu Asp Ile Ala Pro Leu Asp Ile Gly Gly Ala Asp His Glu Phe Phe
                245                 250                 255

Val Asp Ile Gly Pro Val Cys Phe Lys
            260                 265

<210> SEQ ID NO 16
<211> LENGTH: 167
<212> TYPE: PRT
<213> ORGANISM: Homo sapiens

<400> SEQUENCE: 16

Met Ile Arg Leu Gly Ala Pro Gln Ser Leu Val Leu Leu Thr Leu Leu
1               5                   10                  15

Val Ala Ala Val Leu Arg Cys Gln Gly Gln Asp Val Arg Gln Pro Gly
            20                  25                  30

Pro Lys Gly Gln Lys Gly Glu Pro Gly Asp Ile Lys Asp Ile Val Gly
        35                  40                  45

Pro Lys Gly Pro Pro Gly Pro Gln Gly Pro Ala Gly Glu Gln Gly Pro
    50                  55                  60

Arg Gly Asp Arg Gly Asp Lys Gly Glu Lys Gly Ala Pro Gly Pro Arg
65                  70                  75                  80

Gly Arg Asp Gly Glu Pro Gly Thr Pro Gly Asn Pro Gly Pro Pro Gly
            85                  90                  95

Pro Pro Gly Pro Pro Gly Pro Pro Gly Leu Gly Gly Asn Phe Ala Ala
        100                 105                 110

Gln Met Ala Gly Gly Phe Asp Glu Lys Ala Gly Gly Ala Gln Leu Gly
    115                 120                 125

Val Met Gln Gly Pro Met Gly Pro Met Gly Pro Arg Gly Pro Pro Gly
130                 135                 140

Pro Ala Gly Ala Pro Gly Pro Gln Gly Phe Gln Gly Asn Pro Gly Glu
145                 150                 155                 160

Pro Gly Glu Pro Gly Val Ser
            165

<210> SEQ ID NO 17
<211> LENGTH: 246
<212> TYPE: PRT
<213> ORGANISM: Homo sapiens

<400> SEQUENCE: 17

Asp Glu Ala Ala Gly Gly Leu Arg Gln His Asp Val Glu Val Asp Ala
1               5                   10                  15

Thr Leu Lys Ser Leu Asn Asn Gln Ile Glu Ser Ile Arg Ser Pro Glu
            20                  25                  30

Gly Ser Lys Lys Asn Pro Ala Arg Thr Cys Arg Asp Ile Lys Leu Cys
        35                  40                  45

His Pro Glu Trp Lys Ser Gly Asp Tyr Trp Ile Asp Pro Asn Gln Gly
    50                  55                  60

Cys Thr Leu Asp Ala Ile Lys Val Phe Cys Asn Met Glu Thr Gly Glu
65                  70                  75                  80

Thr Cys Val Tyr Pro Thr Pro Ser Ser Ile Pro Arg Lys Asn Trp Trp
```

-continued

```
                    85                  90                  95
Thr Ser Lys Thr Lys Asp Lys Lys His Val Trp Phe Ala Glu Thr Ile
                100                 105                 110

Asn Gly Gly Phe His Phe Ser Tyr Gly Asp Glu Asn Leu Ser Pro Asn
                115                 120                 125

Thr Ala Ser Ile Gln Met Thr Phe Leu Arg Leu Leu Ser Thr Glu Gly
                130                 135                 140

Ser Gln Asn Val Thr Tyr His Cys Lys Asn Ser Ile Ala Tyr Met Asp
145                 150                 155                 160

Glu Glu Thr Gly Asn Leu Lys Lys Ala Ile Leu Ile Gln Gly Ser Asn
                165                 170                 175

Asp Val Glu Ile Arg Ala Glu Gly Asn Ser Arg Phe Thr Tyr Ser Val
                180                 185                 190

Leu Glu Asp Gly Cys Thr Lys His Thr Gly Lys Trp Gly Lys Thr Val
                195                 200                 205

Ile Glu Tyr Arg Ser Gln Lys Thr Ser Arg Leu Pro Ile Val Asp Ile
                210                 215                 220

Ala Pro Met Asp Ile Gly Gly Ala Asp Gln Glu Phe Gly Val Asp Ile
225                 230                 235                 240

Gly Pro Val Cys Phe Leu
                245
```

<210> SEQ ID NO 18
<211> LENGTH: 125
<212> TYPE: PRT
<213> ORGANISM: Homo sapiens

<400> SEQUENCE: 18

```
Gln Gln Glu Ala Val Glu Gly Gly Cys Ser His Leu Gly Gln Ser Tyr
1               5                   10                  15

Ala Asp Arg Asp Val Trp Lys Pro Glu Pro Cys Gln Ile Cys Val Cys
                20                  25                  30

Asp Ser Gly Ser Val Leu Cys Asp Asp Ile Ile Cys Asp Asp Gln Glu
                35                  40                  45

Leu Asp Cys Pro Asn Pro Glu Ile Pro Phe Gly Glu Cys Cys Ala Val
                50                  55                  60

Cys Pro Gln Pro Pro Thr Ala Pro Thr Arg Pro Pro Asn Gly Gln Gly
65                  70                  75                  80

Pro Gln Gly Pro Lys Gly Asp Pro Gly Pro Pro Gly Ile Pro Gly Arg
                85                  90                  95

Asn Gly Asp Pro Gly Ile Pro Gly Gln Pro Gly Ser Pro Gly Ser Pro
                100                 105                 110

Gly Pro Pro Gly Ile Cys Glu Ser Cys Pro Thr Gly Pro
                115                 120                 125
```

<210> SEQ ID NO 19
<211> LENGTH: 262
<212> TYPE: PRT
<213> ORGANISM: Homo sapiens

<400> SEQUENCE: 19

```
Ile Ala Gly Ile Gly Gly Glu Lys Ala Gly Gly Phe Ala Pro Tyr Tyr
1               5                   10                  15

Gly Asp Glu Pro Met Asp Phe Lys Ile Asn Thr Asp Glu Ile Met Thr
                20                  25                  30

Ser Leu Lys Ser Val Asn Gly Gln Ile Glu Ser Leu Ile Ser Pro Asp
                35                  40                  45
```

```
Gly Ser Arg Lys Asn Pro Ala Arg Asn Cys Arg Asp Leu Lys Phe Cys
         50                  55                  60

His Pro Glu Leu Lys Ser Gly Glu Tyr Trp Val Asp Pro Asn Gln Gly
 65                  70                  75                  80

Cys Lys Leu Asp Ala Ile Lys Val Phe Cys Asn Met Glu Thr Gly Glu
                 85                  90                  95

Thr Cys Ile Ser Ala Asn Pro Leu Asn Val Pro Arg Lys His Trp Trp
            100                 105                 110

Thr Asp Ser Ser Ala Glu Lys Lys His Val Trp Phe Gly Glu Ser Met
            115                 120                 125

Asp Gly Gly Phe Gln Phe Ser Tyr Gly Asn Pro Glu Leu Pro Glu Asp
        130                 135                 140

Val Leu Asp Val Gln Leu Ala Phe Leu Arg Leu Leu Ser Ser Arg Ala
145                 150                 155                 160

Ser Gln Asn Ile Thr Tyr His Cys Lys Asn Ser Ile Ala Tyr Met Asp
                165                 170                 175

Gln Ala Ser Gly Asn Val Lys Lys Ala Leu Lys Leu Met Gly Ser Asn
            180                 185                 190

Glu Gly Glu Phe Lys Ala Glu Gly Asn Ser Lys Phe Thr Tyr Thr Val
        195                 200                 205

Leu Glu Asp Gly Cys Thr Lys His Thr Gly Glu Trp Ser Lys Thr Val
210                 215                 220

Phe Glu Tyr Arg Thr Arg Lys Ala Val Arg Leu Pro Ile Val Asp Ile
225                 230                 235                 240

Ala Pro Tyr Asp Ile Gly Gly Pro Asp Gln Glu Phe Gly Val Asp Val
                245                 250                 255

Gly Pro Val Cys Phe Leu
            260

<210> SEQ ID NO 20
<211> LENGTH: 26
<212> TYPE: PRT
<213> ORGANISM: Homo sapiens

<400> SEQUENCE: 20

Met Gly Pro Arg Leu Ser Val Trp Leu Leu Leu Leu Pro Ala Ala Leu
 1               5                  10                  15

Leu Leu His Glu Glu His Ser Arg Ala Ala
                 20                  25

<210> SEQ ID NO 21
<211> LENGTH: 28
<212> TYPE: PRT
<213> ORGANISM: Homo sapiens

<400> SEQUENCE: 21

Met Gly Arg Asp Gln Arg Ala Val Ala Gly Pro Ala Leu Arg Arg Trp
 1               5                  10                  15

Leu Leu Leu Gly Thr Val Thr Val Gly Phe Leu Ala
                 20                  25

<210> SEQ ID NO 22
<211> LENGTH: 158
<212> TYPE: PRT
<213> ORGANISM: Homo sapiens

<400> SEQUENCE: 22

Leu Leu Ala Gln Ser Val Leu Gly Gly Val Lys Lys Leu Asp Val Pro
```

```
                1               5                  10                  15
Cys Gly Gly Arg Asp Cys Ser Gly Gly Cys Gln Cys Tyr Pro Glu Lys
            20                  25                  30

Gly Ala Arg Gly Gln Pro Gly Ala Val Gly Pro Gln Gly Tyr Asn Gly
            35                  40                  45

Pro Pro Gly Leu Gln Gly Phe Pro Gly Leu Gln Gly Arg Lys Gly Asp
    50                  55                  60

Lys Gly Glu Arg Gly Val Pro Gly Pro Thr Gly Pro Lys Gly Asp Val
65                  70                  75                  80

Gly Ala Arg Gly Val Ser Gly Phe Pro Gly Ala Asp Gly Ile Pro Gly
            85                  90                  95

His Pro Gly Gln Gly Gly Pro Arg Gly Arg Pro Gly Tyr Asp Gly Cys
            100                 105                 110

Asn Gly Thr Arg Gly Asp Ala Gly Pro Gln Gly Pro Ser Gly Ser Gly
            115                 120                 125

Gly Phe Pro Gly Leu Pro Gly Pro Gln Gly Pro Lys Gly Gln Lys Gly
        130                 135                 140

Glu Pro Tyr Ala Leu Ser Lys Glu Asp Arg Asp Lys Tyr Arg
145                 150                 155

<210> SEQ ID NO 23
<211> LENGTH: 28
<212> TYPE: PRT
<213> ORGANISM: Homo sapiens

<400> SEQUENCE: 23

Met Ser Ala Arg Thr Ala Pro Arg Pro Gln Val Leu Leu Leu Pro Leu
1               5                   10                  15

Leu Leu Val Leu Leu Ala Ala Ala Pro Ala Ala Ser
            20                  25

<210> SEQ ID NO 24
<211> LENGTH: 38
<212> TYPE: PRT
<213> ORGANISM: Homo sapiens

<400> SEQUENCE: 24

Met Trp Ser Leu His Ile Val Leu Met Arg Cys Ser Phe Arg Leu Thr
1               5                   10                  15

Lys Ser Leu Ala Thr Gly Pro Trp Ser Leu Ile Leu Ile Leu Phe Ser
            20                  25                  30

Val Gln Tyr Val Tyr Gly
            35

<210> SEQ ID NO 25
<211> LENGTH: 26
<212> TYPE: PRT
<213> ORGANISM: Homo sapiens

<400> SEQUENCE: 25

Met Lys Leu Arg Gly Val Ser Leu Ala Ala Gly Leu Phe Leu Leu Ala
1               5                   10                  15

Leu Ser Leu Trp Gly Gln Pro Ala Glu Ala
            20                  25

<210> SEQ ID NO 26
<211> LENGTH: 21
<212> TYPE: PRT
<213> ORGANISM: Homo sapiens
```

```
<400> SEQUENCE: 26

Met Leu Ile Asn Lys Leu Trp Leu Leu Leu Val Thr Leu Cys Leu Thr
1               5                   10                  15

Glu Glu Leu Ala Ala
            20

<210> SEQ ID NO 27
<211> LENGTH: 40
<212> TYPE: PRT
<213> ORGANISM: Homo sapiens

<400> SEQUENCE: 27

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 28
<211> LENGTH: 42
<212> TYPE: PRT
<213> ORGANISM: Homo sapiens

<400> SEQUENCE: 28

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

MEASUREMENT OF BIOSYNTHESIS AND BREAKDOWN RATES OF BIOLOGICAL MOLECULES THAT ARE INACCESSIBLE OR NOT EASILY ACCESSIBLE TO DIRECT SAMPLING, NON-INVASIVELY, BY LABEL INCORPORATION INTO METABOLIC DERIVATIVES AND CATABOLITIC PRODUCTS

CROSS REFERENCE TO RELATED APPLICATIONS

This application is a Continuation of U.S. patent application Ser. No. 10/366,125, filed Feb. 12, 2003, this application also claims the benefit of U.S. Provisional Patent Application No. 60/356,008 filed on Feb. 12, 2002, both of which are incorporated herein by reference in their entirety.

FIELD OF THE INVENTION

This invention relates techniques for the measurement of the rate of biosynthesis and breakdown of biological molecules and polymers. More particularly, it relates to techniques for measuring the rates of biosynthesis and breakdown of biological molecules, especially those of the polymeric class and in tissues or other locations that are inaccessible or not easily accessible to direct sampling, in a non-invasive manner in individuals without having to sample the biological molecules directly in the tissues of interest.

BACKGROUND OF THE INVENTION

Publications referred to by reference numbering in this specification correspond to the reference list at the end of the specification are hereby incorporated by reference in their entirety.

Various ways of measuring rates of synthesis or breakdown of biological polymers and other biological molecules of interest have been described. One such invasive method involves the collection of tissues by various invasive procedures, e.g., surgical excision, percutaneous biopsy, post-mortem analysis, or other sampling procedures (termed "invasive" procedures herein), after administration of an isotopically labeled precursor molecule, then isolation of the polymer or other molecule of interest from the tissue so collected, followed by measurement of the isotopic content or labeling pattern in said polymer or other molecule and calculation of the synthesis or breakdown rate of said polymer or other molecule based on the rate of isotope incorporation. This method has some disadvantages that include, inter alia, the need for invasive tissue measurements with attendant medical risk, discomfort, need for expert medical involvement, and limitations on the number of measurements that can be performed.

Another invasive method involves repeated collection of tissue by the invasive procedures listed above after an intervention with measurement of the content (concentration or pool size) of the polymer or other molecule of interest in each tissue sample, and calculation of the rate of change in the net pool size over time, thereby determining the net synthesis (accrual) or net breakdown (depletion) rate. This method has some disadvantages that include, inter alia, the need for repeated measurements and the lack of a true synthetic or breakdown rate measured, with instead a net accrual or depletion rate generated. Further, it is a well-recognized principle in biochemistry that net changes in concentration (accrual or depletion) are not identical to and do not reveal true or absolute rates of synthesis or breakdown (7), because concurrent synthesis and breakdown (herein termed "turnover") is not measured or accounted for by net changes in concentration.

A method that is commonly used in medical practice involves the indirect estimate of pool size or concentration, and their changes over time, by use of repeated radiographic measurements (e.g., x-rays or dual-energy-X-ray absorptiometry for estimating bone mass (4); nuclear magnetic resonance imaging or computerized tomography for estimating muscle or fat mass (9); radiographic procedures for estimating tumor mass). This approach suffers from the same limitations as direct biochemical measurements of concentrations or pool sizes of molecules (noted above), in addition to limitations of accuracy.

Another non-invasive method that has been used involves the collection of a breakdown product that is specific for and derived from a biological molecule or other molecule of interest and that is secreted or excreted into blood or urine, and calculation of the breakdown rate of the biological molecule or other molecule based on the recovery of said breakdown product. (10, 11). This method has some disadvantages that include, inter alia, the inability to measure synthesis rates or true breakdown rates, rather than a net release rate, and other technical limitations that are well-described for these methods (e.g., incomplete recovery of breakdown products due to their biological clearance and catabolism in the organism; interference by delayed or unpredictable excretion of the breakdown products; etc).

The disadvantages and limitations of these prior methods for measuring the synthesis and breakdown rates of biological molecules located in inaccessible tissues inaccessible biological samples are substantial and have held back important fields, including medical diagnostics, drug discovery, genetics, functional genomics and basic research. The disadvantages noted here are not intended to be comprehensive; many other limitations and disadvantages of these methods exist and could be mentioned.

An optimal non-invasive method of measuring rates of biosynthesis and breakdown rates of biological molecules would have the following characteristics: accuracy, capacity to measure true or absolute rates of biosynthesis or breakdown (i.e., accounts for turnover), and does not require total quantitative collection of breakdown products (i.e. metabolic derivatives and catabolic products). Furthermore, an ideal method would allow constant isotope levels in the precursor pool to be maintained for prolonged periods of time in a simple, non-demanding manner, for example, on the order of a few half-lives of long-lived molecules. However, there has not been a technique that has fulfilled these objectives. A method for measuring non-invasively the rates of synthesis or breakdown of biological molecules that are inaccessible or not easily accessible to direct sampling (e.g. molecules in or associated with tissues of the internal organs) and that is widely applicable, reliable, easy to perform, inexpensive, without toxicities or complications, applicable in human subjects, free of the need for medical supervision or in-patient procedures (such as intravenous infusions), does not require complex instructions, and possesses the advantages of simple interpretation, therefore would be extremely valuable and useful in fields ranging from medical diagnostics to drug discovery, genetics, functional genomics, and basic research.

BRIEF SUMMARY OF THE INVENTION

In order to meet these needs, the present invention is directed to a method of determining the rates of biosynthesis and breakdown of biological molecules that are inaccessible or not easily accessible to direct sampling, such as intracellular or extracellular molecules in the tissues of internal organs, in a non-invasive manner.

In one aspect, the present invention is directed to a method for determining the rate of biosynthesis or breakdown of one or more biological molecules in an individual comprising the steps of: administering an isotope-labeled precursor molecule to an individual for a period of time sufficient for the label of the isotope-labeled precursor molecule to become incorporated into the one or more biological molecules; obtaining one or more biological samples from an individual, wherein the one or more biological samples comprise one or more metabolic derivatives of said one or more biological molecules as resulting from in vivo metabolism of the biological molecules; and detecting the incorporation of the label in said one or more metabolic derivatives by mass spectrometry to determine said rate of biosynthesis or breakdown of the one or more biological molecules.

In another aspect, the present invention is directed to a method for determining the rate of biosynthesis or breakdown of one or more biological molecules in an individual comprising the steps of: administering an isotope-labeled precursor molecule to an individual for a period of time sufficient for the label of the isotope-labeled precursor molecule to become incorporated into the one or more inaccessible biological molecules; obtaining one or more accessible biological samples from an individual, wherein the one or more accessible biological samples comprise one or more metabolic derivatives of said one or more inaccessible biological molecules as resulting from in vivo metabolism of the inaccessible biological molecules; and detecting the incorporation of the label in said one or more metabolic derivatives by mass spectrometry to determine said rate of biosynthesis or breakdown of the one or more inaccessible biological molecules.

The detecting step may include calculating the isotope enrichment of the one or more inaccessible biological molecules by mass isotopomer distribution analysis (MIDA) and applying precursor-product or exponential decay equations to determine the rate of biosynthesis or breakdown of the inaccessible biological molecule.

The precursor molecules may be administered in vivo. In another variation, the isotopic label is selected from the group including $^2H$, $^3H$, $^{13}C$, $^{15}N$, $^{18}O$, $^3H$, $^{14}C$, $^{35}S$, $^{32}P$, $^{125}I$, and $^{131}I$. In a further variation, the label is $^2H$.

The precursor molecule may be water.

The method may include the additional step of partially purifying the one or more metabolic derivatives from the biological samples.

The isotope-labeled precursor molecule may be administered orally.

The method may include the additional step of degrading the one or more metabolic derivatives to form degraded metabolic derivatives. In further variation, the degraded metabolic derivatives are further separated by gas chromatography or HPLC.

The individual may be a human.

The metabolic derivatives may be catabolic products. In a further variation, the metabolic derivative derives primarily from the one or more biological molecules.

The label of the isotope-labeled precursor molecule is incorporated into the one or more metabolic derivatives biosynthetic incorporation into the one or more biological molecules followed by catabolic breakdown of the one or more biological molecules to form the one or more metabolic derivatives.

In another variation, the one or more metabolic derivatives cannot be utilized in the biosynthesis of another biological molecule in the individual.

In a further variation, biosynthesis or breakdown does not occur in the one or more biological samples.

The method may include the additional step of discontinuing the administering step.

The one or more biological molecules may be selected from the group including proteins, polynucleotides, lipids, glycosaminoglycans, prostoglycans, and carbohydrates.

The one or more biological molecules may be proteins. In further variation, the precursor molecule is an amino acid or one or more metabolic precursors of an amino acid. In further variation, label is incorporated post-translationally into the protein. In a still further variation, one or more metabolic derivatives is an amino acid or peptide.

The biological molecule may be collagen. In further variation, one or more metabolic derivatives may include one or more of the following collagen-specific metabolic derivatives: pyridinoline, deoxypyridinoline, hydroxyproline, hydroxylysine, glucosylgalactosyl-hydroxylysine, galactosylhydroxylysine, N-terminal telopeptide α1(I) (SEQ ID NO:1), N-terminal telopeptide α2(I) (SEQ ID NO:2), N-terminal telopeptide α2(I) (SEQ ID NO:3), N-terminal telopeptide α1(II) (SEQ ID NO:4), N-terminal telopeptide α1(III) (SEQ ID NO:5), C-terminal telopeptide α1(I) (SEQ ID NO:6), C-terminal telopeptide α2(I) (SEQ ID NO:7), C-terminal telopeptide α1(II) (SEQ ID NO:8), C-terminal telopeptide α1(II) (SEQ ID NO:9), C-terminal telopeptide α1(II) (SEQ ID NO: 10), C-terminal telopeptide α1(III) (SEQ ID NO: 11), cross-linked carboxy-terminal peptide of type I collagen (ICTP), PINP(α1) (SEQ ID NO:12), PICP(α1) (SEQ ID NO:13), PINP(α2) (SEQ ID NO:14), PICP(α2) (SEQ ID NO:15), PIINP(α1) (SEQ ID NO: 16), PIICP(α1) (SEQ ID NO: 17), PIIINP(α1) (SEQ ID NO: 18), PIIICP(α1) (SEQ ID NO:19), PIVNP(α1) (SEQ ID NO:20), PIVNP(α2) (SEQ ID NO:21), PIVNP(α2) (SEQ ID NO:22), PIVNP(α3) (SEQ ID NO:23), PIVNP(α4) (SEQ ID NO:24), PIVNP(α5) (SEQ ID NO:25), and PIVNP(α6) (SEQ ID NO:26). In a still further variation, the one or more metabolic derivatives are an N-terminal or C-terminal amino acid sequence specific to a type of collagen.

The biological molecule may be myosin. In a further variation, the metabolic derivative is 3-methylhistidine.

The protein may be Amyloid Precursor Protein (APP). In a further variation, the metabolic derivative may be an APP-specific metabolic derivative. In a further variation, the APP-specific metabolic derivative is amyloid-beta 1-40 (SEQ ID NO:27) or amyloid-beta 1-42 (SEQ ID NO:28), or APP C peptide.

The one or more metabolic derivatives may be a post-translationally modified amino acid or protein.

The metabolic derivative may be one or more of a phosphoryllated, methylated, hydroxylated, glycosylated, N-acetyl-glucosaminated, prenylated, palmitoylated, and gamma-carboxylated amino acids or peptides.

The biological molecule may be myelin basic protein. In further variation, the protein is brain myelin basic protein. In a still further variation, the metabolic derivative is myelin basic protein-like material.

The biological sample may be urine.

The one or more biological molecules may be a lipid. In another variation, the lipid is a brain membrane lipid. In a still further variation, the metabolic derivative is −24(s)-hydroxy-cholesterol.

The one or more biological molecules may be a polynucleotide. In a further variation, the polynucleotide is deoxyribonucleic acid (DNA). In a further variation, the label is introduced post-replication to the DNA. In an additional variation, the one or more metabolic derivatives is a nucleic acid with one or more nucleic acid residues. In yet another variation, the metabolic derivative is selected from the group including methyl-cytosine, a methylated base, 8-oxo-guanosine, an oxidatively modified base, deoxyribose, and ribose.

The one or more biological molecules may be a glycosaminoglycan or proteoglycan. In a further variation, one or more metabolic derivatives is one or more of hyaluronic acid disaccharide, hyaluronic acid polymers, N-acetyl glucosamine, N-acetyl-galactosamine, chondroitin-sulfate disaccharide, chondroitin-sulfate polymers, heparin sulfate disaccharide, and heparin sulfate disaccharide polymers.

The biological sample may be an accessible biological sample.

The precursor molecule may be administered repeatedly or continuously over a defined period of time.

The invention may be directed to a method of identifying a disease state by assessing the biosynthesis or breakdown rate, wherein the rate is indicative of a disease state. In another variation, the disease state is a physiological condition characterized by an alteration in the biosynthesis or breakdown rate of the one or more biological molecules. In another variation, the disease state or condition is one or more of osteoporosis, left-ventricular hypertrophy, liver cirrhosis, liver fibrosis, congestive heart failure, scleroderma, black-lung (coal-miner's pneumoconiosis), cardiac fibrosis, lung fibrosis, Alzheimer's disease, multiple sclerosis, rheumatoid arthritis, diabetes mellitus, muscle wasting syndromes, muscular dystrophies, athletic training, and cancer.

In another variation, the invention is directed to a method for monitoring a response of a disease state or a condition in an individual to a therapeutic intervention by assessing the rate of biosynthesis or breakdown, before the initiation of the therapeutic intervention; assessing the rate of biosynthesis or breakdown of the one or more biological molecules after the initiation of such therapeutic intervention; and comparing the rates of synthesis or breakdown before and after therapeutic intervention to monitor the response of a disease or a condition to therapeutic intervention. In another variation, the disease state or condition is one or more of osteoporosis, left-ventricular hypertrophy, liver cirrhosis, liver fibrosis, congestive heart failure, scleroderma, black-lung (coal-miner's pneumoconiosis), cardiac fibrosis, lung fibrosis, Alzheimer's disease, multiple sclerosis, rheumatoid arthritis, diabetes mellitus, muscle wasting syndromes, muscular dystrophies, athletic training, and cancer.

In a further variation, the invention may be directed to a method for determining a whole-body pool size of the one or more biological molecules in an individual by measuring the rate of biosynthesis of the biological molecule; measuring the biosynthesis rate of the one or more biological molecules; and dividing the daily excretion rate by the daily fractional replacement rate of the one or more metabolic derivatives to calculate whole-body pool size of the one or more biological molecules in the individual.

The invention also may be directed to a kit for determining the biosynthetic rate or breakdown rate of one or more biological molecules in an individual including an isotope-labeled precursor, and instructions for use of the kit, wherein the kit is used to determine the rate of biosynthesis or breakdown of the one or more biological molecules in the individual. In another variation, the kit may include chemical compounds for isolating the one or more metabolic derivatives from urine, bone, or muscle. In further variation, the kit may include a tool for administration of precursor molecules. The kit may also include an instrument for collecting a sample from the subject.

BRIEF DESCRIPTION OF THE FIGURES

In FIG. 3A, label (*) enters pool A (precursor pool) and pool B (product) is synthesized from A. The replacement rate constant (k) for pool B is revealed by the shape of the rise-to-plateau curve, as shown here for k=0.1, 0.5 and 1.0 $d^{-1}$. The plateau value of labeling reached in pool B will depend upon the fraction of B derived from the precursor pool. Examples of 50% (left) and 100% B (right) deriving from endogenous synthesis are shown.

FIG. 8B depicts a comparison of $^2H$ incorporation into galactose moiety of galactosyl-cerebroside in brain versus blood from a mouse maintained on 8% $^2H_2O$ in drinking water.

DETAILED DESCRIPTION OF THE INVENTION

Figure 1:
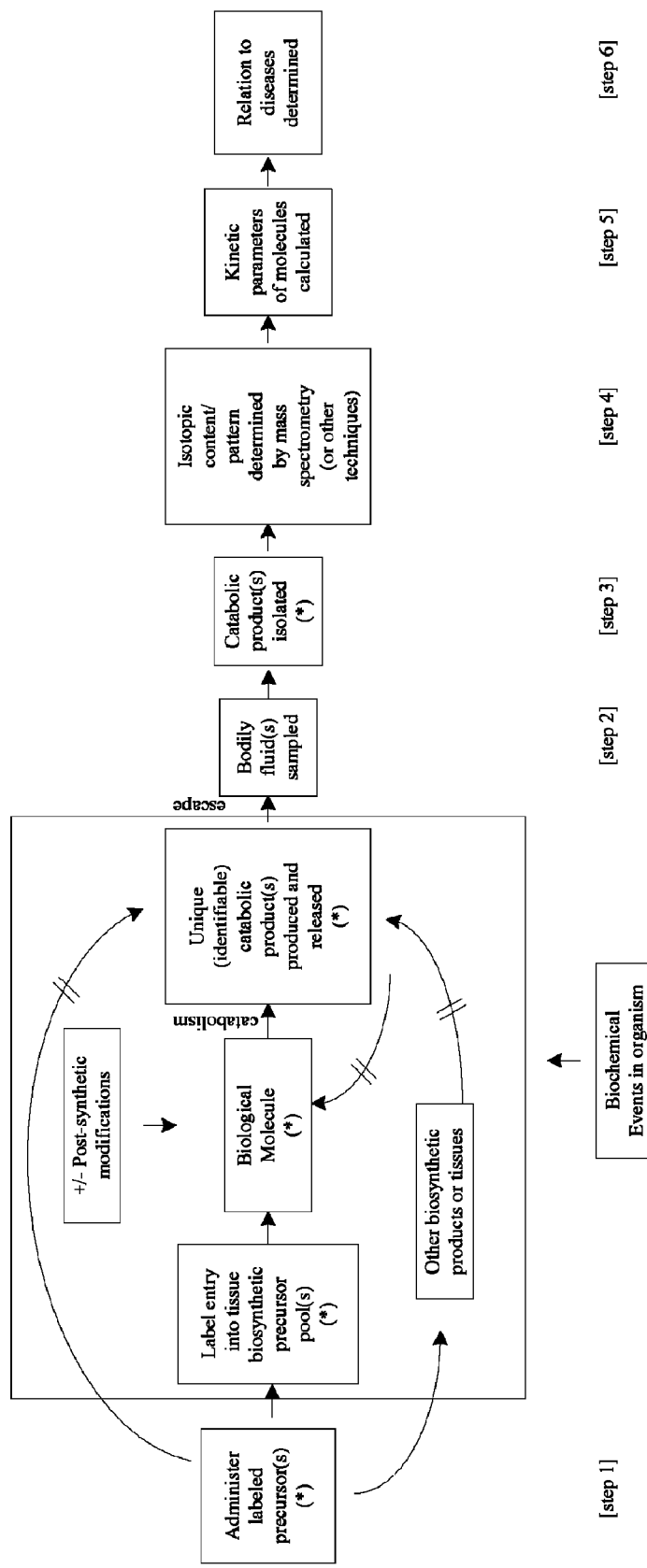
FIG. 1 is a flow chart of an embodiment of the invention.
Figure 2:
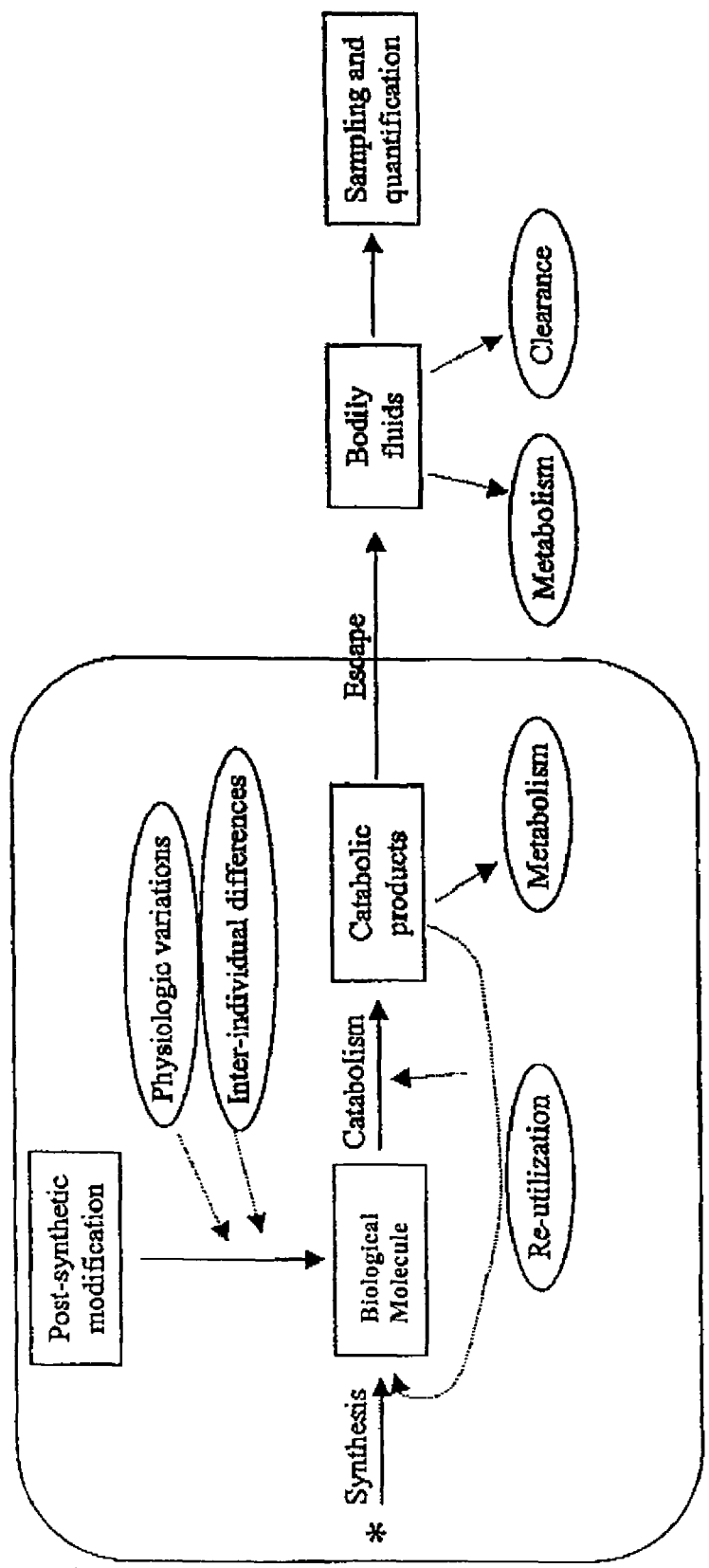
FIG. 2 summarizes schematically the advantages of the current invention over previous non-isotopic uses of post-synthetically modified metabolic derivatives to estimate turnover of tissue molecules. The circled items with broken-line arrows represent factors that could alter reliability or interpretability of previous methods.

Applicants have discovered an effective method for determining the rates of biosynthesis and/or breakdown of biological molecules in a non-invasive manner. In particular, applicants have discovered a method of determining the rates of biosynthesis and breakdown of biological molecules that are inaccessible or not easily accessible to direct sampling, such as intracellular or extracellular molecules in the tissues of internal organs, in a non-invasive manner.

I. General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989) Cold Spring Harbor Press; *Oligonucleotide Synthesis* (M. J. Gait, ed., 1984); *Methods in Molecular Biology, Humana Press; Cell Biology: A Laboratory Notebook* (J. E. Cellis, ed., 1998) Academic Press; *Animal Cell Culture* (R. I. Freshney, ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); and *Mass isotopomer distribution analysis at eight years: theoretical, analytic and experimental considerations* by Hellerstein and Neese (*Am J Physiol* 276 (*Endocrinol Metab.* 39) E1146-E1162, 1999). Furthermore, procedures employing commercially available assay kits and reagents will typically be used according to manufacturer-defined protocols unless otherwise noted.

II. Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, *Mass isotopomer distribution analysis at eight years: theoretical, analytic and experimental considerations* by Hellerstein and Neese (*Am J Physiol* 276 (*Endocrinol Metab.* 39) E1146-E1162, 1999). As appropriate, procedures involving the use of commercially available kits and reagents are generally carried out in accordance with manufacturer defined protocols and/or parameters unless otherwise noted.

"Isotopomers" refer to isotopic isomers or species that have identical elemental compositions but are constitutionally and/or stereochemically isomeric because of isotopic substitution, for example $CH_3NH_2$, $CH_3NHD$ and $CH_2DNH_2$.

"Isotopologues" refer to isotopic homologues or molecular species that have identical elemental and chemical compositions but differ in isotopic content (e.g., $CH_3NH_2$ vs. $CH_3NHD$ in the example above). Isotopologues are defined by their isotopic composition, therefore each isotopologue has a unique exact mass but may not have a unique structure. An isotopologue is usually comprised of a family of isotopic isomers (isotopomers) which differ by the location of the isotopes on the molecule (e.g., $CH_3NHD$ and $CH_2DNH_2$ are the same isotopologue but are different isotopomers).

"Mass isotopomer" refers to a family of isotopic isomers that are grouped on the basis of nominal mass rather than isotopic composition. A mass isotopomer may include molecules of different isotopic compositions, unlike an isotopologue (e.g., $CH_3NHD$, $^{13}CH_3NH_2$, $CH_3^{15}NH_2$ are part of the same mass isotopomer but are different isotopologues). In operational terms, a mass isotopomer is a family of isotopologues that are not resolved by a mass spectrometer. For quadrapole mass spectrometers, this typically means that mass isotopomers are families of isotopologues that share a nominal mass. Thus, the isotopologues $CH_3NH_2$ and $CH_3NHD$ differ in nominal mass and are distinguished as being different mass isotopomers, but the isotopologues $CH_3NHD$, $CH_2DNH_2$, $^{13}CH_3NH_2$, and $CH_3^{15}NH_2$ are all of the same nominal mass and hence are the same mass isotopomers. Each mass isotopomer is therefore typically composed of more than one isotopologue and has more than one exact mass. The distinction between isotopologues and mass isotopomers is useful in practice because all individual isotopologues are not resolved using quadrupole mass spectrometers and may not be resolved even using mass spectrometers that produce higher mass resolution, so that calculations from mass spectrometric data must be performed on the abundances of mass isotopomers rather than isotopologues. The mass isotopomer lowest in mass is represented as $M_0$; for most organic molecules, this is the species containing all $^{12}C$, $^1H$, $^{16}O$, $^{14}N$, etc. Other mass isotopomers are distinguished by their mass differences from $M_0$ ($M_1$, $M_2$, etc.). For a given mass isotopomer, the location or position of isotopes within the molecule is not specified and may vary (i.e., "positional isotopomers" are not distinguished).

"Mass isotopomer pattern" refers to a histogram of the abundances of the mass isotopomers of a molecule. Traditionally, the pattern is presented as percent relative abundances where all of the abundances are normalized to that of the most abundant mass isotopomer; the most abundant isotopomer is said to be 100%. The preferred form for applications involving probability analysis, however, is proportion or fractional abundance, where the fraction that each species contributes to the total abundance is used (see below). The term isotope pattern is sometimes used in place of mass isotopomer pattern, although technically the former term applies only to the abundance pattern of isotopes in an element.

A "monomer" refers to a chemical unit that combines during the synthesis of a polymer and which is present two or more times in the polymer.

A "polymer" refers to a molecule synthesized from and containing two or more repeats of a monomer.

A "peptide" is a sequence of two or more amino acids.

A "metabolic derivative" refers to any molecule produced from the biochemical conversion of one molecule into a related molecule by a reaction or series of reactions. A metabolic derivative in this context includes, but is not limited to, catabolic products as defined herein. It is understood that a metabolic derivative in this context includes, but is not limited to, any metabolic product deriving from a biological molecule including, but not limited to, metabolic products derived from amino acids, proteins, nucleic acids, lipids, carbohydrates, glycosaminoglycans, proteoglycans, porphyrins, and functional and non-functional fragments thereof.

A "catabolic product" refers to any compound that is produced as a result of catabolism. Catabolism generally refers to a process in which a molecule is broken into smaller parts, as opposed to anabolism in which molecules are synthesized from smaller subunits. Catabolic products are a subset of metabolic derivatives.

A "post-synthetic catabolite" (or "post-synthetic catabolic product") refers to a molecule or compound that has undergone the following biochemical sequence: 1) biosynthetic incorporation into an biological molecule; 2) catabolic breakdown of said biological molecule; 3) release from said biological molecule into an accessible biological sample or a biological fluid.

An "individual" is a vertebrate, preferably a mammal, more preferably a human.

A "isotope-labeled precursor molecule" refers to any molecule that contains an isotope of an element at levels above that found in natural abundance molecules.

As used herein, an individual "at risk" is an individual who is considered more likely to develop a disease state or a physiological state than an individual who is not at risk. An individual "at risk" may or may not have detectable symptoms indicative of the disease or physiological condition, and may or may not have displayed detectable disease prior to the treatment methods (e.g., therapeutic intervention) described herein. "At risk" denotes that an individual has one or more so-called risk factors. An individual having one or more of these risk factors has a higher probability of developing one or more disease(s) or physiological condition(s) than an individual without these risk factor(s). These risk factors can include, but are not limited to, history of family members developing one or more diseases, related conditions, or pathologies, history of previous disease, age, sex, race, diet, presence of precursor disease, genetic (i.e., hereditary) considerations, and environmental exposure.

"Labeled Water" includes water labeled with one or more specific heavy isotopes of either hydrogen or oxygen. Specific examples of labeled water include $^2H_2O$, $^3H_2O$, and $H_2^{18}O$.

"Partially purifying" refers to methods of removing one or more components of a mixture of other similar compounds. For example, "partially purifying a protein or peptide" refers to removing one or more proteins or peptides from a mixture of one or more proteins or peptides.

"Isolating" refers to separating one compound from a mixture of compounds. For example, "isolating a protein or peptide" refers to separating one specific protein or peptide from all other proteins or peptides in a mixture of one or more proteins or peptides.

An "accessible biological sample" encompasses a variety of sample types obtained from an individual through minimally invasive or non-invasive approaches (e.g., urine collection, blood drawing, needle aspiration, and other procedures involving minimal risk, discomfort or effort). The definition also includes samples that have been manipulated in any way after their procurement (through minimally invasive or non-invasive approaches), such as by treatment with reagents, solubilization, or enrichment for certain components, such as proteins or polynucleotides. The term "accessible biological sample" includes, but is not limited to, urine, blood, saliva, lacrimal fluid, inflammatory exudates, synovial fluid, abcess, empyema or other infected fluid, cerebrospinal fluid, sweat, pulmonary secretions (sputum), seminal fluid, and feces.

"Inaccessible biological sample" refers to biological samples that are not easily obtained through minimally invasive or non-invasive approaches. Inaccessible biological samples may be collected by invasive procedures, such as surgical excision, percutaneous biopsies, and post-mortem analysis. In particular, inaccessible biological samples include the internal organs (such as liver, heart, kidney, lung, pancreas, intestine, spleen, brain, bone marrow, skeletal muscle), the intracellular space of tissues of the internal organs, and the extracellular matrix of internal organs (such as bone, cartilage, joint space, ground substance, basement membrane, and vessel wall).

An "inaccessible biological molecule" refers to a biological molecule that cannot be easily acquired from or detectable in an accessible biological samples.

III. Methods of the Invention

The invention includes a method that allows measurement of biosynthesis and breakdown rates of a wide variety of biological molecules, including polymers of various classes, including, but not limited to proteins, lipids, carbohydrates, nucleic acids, glycosaminoglycans, and proteoglycans, which are important in biology and disease.

In one aspect, the invention includes a method for determining the rate of biosynthesis or breakdown of the biological molecule in an individual by detecting the incorporation of isotope label in metabolic derivatives of the biological molecule. The biological molecule may be any molecule including, but not limited to, proteins and peptides, polynucleotides (such as DNA and RNA), lipids (such as cholesterol), carbohydrates, glycosaminoglycans, proteoglycans, combinations or polymers thereof, or biological molecules in other chemical classes.

Preferably, the biological molecules are inaccessible biological molecules and/or are from inaccessible biological samples. The rate of biosynthesis or breakdown of the inaccessible biological molecules may be measured by measuring metabolic derivatives or catabolic products.

Moreover, the metabolic derivatives or catabolic products of the biological molecules are preferably in an accessible biological sample. The metabolic derivatives or catabolic products also preferably derive primarily, and optionally uniquely, from the biological molecule. Thus, the metabolic derivatives or catabolic products preferably identify or characterize, the biological molecule. Preferably, only small quantities, and not the total quantity, of metabolic derivatives or catabolic products need to be acquired. Further, the metabolic derivatives or catabolic products preferably cannot be re-incorporated into other biological molecules via metabolism.

A. Administering to an Individual an Isotope-Labeled Precursor Molecule

1. Labeled Precursor Molecules
a. Isotope Labels

As illustrated in FIG. 1, the first step in measuring biosynthesis, breakdown, and/or turnover rates involve administering an isotope-labeled precursor molecule to an individual. The isotope labeled precursor molecule may be a stable isotope or radioisotope. Isotope labels that can be used include, but are not limited to, $^2H$, $^3C$, $^{15}N$, $^{18}O$, $^3H$, $^{14}C$, $^{35}S$, $^{32}P$, $^{125}I$, $^{131}I$, or other isotopes of elements present in organic systems.

In one embodiment, the isotope label is $^2H$.

b. Precursor Molecules

The precursor molecule may be any molecule that is metabolized in the body to form a biological molecule. Isotope labels may be used to modify all precursor molecules disclosed herein to form isotope-labeled precursor molecules.

The entire precursor molecule may be incorporated into one or more biological molecules. Alternatively, a portion of the precursor molecule may be incorporated into one or more biological molecules.

Precursor molecules may include, but not limited to, $CO_2$, $NH_3$, glucose, lactate, $H_2O$, acetate, fatty acids.

i. Water as a Precursor Molecule

Water is a precursor of proteins, polynucleotides, lipids, carbohydrates, modifications or combinations thereof, and other biological molecules. As such, labeled water may serve as a precursor in the methods taught herein.

Labeled water may be readily obtained commercially. For example, $^2H_2O$ may be purchased from Cambridge Isotope Labs (Andover, Mass.), and $^3H_2O$ may be purchased, e.g., from New England Nuclear, Inc. In general, $^2H_2O$ is non-radioactive and thus, presents fewer toxicity concerns than radioactive $^3H_2O$. $^2H_2O$ may be administered, for example, as a percent of total body water, e.g., 1% of total body water consumed (e.g., for 3 liters water consumed per day, 30 microliters $^2H_2O$ is consumed). If $^3H_2O$ is utilized, then a non-toxic amount, which is readily determined by those of skill in the art, is administered.

Figure 3:
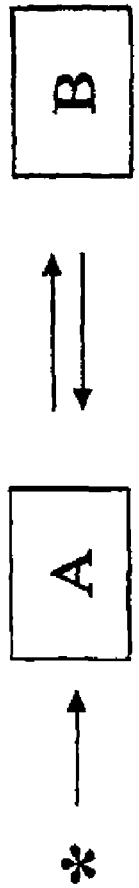
FIG. 3 shows the rise-to-plateau principle.
Figure 3:
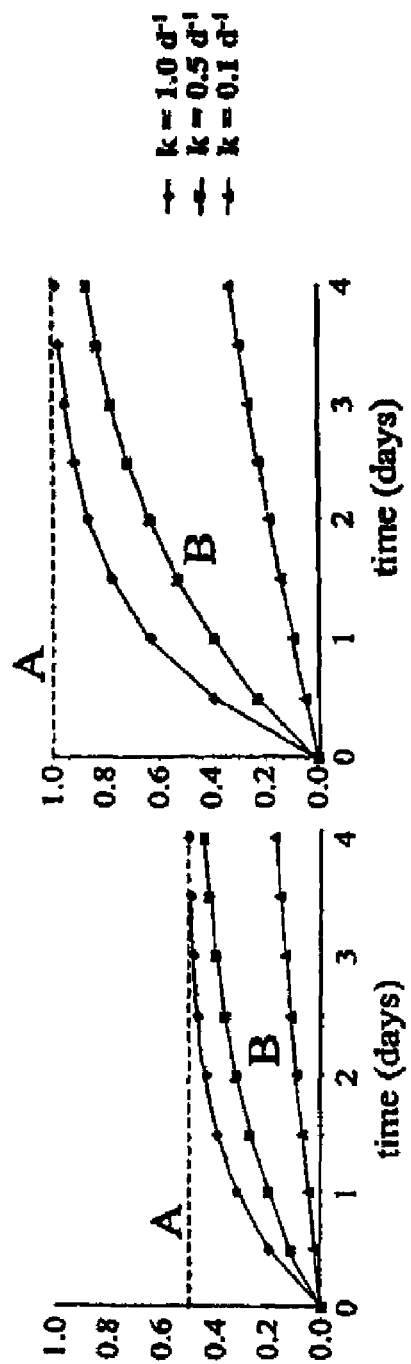
Figure 4:
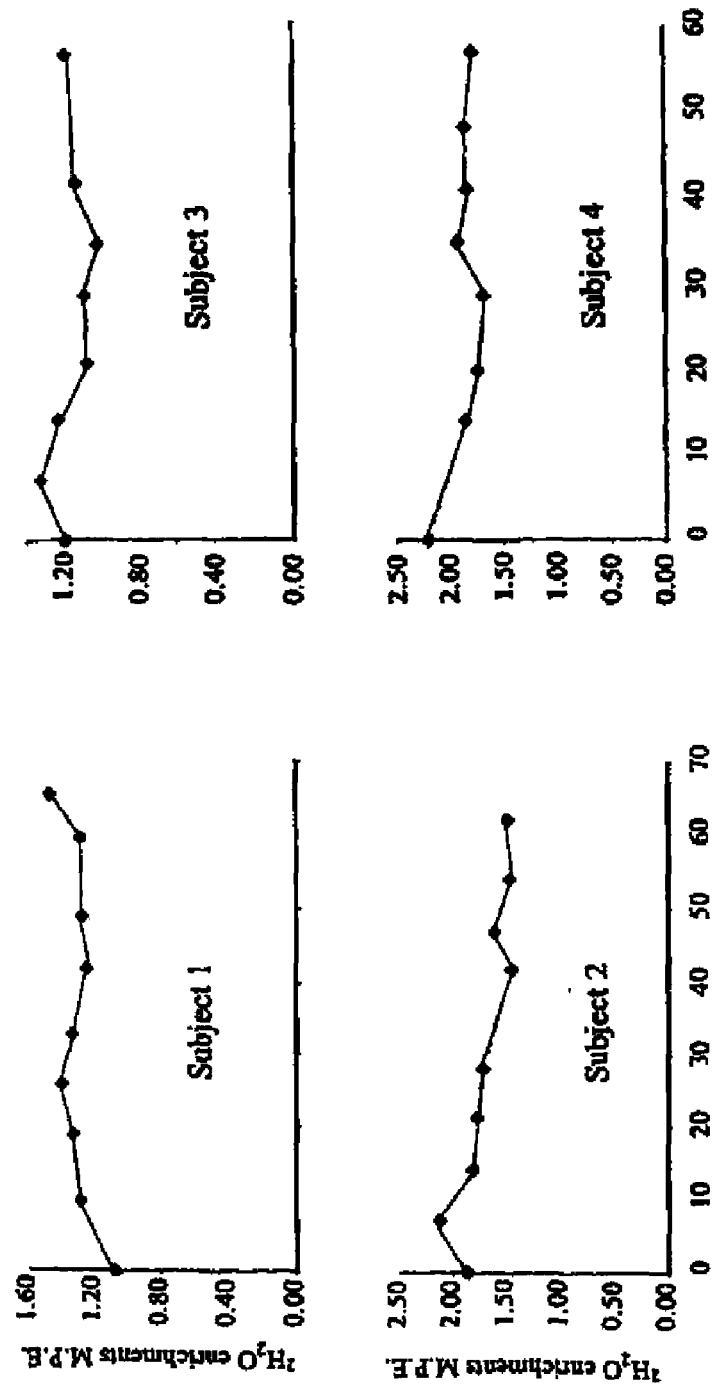
FIG. 4 depicts enrichments of $^2H_2O$ in body water of representative human subjects who drank 50-100 ml of $^2H_2O$ daily for 10-12 weeks. The data show that the precursor pool of body water is stable over a period of weeks for each subject.
Figure 5:
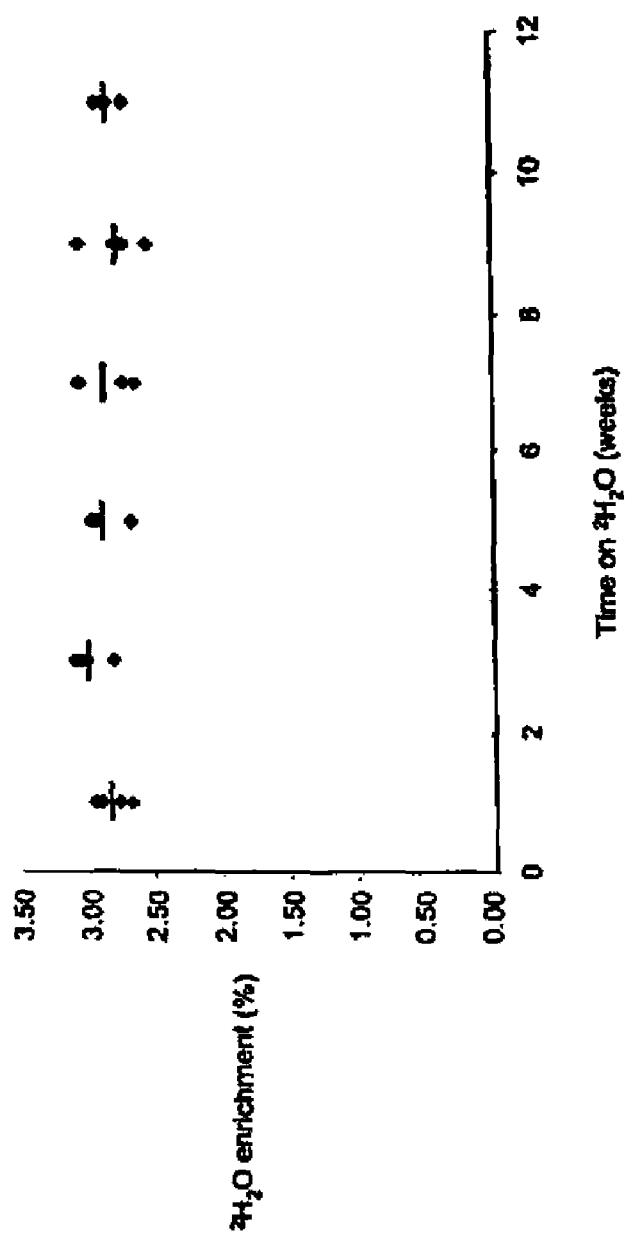
FIG. 5 depicts a time course of body $^2H_2O$ enrichments in rats maintained on 4% drinking water after baseline priming bolus to 2.5-3.0% body water enrichment.

Relatively high body water enrichments of $^2H_2O$ (e.g., 1-10% of the total body water is labeled) may be achieved using the techniques of the invention. This water enrichment is relatively constant and stable as these levels are maintained for weeks or months in humans and in experimental animals without any evidence of toxicity (FIGS. 3-5). This finding in a large number of human subjects (>100 people) is contrary to previous concerns about vestibular toxicities at high doses of $^2H_2O$. Applicants have discovered that as long as rapid changes in body water enrichment are prevented (e.g., by initial administration in small, divided doses), high body water enrichments of $^2H_2O$ can be maintained with no toxicities. For example, the low expense of commercially available $^2H_2O$ allows long-term maintenance of enrichments in the 1-5% range at relatively low expense (e.g., calculations reveal a lower cost for 2 months labeling at 2% $^2H_2O$ enrichment, and thus 7-8% enrichment in the alanine precursor pool (FIGS. 6A-B), than for 12 hours labeling of $^2H$-leucine at 10% free leucine enrichment, and thus 7-8% enrichment in leucine precursor pool for that period).

Figure 6A:
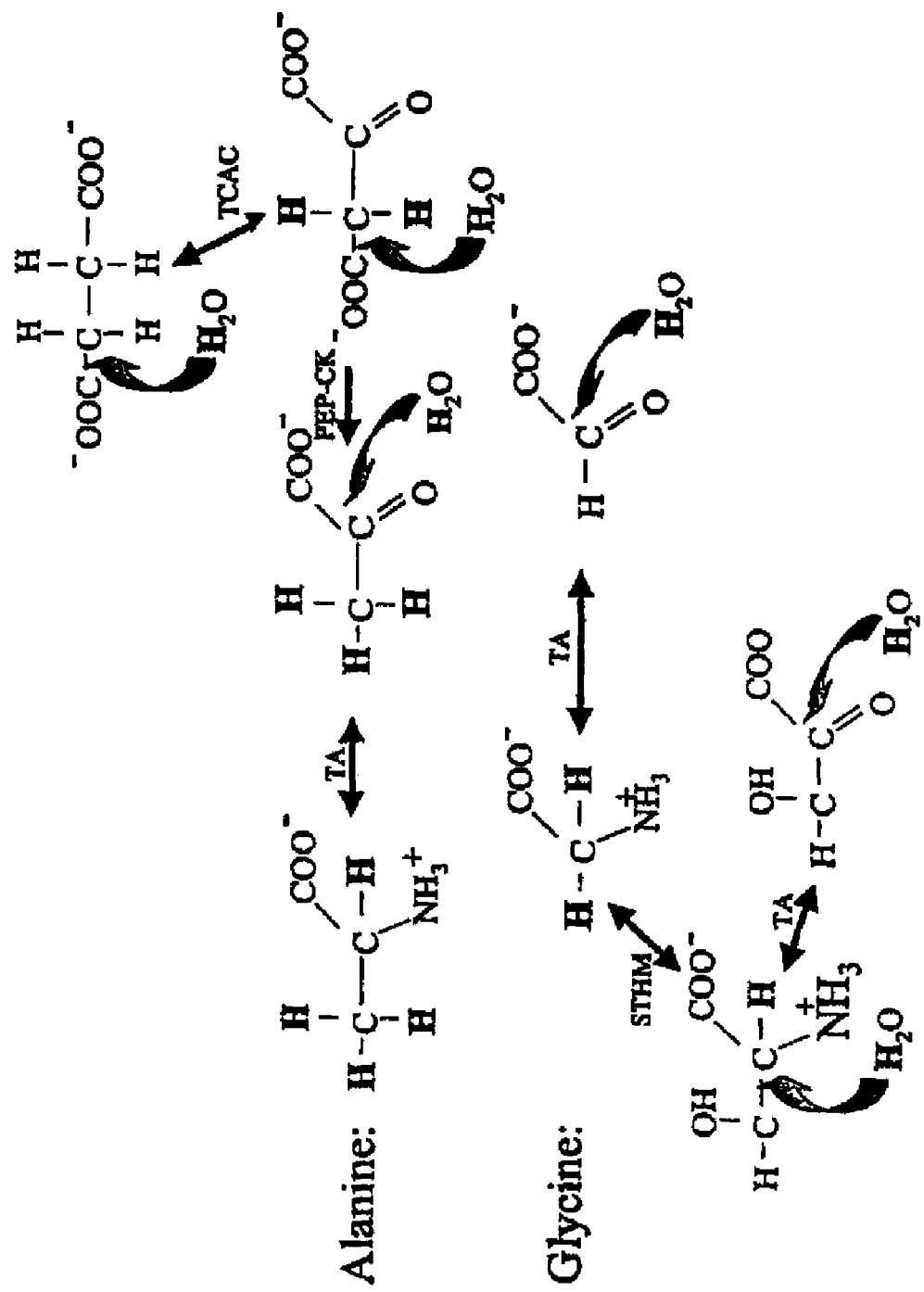
FIG. 6A-B depict pathways of labeled hydrogen exchange from labeled water into selected free amino acids. Two non-essential amino acids (alanine, glycine) and an essential amino acid (leucine) are shown, by way of example. Alanine and glycine are presented in FIG. 6A. Leucine is presented in FIG. 6B. Abbreviations: TA, transaminase; PEP-CK, phosphoenol-pyruvate carbokinase; TCAC, tricarboxylic acid cycle; STHM, serine tetrahydrofolate methyl transferase.
Figure 6B:
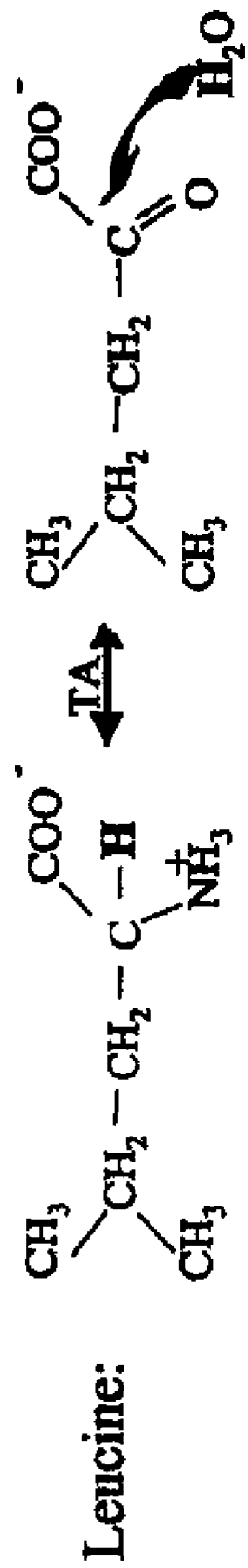
Figure 6C:
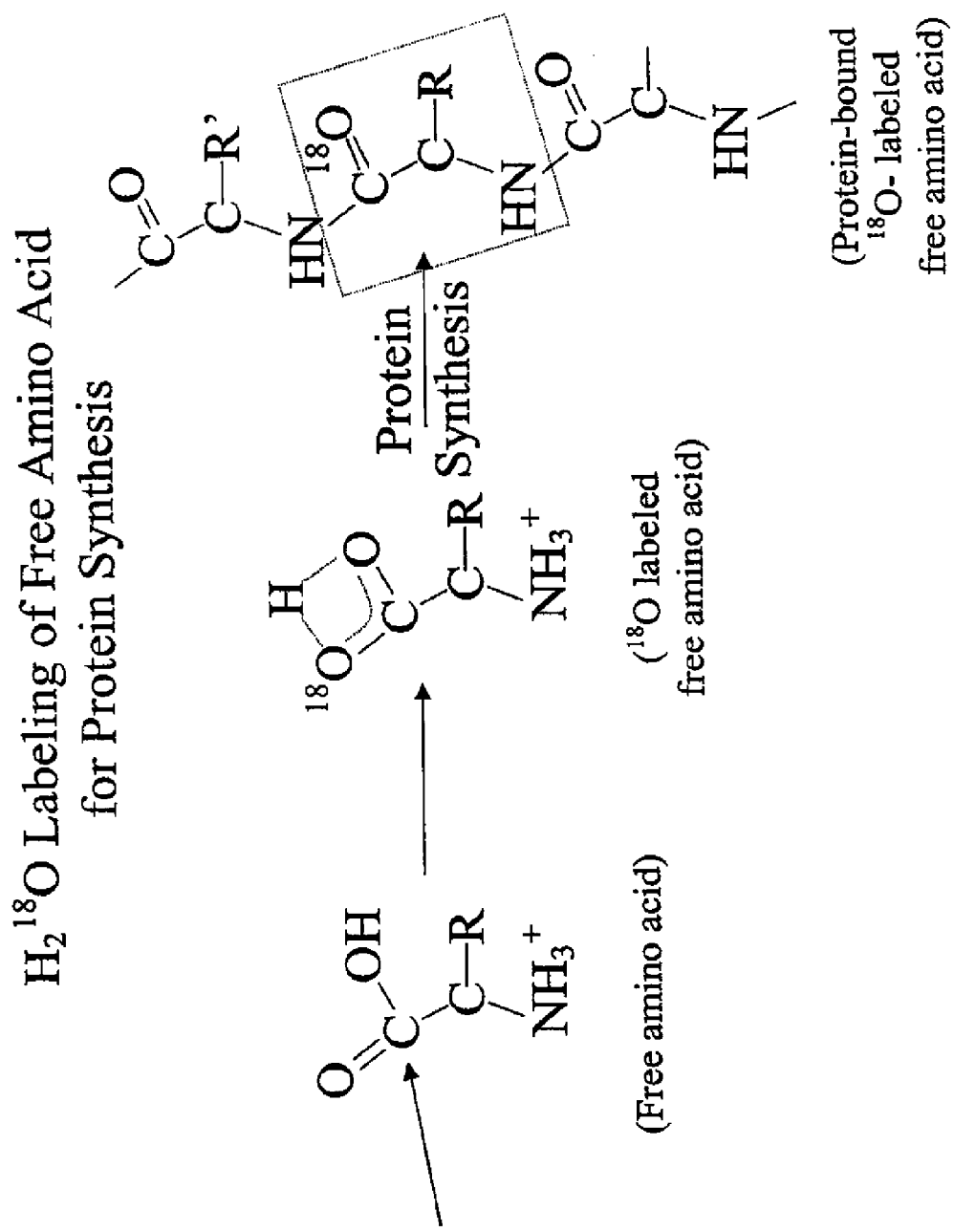
FIG. 6C depicts $H_2^{18}O$ labeling of free amino acids for protein synthesis.

Relatively high and relatively constant body water enrichments for administration of $H_2{}^{18}O$ may also be accomplished, since the $^{18}O$ isotope is not toxic, and does not present a significant health risk as a result (FIG. 6C).

Labeled water may be used as a near-universal precursor for most classes of biological molecules.

ii. Protein, Oligonucleotide, Lipid, and Carbohydrate Precursors

In another embodiment, precursor molecules are precursors of proteins, polynucleotides, lipids, and carbohydrates.

Precursors of Proteins

The precursor molecule may be any protein precursor molecule known in the art. These precursor molecules may be $CO_2$, $NH_3$, glucose, lactate, $H_2O$, acetate, and fatty acids.

Precursor molecules of proteins may also include one or more amino acids. The precursor may be any amino acid. The precursor molecule may be a singly or multiply deuterated amino acid. The precursor molecule is one or more of $^{13}C$-lysine, $^{15}N$-histidine, $^{13}C$-serine, $^{13}C$-glycine, $^2H$-leucine, $^{15}N$-glycine, $^{13}C$-leucine, $^2H_5$-histidine, and any deuterated amino acid. Labeled amino acids may be administered, for example, undiluted with non-deuterated amino acids. All isotope labeled precursors may be purchased commercially, for example, from Cambridge Isotope Labs (Andover, Mass.).

The precursor molecule may also include any precursor for post-translational or pre-translationally modified amino acids. These precursors include but are not limited to precursors of methylation such as glycine, serine or $H_2O$; precursors of hydroxylation, such as $H_2O$ or $O_2$; precursors of phosphoryllation, such as phosphate, $H_2O$ or $O_2$; precursors of prenylation, such as fatty acids, acetate, $H_2O$, ethanol, ketone bodies, glucose, or fructose; precursors of carboxylation, such as $CO_2$, $O_2$, $H_2O$, or glucose; precursors of acetylation, such as acetate, ethanol, glucose, fructose, lactate, alanine, $H_2O$, $CO_2$, or $O_2$; and other post-translational modifications known in the art.

The degree of labeling present in free amino acids may be determined experimentally, or may be assumed based on the number of labeling sites in an amino acid. For example, when using hydrogen isotopes as a label, the labeling present in C—H bonds of free amino acid or, more specifically, in tRNA-amino acids, during exposure to $^2H_2O$ in body water may be identified. The total number of C—H bonds in each non essential amino acid is known—e.g. 4 in alanine, 2 in glycine, etc.

The precursor molecule for proteins may be water. The hydrogen atoms on C—H bonds are the hydrogen atoms on amino acids that are useful for measuring protein synthesis from $^2H_2O$ since the O—H and N—H bonds of peptides and proteins are labile in aqueous solution. As such, the exchange of $^2H$-label from $^2H_2O$ into O—H or N—H bonds occurs without the synthesis of proteins from free amino acids as described above. C—H bonds undergo incorporation from $H_2O$ into free amino acids during specific enzyme-catalyzed intermediary metabolic reactions (FIG. 6). The presence of $^2H$-label in C—H bonds of protein-bound amino acids after $^2H_2O$ administration therefore means that the protein was assembled from amino acids that were in the free form during the period of $^2H_2O$ exposure—i.e. that the protein is newly synthesized. Analytically, the amino acid derivative used must contain all the C—H bonds but must remove all potentially contaminating N—H and O—H bonds.

Hydrogen atoms from body water may be incorporated into free amino acids. $^2H$ or $^3H$ from labeled water can enter into free amino acids in the cell through the reactions of intermediary metabolism, but $^2H$ or $^3H$ cannot enter into amino acids that are present in peptide bonds or that are bound to transfer RNA. Free essential amino acids may incorporate a single hydrogen atom from body water into the α-carbon C—H bond, through rapidly reversible transamination reactions (FIG. 6). Free non-essential amino acids contain a larger number of metabolically exchangeable C—H bonds, of course, and are therefore expected to exhibit higher isotopic enrichment values per molecule from $^2H_2O$ in newly synthesized proteins (FIGS. 6A-B).

One of skill in the art will recognize that labeled hydrogen atoms from body water may be incorporated into other amino acids via other biochemical pathways. For example, it is known in the art that hydrogen atoms from water may be incorporated into glutamate via synthesis of the precursor α-ketoglutarate in the citric acid cycle. Glutamate, in turn, is known to be the biochemical precursor for glutamine, proline, and arginine. By way of another example, hydrogen atoms from body water may be incorporated into post-translationally modified amino acids, such as the methyl group in 3-methyl-histine, the hydroxyl group in hydroxyproline or hydroxylysine, and others. Other amino acids synthesis pathways are known to those of skill in the art.

Oxygen atoms ($H_2{}^{18}O$) may also be incorporated into amino acids through enzyme-catalyzed reactions. For example, oxygen exchange into the carboxylic acid moiety of amino acids may occur during enzyme catalyzed reactions. Incorporation of labeled oxygen into amino acids is known to one of skill in the art as illustrated in FIG. 6C. Oxygen atoms may also be incorporated into amino acids from $^{18}O_2$ through enzyme catalyzed reactions (including hydroxyproline, hydroxylysine or other post-translationally modified amino acids).

Hydrogen and oxygen labels from labeled water may also be incorporated into amino acids through post-translational modifications. In one embodiment, the post-translational modification may already include labeled hydrogen or oxygen through biosynthetic pathways prior to post-translational modification. In another embodiment, the post-translational modification may incorporate labeled hydrogen, oxygen, carbon, or nitrogen from metabolic derivatives involved in the free exchange labeled hydrogens from body water, either before or after post-translational modification step (e.g. methylation, hydroxylation, phosphoryllation, prenylation, sulfation, carboxylation, acetylation or other known post-translational modifications).

Precursors of Polynucleotides

The precursor molecule may include components of polynucleotides. Polynucleotides include purine and pyrimidine bases and a ribose-phosphate backbone. The precursor molecule may be any polynucleotide precursor molecule known in the art.

The precursor molecules of polynucleotides may be $CO_2$, $NH_3$, urea, $O_2$, glucose, lactate, $H_2O$, acetate, ketone bodies and fatty acids, glycine, succinate or other amino acids, and phosphate.

Precursor molecules of polynucleotides may also include one or more nucleoside residues. The precursor molecules may also be one or more components of nucleoside residues. Glycine, aspartate, glutamine, and tetryhydrofolate, for example, may be used as precursor molecules of purine rings. Carbamyl phosphate and aspartate, for example, may be used as precursor molecules of pyrimidine rings. Adenine, adenosine, guanine, guanosine, cytidine, cytosine, thymine, or thymidine may be given as precursor molecules for deoxyribonucleosides. All isotope labeled precursors may be purchased commercially, for example, from Cambridge Isotope Labs (Andover, Mass.).

The precursor molecule of polynucleotides may be water. The hydrogen atoms on C—H bonds of polynucleotides, polynucleosides, and nucleotide or nucleoside precursors may be used to measure polynucleotide synthesis from $^2H_2O$. C—H bonds undergo exchange from $H_2O$ into polynucleotide precursors. The presence of $^2H$-label in C—H bonds of polynucleotides, nucleosides, and nucleotide or nucleoside precursors, after $^2H_2O$ administration therefore means that the polynucleotide was synthesized during this period. The degree of labeling present may be determined experimentally, or assumed based on the number of labeling sites in a polynucleotide or nucleoside.

Hydrogen atoms from body water may be incorporated into free nucleosides or polynucleotides. $^2H$ or $^3H$ from labeled water can enter these molecules through the reactions of intermediary metabolism.

One of skill in the art will recognize that labeled hydrogen atoms from body water may be incorporated into other polynucleotides, nucleotides, or nucleosides via various biochemical pathways. For example, glycine, aspartate, glutamine, and tetryhydrofolate, which are known precursors molecules of purine rings. Carbamyl phosphate and aspartate, for example, are known precursor molecules of pyrimidine rings. Ribose and ribose phosphate, and their synthesis pathways, are known precursors of polynucleotide synthesis.

Oxygen atoms ($H_2{}^{18}O$) may also be incorporated into polynucleotides, nucleotides, or nucleosides through enzyme-catalyzed biochemical reactions, including those listed above. Oxygen atoms from $^{18}O_2$ may also be incorporated into nucleotides by oxidative reactions, including non-enzymatic oxidation reactions (including oxidative damage, such as formation of 8-oxo-guanine and other oxidized bases or nucleotides).

Isotope-labeled precursors may also be incorporated into polynucleotides, nucleotides, or nucleosides in post-replication modifications. Post-replication modifications include modifications that occur after synthesis of DNA molecules. The metabolic derivatives may be methylated bases, including, but not limited to, methylated cytosine. The metabolic derivatives may also be oxidatively modified bases, including, but not limited to, 8-oxo-guanosine. Those of skill in the art will readily appreciate that the label may be incorporated during synthesis of the modification.

Precursors of Lipids

Labeled precursors of lipids may include any precursor in lipid biosynthesis.

The precursor molecules of lipids may be $CO_2$, $NH_3$, glucose, lactate, $H_2O$, acetate, and fatty acids.

The precursor may also include labeled water, preferably $^2H_2O$ (deuterated water), which is a precursor for fatty acids, glycerol moiety of acyl-glycerols, cholesterol and its derivatives; $^{13}C$ or $^2H$-labeled fatty acids, which are precursors for triglycerides, phospholipids, cholesterol ester, coamides and other lipids; $^{13}C$— or $^2H$-acetate, which is a precursor for fatty acids and cholesterol; $^{18}O_2$, which is a precursor for fatty acids, cholesterol, acyl-glycerides, and certain oxidatively modified fatty acids (such as peroxides) by either enzymatically catalyzed reactions or by non-enzymatic oxidative damage (e.g. to fatty acids); $^{13}C$— or $^2H$-glycerol, which is a precursor for acyl-glycerides; $^{13}C$— or $^2H$-labeled acetate, ethanol, ketone bodies or fatty acids, which are precursors for endogenously synthesized fatty acids, cholesterol and acylglycerides; and $^2H$ or $^{13}C$-labeled cholesterol or its derivatives (including bile acids and steroid hormones). All isotope labeled precursors may be purchased commercially, for example, from Cambridge Isotope Labs (Andover, Mass.).

Complex lipids, such as glycolipids and cerebrosides, can also be labeled from precursors, including $^2H_2O$, which is a precursor for the sugar-moiety of cerebrosides (including, but not limited to, N-acetylgalactosamine, N-acetylglucosamine-sulfate, glucuronic acid, and glucuronic acid-sulfate), the fatty acyl-moiety of cerebrosides and the sphingosine moiety of cerebrosides; $^2H$- or $^{13}C$-labeled fatty acids, which are precursors for the fatty acyl moiety of cerebrosides, glycolipids and other derivatives.

The precursor molecule may be or include components of lipids.

Precursors of Glycosaminoglycans and Proteoglycans

Glycosaminoglycans and proteoglycans are a complex class of biomolecules that play important roles in the extracellular space (e.g. cartilage, ground substance, and synovial joint fluid). Molecules in these classes include, for example, the large polymers built from glycosaminoglycans disaccharides, such as hyaluronan, which is a polymer composed of up to 50,000 repeating units of hyaluronic acid (HA) disaccharide, a dimer that contains N-acetyl-glucosamine linked to glucuronic acid; chondroitin-sulfate (CS) polymers, which are built from repeating units of CS disaccharide, a dimer that contains N-acetyl-galactosamine-sulfate linked to glucuronic acid, heparan-sulfate polymers, which are built from repeating units of heparan-sulfate, a dimer of N-acetyl (or N-sulfo)-glucosamine-sulfate linked to glucuronic acid; and keratan-sulfate polymers, which are built from repeating units of keratan-sulfate disaccharide, a dimer that contains N-acetyl-glucosamine-sulfate liked to galactose. Proteoglycans contain additional proteins that are bound to a central hyaluronan in polymer and other glycosaminoglycans, such as CS, that branch off of the central hyaluronan chain.

Labeled precursors of glycosaminoglycans and proteoglycans include, but are not limited to, $^2H_2O$ (incorporated into the sugar moieties, including N-acetylglucosamine, N-acetylgalactosamine, glucuronic acid, the various sulfates of N-acetylglucosamine and N-acetylgalactosamine, galactose, iduronic acid, and others), $^{13}C$— or $^2H$-glucose (incorporated into said sugar moieties), $^2H$- or $^{13}C$-fructose (incorporated into said sugar moieties), $^2H$- or $^{13}C$-galactose (incorporated into said sugar moieties), $^{15}N$-glycine, other $^{15}N$-labeled amino acids, or $^{15}N$-urea (incorporated into the nitrogen-moiety of said amino sugars, such as N-acetylglycosamine, N-acetyl-galactosamine, etc.); $^{13}C$- or $^2H$-fatty acids, $^{13}C$- or $^2H$-ketone bodies, $^{13}C$-glucose, $^{13}C$-fructose, $^{18}O_2$, $^{13}C$- or $^2H$-acetate (incorporated into the acetyl moiety of N-acetyl-sugars, such as N-acetyl-glucosamine or N-acetyl-galactosamine), and $^{18}O$ or $^{35}S$-labeled sulfate (incorporated into the sulfate moiety of chondroitin-sulfate, heparan-sulfate, keratan-sulfate, and other sulfate moieties). All isotope labeled precursors may be purchased commercially, for example, from Cambridge Isotope Labs (Andover, Mass.).

Precursors of Carbohydrates

Labeled precursors of carbohydrates may include any precursor of carbohydrate biosynthesis known in the art. These precursor molecules include but are not limited to $H_2O$, monosaccharides (including glucose, galactose, mannose, fucose, glucuronic acid, glucosamine and its derivatives, galactosamine and its derivatives, iduronic acid, fructose, ribose, deoxyribose, sialic acid, erythrose, sorbitol, adols, and polyols), fatty acids, acetate, ketone bodies, ethanol, lactate, alanine, serine, glutamine and other glucogenic amino acids, glycerol, $O_2$, $CO_2$, urea, starches, disaccharides (including sucrose, lactose, and others), glucose polymers and other polymers of said monosaccharides (including complex polysaccharides).

The precursor molecule may include labeled water, preferably $^2H_2O$, which is a precursor to said monosaccharides, $^{13}C$-labeled glucogenic precursors (including glycerol, $CO_2$, glucogenic amino acids, lactate, ethanol, acetate, ketone bodies and fatty acids), $^{13}C$- or $^2H$-labeled said monosaccharides, $^{13}C$- or $^2H$-labeled starches or disaccharides; other components of carbohydrates labeled with $^2H$ or $^{13}C$; and $^{18}O_2$, which is a precursor to monosaccharides and complex polysaccharides.

3. Methods of Administering Labeled Precursor Molecules

Labeled precursors can be administered to an individual by various in vivo methods including, but not limited to, orally, parenterally, subcutaneously, intravenously, and intraperitoneally.

The individual may be an animal. The individual also may be human.

By way of example, in one embodiment, the labeled precursor is $^2H_2O$ that can be ingested (e.g., by drinking or intravenous infusion) by an individual. In another embodiment, the labeled precursor is $^{13}C_1$-lysine that can be ingested (e.g., by drinking or intravenous infusion) by an individual. In another embodiment, the labeled precursor is $^{13}C_1$-glycine that can be ingested (e.g., by drinking or intravenous infusion) by an individual. In another embodiment, the labeled precursor is $^2H_3$-leucine that can be ingested (e.g., by drinking or intravenous infusion) by an individual. In another embodiment, the labeled precursor is $^2H_2$-glucose that can be ingested (e.g. by drinking or intravenous infusion) by an individual.

The length of time for which the labeled precursor is administered may be sufficient to allow the precursor molecule to become incorporated into a biosynthetic pathway. The isotope-labeled precursor molecule also may be introduced to an individual for a period of time sufficient for the label of said isotope-labeled precursor molecule to become incorporated into one or more biological molecules and then released in the form of one or more labeled and unlabeled metabolic derivatives of the one or more biological molecules. The period of time may be a pre-determined length of time. This required duration of time may range from minutes or hours (e.g., for fast turnover biological molecules), to weeks or even months (e.g., for slow-turnover biological molecules).

Figure 7:
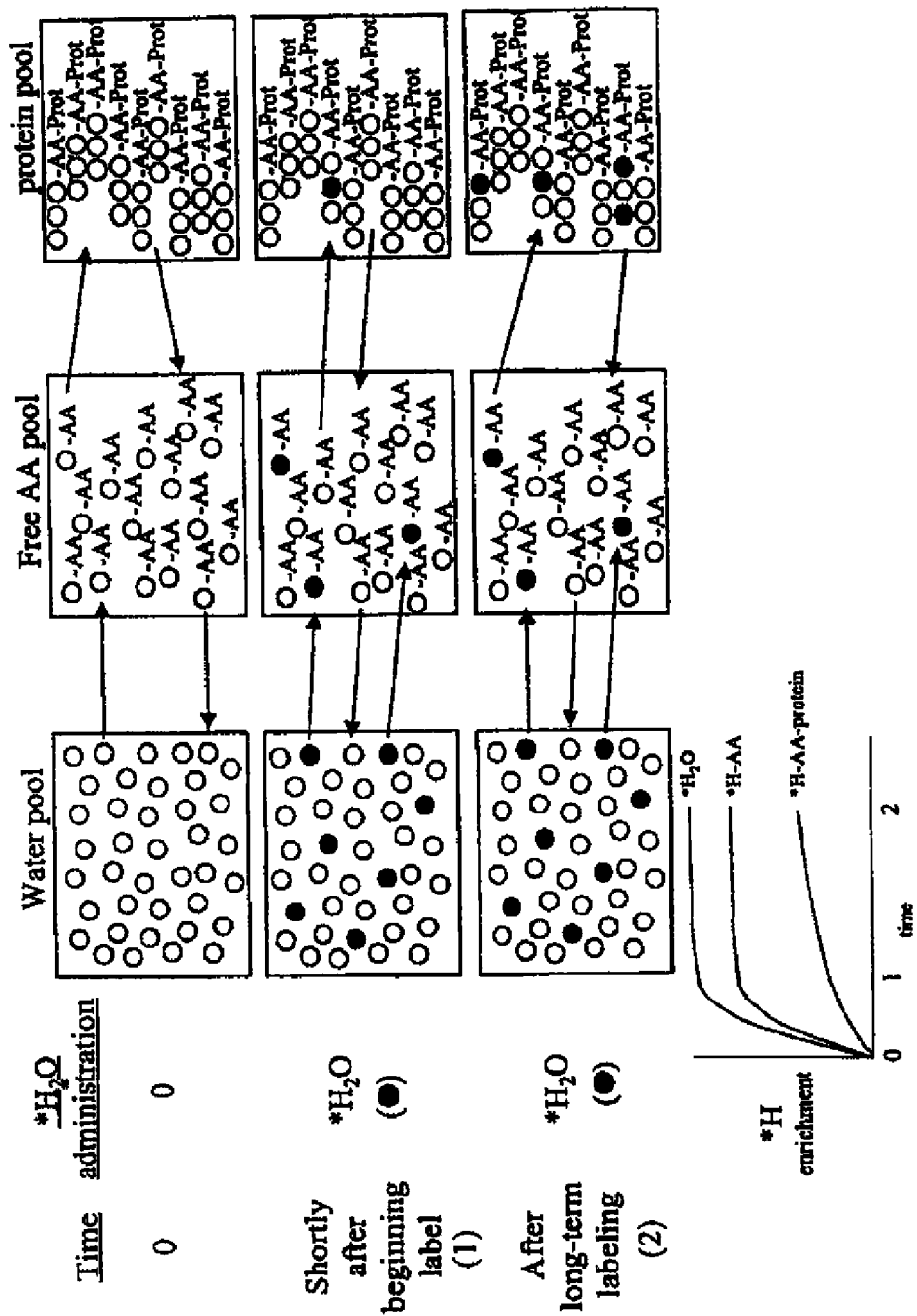
FIG. 7 depicts a schematic model for measurement of new protein synthesis from the incorporation of hydrogen-labeled $H_2O$ (*H) into protein-bound amino acids. Labeled hydrogens are represented by closed circles; unlabeled by open circles. The expected time course of labeling each compartment (body water, free amino acids, protein-bound amino acids) is shown in the inset.

The precursor molecule may be continuously or repeatedly administered. Administration of the precursor can be achieved in various ways. The precursor molecule may be administered continuously or repeatedly, so that a sufficient amount of precursor is administered such that an isotopic plateau value of maximal or isotopic enrichment is approached (i.e. wherein the concentration of labeled precursor is relatively constant over time). For example, see FIG. 7. If the continuous labeling period can be maintained for as long as 4-5 half-lives of a biological molecule, the asymptote reached and the shape of the isotope enrichment curve approaching this asymptote will reveal the "true precursor" isotopic enrichment as well as the fractional replacement rate of the biological molecule product (FIG. 7). By labeling to plateau while maintaining a stable precursor pool enrichment, it is thereby possible to overcome the biological complexities of cellular metabolite pools.

The precursor molecule may be administered discontinuously. For the discontinuous labeling method, an amount of labeled precursor molecule is measured and then administered, one or more times, and then the exposure to labeled precursor molecule is discontinued and wash-out of labeled precursor molecule from body precursor pool is allowed to occur. The time course of biological molecule breakdown may then be monitored by measurement of the loss of label or decay of label incorporation (dilution or die-away) in the metabolic derivative of the biological sample.

B. Biological Molecules and Metabolic Derivatives

In one aspect, the invention includes a method for determining the rate of synthesis or breakdown of a biological molecule in an individual by detecting the incorporation of isotope label in metabolic derivatives of the biological molecule.

Preferably, the biological molecules are inaccessible biological molecules or are found in inaccessible biological samples. The rate of biosynthesis or breakdown of the inaccessible biological molecules may be measured by measuring isotope labeling or decay in metabolic derivatives or catabolic products.

Moreover, the metabolic derivatives or catabolic products of the biological molecules are preferably in an accessible biological sample. The metabolic derivatives or catabolic products also preferably derive primarily, and optionally uniquely, from the biological molecule. Thus, the metabolic derivatives or catabolic products preferably identify or characterize, the biological molecule, and are thus said to be identifiers of the biological molecule. Preferably, only small quantities, and not the total quantity, of metabolic derivatives or catabolic products need to be acquired. Further, the metabolic derivatives or catabolic products preferably cannot be re-incorporated into other biological molecules via metabolism.

Representative precursor molecules, inaccessible biological molecules, and metabolic derivatives are depicted in Table 1. The precursor molecule may be incorporated via biosynthesis into a biological molecule and subsequent breakdown to form one or more metabolic derivatives. Metabolic derivatives incorporating the label may then be correlated to the biological molecule from which they were derived, and the label incorporation or decay kinetics in the metabolic derivative may reveal the label incorporation or decay kinetics in the biological molecule from which they were derived.

TABLE 1

Precursors, Inaccessible Molecules, and Metabolic Derivatives

| Precursor Molecule | Inaccessible Biological Molecule | Metabolic Derivatives |
|---|---|---|
| $^{13}$C-lysine<br>$^{15}$N-histidine<br>$^{13}$C-serine<br>$^{13}$C-glycine<br>$^{2}$H$_5$-histidine<br>Other deuterated, $^{15}$N-labeled or<br>$^{13}$C-labeled amino acids<br>Labeled Water<br>$^{18}$O$_2$ | Bone Collagen | Pyridinoline<br>Hydroxy-pyridinoline<br>N- and C-terminal telopeptides<br>and propeptides<br>4-hydroxyproline<br>3-hydroxyproline<br>hydroxylysine<br>glucosylgalactosyl-<br>hydroxylysine<br>galactosylhydroxylysine |
| $^{13}$C-lysine<br>$^{15}$N-histidine<br>$^{13}$C-serine<br>$^{13}$C-glycine<br>$^{2}$H$_5$-histidine<br>Other deuterated, $^{15}$N-labeled or<br>$^{13}$C-labeled amino acids<br>Labeled Water<br>$^{18}$O$_2$ | Cardiac Collagen | Pyridinoline<br>Hydroxy-pyridinoline<br>N- and C-terminal telopeptides<br>and propeptides<br>4-hydroxyproline<br>3-hydroxyproline<br>hydroxylysine<br>glucosylgalactosyl-<br>hydroxylysine<br>galactosylhydroxylysine |
| $^{13}$C-lysine<br>$^{15}$N-histidine<br>$^{13}$C-serine<br>$^{13}$C-glycine<br>$^{2}$H$_5$-histidine<br>Other deuterated, $^{15}$N-labeled or<br>$^{13}$C-labeled amino acids<br>Labeled Water<br>$^{18}$O$_2$ | Liver Collagen | Pyridinoline<br>Hydroxy-pyridinoline<br>N- and C-terminal telopeptides<br>and propeptides<br>4-hydroxyproline<br>3-hydroxyproline<br>hydroxylysine<br>glucosylgalactosyl-<br>hydroxylysine<br>galactosylhydroxylysine |
| $^{13}$C-lysine<br>$^{15}$N-histidine<br>$^{13}$C-serine<br>$^{13}$C-glycine<br>$^{2}$H$_5$-histidine<br>Other deuterated, $^{15}$N-labeled or<br>$^{13}$C-labeled amino acids<br>Labeled Water<br>$^{18}$O$_2$ | Lung Collagen | Pyridinoline<br>Hydroxy-pyridinoline<br>N- and C-terminal telopeptides<br>and propeptides<br>4-hydroxyproline<br>3-hydroxyproline<br>hydroxylysine<br>glucosylgalactosyl-<br>hydroxylysine<br>galactosylhydroxylysine |
| $^{13}$C-lysine<br>$^{15}$N-histidine<br>$^{13}$C-serine<br>$^{13}$C-glycine<br>$^{2}$H$_5$-histidine<br>Other deuterated, $^{15}$N-labeled or<br>$^{13}$C-labeled amino acids<br>Labeled Water<br>$^{18}$O$_2$ | Skin Collagen | Pyridinoline<br>Hydroxy-pyridinoline<br>N- and C-terminal telopeptides<br>and propeptides<br>4-hydroxyproline<br>3-hydroxyproline<br>hydroxylysine<br>glucosylgalactosyl-<br>hydroxylysine<br>galactosylhydroxylysine |
| $^{13}$C-lysine<br>$^{15}$N-histidine<br>$^{13}$C-serine<br>$^{13}$C-glycine<br>$^{2}$H$_5$-histidine<br>Other deuterated, $^{15}$N-labeled or<br>$^{13}$C-labeled amino acids<br>Labeled Water<br>$^{18}$O$_2$ | Brain Amyloid Precursor Protein, Brain Amyloid Fibrils | A-beta (1-40) (SEQ ID NO: 27)<br>A-beta (1-42) (SEQ ID NO: 28)<br>Amyloid precursor protein C-peptide |
| $^{13}$C-lysine<br>$^{15}$N-histidine<br>$^{13}$C-histidine<br>$^{13}$C-serine<br>$^{13}$C-glycine<br>$^{2}$H$_5$-histidine<br>Other deuterated, $^{15}$N-labeled or<br>$^{13}$C-labeled amino acids<br>Labeled Water<br>$^{18}$O$_2$ | Muscle Myosin | 3-methyl-histidine<br>Peptides from myosin or actin |

TABLE 1-continued

Precursors, Inaccessible Molecules, and Metabolic Derivatives

| Precursor Molecule | Inaccessible Biological Molecule | Metabolic Derivatives |
| --- | --- | --- |
| $^{13}$C-lysine<br>$^{15}$N-histidine<br>$^{13}$C-serine<br>$^{13}$C-glycine<br>$^{2}$H$_5$-histidine<br>Other deuterated, $^{15}$N-labeled or $^{13}$C-labeled amino acids<br>Labeled Water | Myelin basic protein(MBP) | Brain MBP-like material |
| $^{15}$N-histidine<br>$^{13}$C-lysine<br>$^{13}$C-serine<br>$^{13}$C-glycine<br>$^{2}$H$_5$-histidine<br>Other deuterated, $^{15}$N-labeled or $^{13}$C-labeled amino acids<br>Labeled Water | Prostate-specific antigen (PSA)<br>Prostate-specific membrane antigen (PSMA) | Peptides from PSA or PSMA |
| $^{13}$C-lysine<br>$^{15}$N-histidine<br>$^{2}$H$_5$-histidine<br>Other deuterated, $^{15}$N-labeled or $^{13}$C-labeled amino acids<br>Labeled water | Polynucleotides (DNA or RNA), methylated or oxidized nucleotides | Deoxycytosine<br>methyl-deoxycytosine<br>8-oxo-guanine<br>Ribose<br>Deoxyribose |
| Labeled water<br>$^{13}$C-Acetate or $^{13}$C-ethanol<br>$^{2}$H- or $^{13}$C-fatty acids<br>$^{2}$H- or $^{13}$C-ketone bodies<br>$^{18}$O$_2$<br>$^{2}$H- or $^{13}$C-labeled cholesterol | Brain membrane cholesterol | 24-(S)-hydroxycholesterol |
| Labeled Water<br>$^{18}$O$_2$<br>$^{13}$C-acetate<br>$^{2}$H- or $^{13}$C-glucose<br>$^{2}$H- or $^{13}$C-galactose<br>$^{13}$C-serine<br>$^{2}$H or $^{13}$C-fatty acids<br>$^{13}$C-alanine<br>$^{13}$C-lactate | Brain myelin lipids | Galactosyl-cereboside<br>Sphingomyelin<br>Sphingosines |
| Labeled Water<br>$^{18}$O$_2$<br>$^{13}$C-acetate<br>$^{2}$H- or $^{13}$C-glucose<br>$^{2}$H- or $^{13}$C-galactose<br>$^{13}$C-serine<br>$^{2}$H or $^{13}$C-fatty acids | Pancreatic β-cell membrane lipids | Circulating β-cell specific membrane lipids |
| $^{13}$C-lysine<br>$^{15}$N-histidine<br>$^{2}$H$_5$-histidine<br>Other deuterated, $^{15}$N-labeled or $^{13}$C-labeled amino acids<br>Labeled Water<br>$^{18}$O$_2$ | Pancreatic β-cell proteins | Insulin<br>C-peptide<br>Islet amyloid protein |
| Labeled Water<br>$^{13}$C-acetate or $^{13}$C-ethanol<br>$^{2}$H- or $^{13}$C-fatty acids<br>$^{2}$H- or $^{13}$C-ketone bodies<br>$^{18}$O$_2$<br>$^{2}$H- or $^{13}$C-labeled cholesterol | Tissue cholesterol (hepatic, adrenal, ovarian, testicular) | Bile acids<br>Steroid hormones |
| Labeled water<br>$^{2}$H- or $^{13}$C-glucose<br>$^{2}$H- or $^{13}$C-galactose<br>$^{2}$H- or $^{13}$C-glucosamine<br>$^{13}$C-alanine<br>$^{13}$C-lactate | Synovial fluid hyaluronan, glycosaminoglycans, or proteoglycans | Hyaluronic acid disaccharide or polymers; N-acetyl glucosamine, N-acetyl-galactosamine, chondroitin-sulfate disaccharide or polymers; Heparin sulfate disaccharide or polymers |
| Labeled water<br>$^{2}$H- or $^{13}$C-glucose<br>$^{2}$H- or $^{13}$C-galactose<br>$^{2}$H- or $^{13}$C-glucosamine<br>$^{13}$C-alanine<br>$^{13}$C-lactate | Cartilage hyaluronan, glycosminoglycans, or proteoglycans | Hyaluronic acid disaccharide or polymers<br>Chondroitin-sulfate disaccharide or polymers<br>Heparin-sulfate disaccharide or polymers<br>N-Acetyl-glucosamine, N-acetyl-galactosamine |

The metabolic derivative may be obtained in an accessible biological sample. The metabolic derivative is acquired in quantities that are sufficient for performing isotopic measurements, MIDA, and calculations of the proportions of isotopically labeled:unlabeled species.

Proteins and their Metabolic Derivatives

The biological molecules may be proteins. Examples of proteins are listed in Table 1, including collagen, myosin, and amyloid precursor protein.

One or more metabolic derivatives may be produced during biosynthesis or breakdown of the proteins. The metabolic derivatives of proteins may be amino acids and peptides. The metabolic derivatives may also be portions of the amino acids and peptides.

Preferably, the proteins are inaccessible biological molecules in inaccessible biological samples. Acquiring inaccessible proteins requires invasive procedures involving substantial risk and discomfort. The rate of biosynthesis or breakdown of the collagens is preferably measured by measuring metabolic derivatives of proteins in accessible biological samples.

The metabolic derivatives of preferably are preferably in an accessible biological sample. The metabolic derivatives of proteins preferably derive primarily, and optionally uniquely, from the specific types of collagen. Thus, protein metabolic derivatives or catabolic products preferably identify or characterize types of collagens, and their tissue source. Only small quantities, and not the total quantity, of collagen metabolic derivatives or catabolic products need to be acquired. Further, the metabolic derivatives or catabolic products of collagen cannot be directly re-incorporated into collagens or other biological molecules.

Metabolic derivatives may include one or more post-translational modifications. In one embodiment, the metabolic derivative may include, but is not limited to, a phosphorylated, methylated, hydroxylated, glycosylated, N-acetyl-glucosaminated, prenylated, palmitoylated, gamma-carboxylated, acetylated, sulfated, or other post-translationally modified amino acid or peptide wherein the peptide's composition or the amino acid's structure uniquely identifies the biological protein from which it is derived. Examples of this type of metabolic derivative (and the proteins from which they were derived) include 3-methyl-histidine (muscle mysin), hydroxyproline, hydroxylysine, glucosylgalactosylhydroxylysine, galactosylhydroxylysine (collagen) and gamma-carboxyglutamate (collagen).

Collagen

The biological molecule may be collagen and the metabolic derivative is an identifier of collagen. Biosynthesis and breakdown of collagen has been implicated in osteoporosis, fibrogenic disorders (e.g. hepatic cirrhosis, congestive heart failure, fibrotic lung disease, and photo-aging) rheumatoid arthritis, diabetes mellitus, and several kinds of cancers and disorders relating to unregulated cell growth.

Collagen is a triple stranded helical protein having 3 separate polypeptides, called tropocollagen. Collagen synthesized first as three separate strands of procollagen.

Procollagen forms a triple helix. The N-terminal and C-terminal peptides of procollagen are cleaved to produce tropocollagen. Collagen may be cross-linked.

Collagens are inaccessible biological molecules in inaccessible biological samples. Acquiring collagen samples directly from bone, for example, is an invasive procedure requiring substantial risk and discomfort. The rate of biosynthesis or breakdown of the collagens is preferably measured by measuring metabolic derivatives of collagens in accessible biological samples.

The metabolic derivatives of collagens are preferably in an accessible biological sample. The metabolic derivatives of collagen preferably derive primarily, and optionally uniquely, from the specific types of collagen. For example, N- and C-terminal collagen telopeptides, N- and C-terminal collagen propeptides, and post-translational modifications of collagens derive primarily from specific collagen types. Thus, the collagen metabolic derivatives or catabolic products preferably identify or characterize types of collagens, and their tissue source. Only small quantities, and not the total quantity, of collagen metabolic derivatives or catabolic products need to be acquired. Further, the metabolic derivatives or catabolic products of collagen cannot be directly re-incorporated into collagens or other biological molecules.

Collagens are Classified into Several Different Types.

Type I collagen is one of the most abundant protein species in the human body, accounting for at least 70% of total collagens. Most of this is present in bones, where about 90% of the organic matrix consists of type I collagen. The remainder is found in soft connective tissues all over the body, including hepatic tissue, cardiac tissue, lung tissue, and skin. The type I collagen molecule is a long, rigid rod—a shape necessary for its function as part of the collagen fiber in tissue. Two of the three constituent chains of the normal type I collagen molecule are identical $\alpha 1(I)$ chains, while the third is a different but homologous $\alpha 2(I)$ chain. These chains are all intertwined into a triple helix. The original gene products, the pro-$\alpha 1(I)$ and pro-$\alpha 2(I)$ of type I procollagen, are about 50% longer than the corresponding final products, $\alpha$ chains. The two additional, bulky domains at both ends of the molecule are usually called the amino-terminal and the carboxy-terminal propeptide of type I procollagen. These parts are removed en bloc from the procollagen by two specific endoproteinases, the N- and C-proteinases, once the molecule has reached the extracellular space.

Type II collagen is the major fibrous collagen of cartilage, representing 80-90% of the collagen in this tissue. Type II collagen is produced by chondrocytes, and its fibers make up 40-50% of cartilage dry weight. It is closely linked with type XI collagen, with which it has striking sequence homology. The globular domains of type XI and the increased glycosylation of type II collagen compared with the types I and III may have a role in the determination of the fibril diameter. The major function of type II collagen is to provide the tensile strength and toughness of cartilage.

The main cells synthesizing type I collagen in soft tissues are fibroblasts, which also always produce significant amounts of type III collagen. Type III collagen is the second most abundant collagen type in the human body. Its thin fibrils constitute the principal collagen in blood vessels and, together with type I collagen, in newly formed soft connective tissue. Its relative concentration is particularly large in young, metabolically active connective tissue, e.g. the granulation tissue of a healing wound. During wound healing its proportion decreases, probably due to the half-life, which is shorter for type III collagen than for type I collagen. The type III collagen molecule is a homotrimer of three identical a (III) chains. Its fibres are generally thinner than those containing mainly type I collagen and these fibers are covered by type III pN-collagen with retained aminoterminal propeptide. Such molecules are believed to prevent further lateral growth of the fiber.

Type IV collagen is a network forming collagen. Type IV collagens assemble into a feltlike sheet or meshwork that constitutes a major part of mature basal laminae.

Representative metabolic derivatives of collagen are listed in Table 1. The metabolic derivative may be an N- or C-terminal telopeptide or an N- or C-terminal propeptide, including but not limited to N-terminal telopeptide α1(I) (SEQ ID NO:1), N-terminal telopeptide α2(I) (SEQ ID NO:2), N-terminal telopeptide α2(I) (SEQ ID NO:3), N-terminal telopeptide α1(II) (SEQ ID NO:4), N-terminal telopeptide α1(III) (SEQ ID NO:5), C-terminal telopeptide α1(I) (SEQ ID NO:6), C-terminal telopeptide α2(I) (SEQ ID NO:7), C-terminal telopeptide α1(II) (SEQ ID NO:8), C-terminal telopeptide α1(II) (SEQ ID NO:9), C-terminal telopeptide α1(II) (SEQ ID NO:10), C-terminal telopeptide α1(III) (SEQ ID NO:11), cross-linked carboxy-terminal peptide of type I collagen (ICTP), PINP(α1) (SEQ ID NO:12), PICP(α1) (SEQ ID NO:13), PINP(α2) (SEQ ID NO:14), PICP(α2) (SEQ ID NO:15), PIINP(α1) (SEQ ID NO:16), PIICP(α1) (SEQ ID NO: 17), PIIINP(α1) (SEQ ID NO: 18), PIIICP(α1) (SEQ ID NO: 19), PIVNP(α1) (SEQ ID NO:20), PIVNP(α2) (SEQ ID NO:21), PIVNP(α2) (SEQ ID NO:22), PIVNP(α3) (SEQ ID NO:23), PIVNP(α4) (SEQ ID NO:24), PIVNP(α5) (SEQ ID NO:25), and PIVNP(α6) (SEQ ID NO:26). Each peptide identifies a specific type of collagen.

The collagen metabolic derivative is specific to the source of collagen. Table 1 shows specific collagen products associated with each tissue. The metabolic derivative also may be a post-translational modification or crosslink of collagen. Post-translational modifications of collagen include pyridinoline, hydroxy-pyridinoline, 4-hydroxyproline, 3-hydroxyproline, hydroxylysine, glucosylgalactosyl-hydroxylysine, and galactosylhydroxylysine. Each of these metabolic derivatives is an identifier of collagen.

One skilled in the art will recognize that other known metabolic derivatives of collagen may be detected by the methods described herein.

Myosin

The biological molecule may also be myosin from muscle tissue. Muscle is a muscle protein that drives muscle contraction by binding actin and hydrolyzing ATP. Myosin biosynthesis and breakdown may be determined by identifying myosin breakdown products.

Myosin is an inaccessible biological molecule found in inaccessible biological samples. Acquiring myosin samples directly in muscle tissue biopsies, for example, is an invasive procedure requiring substantial risk and discomfort. The rate of biosynthesis or breakdown of myosin is preferably determined by measuring metabolic derivatives of myosin in accessible biological samples.

The metabolic derivatives of myosin are preferably in an accessible biological sample. The metabolic derivatives of myosin preferably derive primarily, and optionally uniquely, from the myosin. 3-methyl histidine, for example, derives primarily from myosin. Peptides released from myosin during proteolysis may escape into the circulation and identify myosin. Thus, the myosin metabolic derivatives or catabolic products preferably identify or characterize myosin. Only small quantities, and not the total quantity, of myosin metabolic derivatives or catabolic products need to be acquired. Optionally, the metabolic derivatives or catabolic products of myosin cannot be directly re-incorporated into myosin or other biological molecules.

Table 1 lists examples of metabolic derivatives specific to myosin.

One skilled in the art will recognize that other known metabolic derivatives of myosin may be detected by the methods described herein.

Amyloid Precursor Protein

The biological molecule may be Amyloid Precursor Protein (APP). The identification of amyloid-rich plaques has long been a diagnostic tool for pathologists investigating Alzheimer's disease. The plaques are formed through the accumulation and aggregation of beta-amyloid peptides derived from the APP, and are characteristically found in the brain parenchyma and around blood vessels.

APP is an inaccessible biological molecule found in inaccessible biological samples. Acquiring APP samples directly from brain, for example, is an invasive procedure requiring substantial risk or resulting in serious injury or death. The rate of biosynthesis or breakdown of APP is preferably determined by measuring metabolic derivatives of APP in accessible biological samples.

The metabolic derivatives of APP are preferably in an accessible biological sample. The metabolic derivatives of APP preferably derive primarily, and optionally uniquely, from the APP. Beta amyloid precursor peptides, for example, derive specifically from APP. Thus, the APP metabolic derivatives or catabolic products preferably identify or characterize APP. Only small quantities, and not the total quantity, of APP metabolic derivatives or catabolic products need to be acquired. Further, the metabolic derivatives or catabolic products of APP cannot be directly re-incorporated into APP or other biological molecules.

The metabolic derivative may be an APP specific metabolic derivative. The metabolic derivative may be amyloid beta (1-40) (SEQ ID NO:27), amyloid beta (1-42) (SEQ ID NO:28), or APP C peptide. One of skill in the art will recognize that the metabolic derivatives may be components of amyloid beta (1-40) (SEQ ID NO:27), amyloid beta (1-42) (SEQ ID NO:28), or other APP specific metabolic derivatives.

One skilled in the art will recognize that other known metabolic derivatives of APP may be detected by the methods described herein.

Myelin Basic Protein

The biological molecule may be myelin basic protein (MBP). Loss of MBP, or demyelination, is associated with multiple sclerosis, a neurodegenerative disease. Increase in MBP-like material in urine is associated with demyelination.

MBP is an inaccessible biological molecule found in inaccessible biological samples. Acquiring MBP samples directly from brain, for example, is an invasive procedure carrying a risk of serious injury or death. Preferably, the rate of biosynthesis or breakdown of MBP determined by measuring metabolic derivatives of MBP in accessible biological samples.

The metabolic derivatives of MBP are preferably in an accessible biological sample. The metabolic derivatives of MBP preferably derive primarily, and optionally uniquely, from the MBP. MBP-like material, for example, derives primarily from MBP. Thus, the MBP metabolic derivatives or catabolic products identify or characterize MBP. Only small quantities, and not the total quantity, of MBP metabolic derivatives or catabolic products need to be acquired. Further, the metabolic derivatives or catabolic products of MBP cannot be directly re-incorporated into MBP or other biological molecules.

The metabolic derivative may be specific to MBP. In one embodiment, the catalytic product is MBP-like material. In a further embodiment, the MBP-like material is in urine.

One skilled in the art will recognize that other known metabolic derivatives of MBP may be detected by the methods described herein.

Polynucleotides and their Metabolic Derivatives

The biological molecule may also be polynucleotide. The polynucleotide may be DNA or RNA.

DNA biosynthesis and breakdown are associated with cell proliferation and death, respectively. Cancer and other disorders relating to cell proliferation may be monitored determining the rate of biosynthesis and breakdown of polynucleotides.

Preferably, polynucleotides are inaccessible biological molecules in inaccessible biological samples. The rate of biosynthesis or breakdown of the polynucleotides is preferably measured by measuring metabolic derivatives of polynucleotides in accessible biological samples.

The metabolic derivatives of polynucleotides are preferably in an accessible biological sample. The metabolic derivatives of polynucleotides preferably derive primarily, and optionally uniquely, from polynucleotides. The metabolic derivatives or catabolic products preferably identify or characterize polynucleotides, and optionally their tissue source. Only small quantities, and not the total quantity, of metabolic derivatives or catabolic products need to be acquired. Further, the metabolic derivatives or catabolic products cannot be directly re-incorporated into polynucleotides or other biological molecules.

Table 1 lists examples of metabolic derivatives from polynucleotides.

The metabolic derivative may be a DNA- or RNA-specific metabolic derivative such as deoxyribose, ribose, or a specific sequence of polynucleotides. The metabolic derivative may be produced by post-replication modification of bases in DNA. In another embodiment, the metabolic derivative is a methylated or oxidatively modified base. In another embodiment, the metabolic derivative may be a methyl-cytosine, 8-oxo-guanosine, deoxyribose, and ribose.

One skilled in the art will recognize that other known metabolic derivatives of polynucleotides may be detected by the methods described herein.

Lipids and their Metabolic Derivatives

The biological molecule also may be a lipid. Lipids are components of membranes, including membranes in brain, pancreas and other tissues. Lipids include, but are not limited to, acyl-glycerides, phospholipids, cholesterol and its derivatives, ceramides, sphingosines, and glycolipids.

Frequently, lipids are an inaccessible biological molecules found in inaccessible biological samples. Acquiring lipid samples directly from brain, for example, is an invasive procedure requiring substantial risk and discomfort. The rate of biosynthesis or breakdown of lipids is preferably measured by measuring metabolic derivatives of lipids in accessible biological samples.

The metabolic derivatives of lipids are preferably in an accessible biological sample. 22-(R)-hydroxycholesterol, 24-(S)-hydroxycholesterol, or 24,25-(S)-epoxycholesterol, galactocerebroside, galactose from galactocerebroside, sphingomyelin, and sphingosines for example, specifically identify their lipids of origin. The metabolic derivatives of lipids preferably derive primarily, and optionally uniquely, from the lipids. Thus, the lipid metabolic derivatives or catabolic products preferably identify or characterize lipids. Only small quantities, and not the total quantity, of lipid metabolic derivatives or catabolic products need to be acquired. Further, the metabolic derivatives or catabolic products of lipids preferably cannot be directly re-incorporated into lipids or other biological molecules.

Glycosaminoglycans, Proteoglycans, and their Metabolic Derivatives

Glycosaminoglycans and proteoglycans are a complex class of biomolecules that play important roles in the extracellular space (e.g. cartilage, ground substance, and synovial joint fluid).

Preferably, the glycosaminoglycans and proteoglycans are inaccessible biological molecules in inaccessible biological samples. The rate of biosynthesis or breakdown of the polynucleotides is preferably measured by measuring metabolic derivatives of glycosaminoglycans and proteoglycans in accessible biological samples.

The metabolic derivatives of glycosaminoglycans and proteoglycans are preferably in an accessible biological sample. The metabolic derivatives of glycosaminoglycans and proteoglycans preferably derive primarily, and optionally uniquely, from glycosaminoglycans or proteoglycans. The metabolic derivatives or catabolic products preferably identify or characterize glycosaminoglycans and proteoglycans, and optionally their tissue source. Only small quantities, and not the total quantity, of metabolic derivatives or catabolic products need to be acquired. Further, the metabolic derivatives or catabolic products cannot be directly re-incorporated into glycosaminoglycans, proteoglycans or other biological molecules.

The metabolic derivative may include one or more of the following: hyaluronic acid disaccharide or polymers thereof, N-acetyl glucosamine, N-acetyl-galactosamine, chondroitin-sulfate disaccharide or polymers thereof, heparin sulfate disaccharide or polymers thereof, and keratin sulfate disaccharide or polymers thereof.

The metabolic derivatives of lipids are preferably in an accessible biological sample. Hyaluronic acid disaccharide or polymers thereof, N-acetyl glucosamine, N-acetyl-galactosamine, chondroitin-sulfate disaccharide or polymers thereof, and Heparin sulfate disaccharide or polymers thereof, for example, specifically identify their origin. The metabolic derivatives or catabolic products preferably identify or characterize specific glycosaminoglycans or proteoglycans.

(ii) Obtaining One or More Biological Samples from Said Individual

Biological samples are obtained from the individual. Specific methods of obtaining biological samples are well known in the art. Preferably, the biological sample is an accessible biological sample.

Biosynthesis or breakdown of the biological molecule may occur at a different tissue or fluid from the obtained one or more biological samples.

One or more metabolic derivatives may be obtained, and optionally partially purified or isolated, from the biological sample using standard biochemical methods known in the art.

The frequency of biological sampling can vary depending on different factors. Such factors include, but are not limited to, the nature of the metabolic derivatives, ease and safety of sampling, biological rate constants and turnover kinetics of the metabolic derivative or the biological molecule from which it was derived, and the half-life of a drug used in a treatment if monitoring responses to treatment.

The one or more metabolic derivatives may also be purified partially purified, or optionally, isolated, by conventional purification methods including high pressure liquid chromatography (HPLC), fast performance liquid chromatography (FPLC), chemical extraction, thin layer chromatography, gas chromatography, gel electrophoresis, and/or other separation methods known to those skilled in the art.

In another embodiment, the one or more metabolic derivatives may be hydrolyzed or otherwise degraded to form smaller molecules. Hydrolysis methods include any method known in the art, including, but not limited to, chemical hydrolysis (such as acid hydrolysis) and biochemical hydrolysis (such as peptidase or nuclease degradation). Hydrolysis or degradation may be conducted either before or after purification and/or isolation of the metabolic derivative. The metabolic derivatives also may be partially purified, or optionally, isolated, by conventional purification methods including high performance liquid chromatography (HPLC), fast performance liquid chromatography (FPLC), gas chromatography, gel electrophoresis, and/or any other methods of separating chemical and/or biochemical compounds known to those skilled in the art.

iii) Detecting the Incorporation of Said Label in Said One or More Metabolic Derivatives Isotopic enrichment in metabolic derivatives can be determined by various methods such as mass spectrometry, including but not limited to gas chromatography-mass spectrometry (GC-MS), isotope-ratio mass spectrometry, GC-isotope ratio-combustion-MS, GC-isotope ratio-pyrolysis-MS, liquid chromatography-MS, electrospray ionization-MS, matrix assisted laser desorption-time of flight-MS, Fourier-transform-ion-cyclotron-resonance-MS, cycloidal-MS, nuclear magnetic resonance (NMR), or liquid scintillation counting.

Incorporation of labeled isotopes into biological molecules may be measured directly. Alternatively, incorporation of labeled isotopes may be determined by measuring the incorporation of labeled isotopes into one or metabolic derivatives, or hydrolysis or degradation products of metabolic derivatives. The hydrolysis products may optionally be measured following either partial purification or isolation by any known separation method, as described previously.

a. Mass Spectrometry

Mass spectrometers convert components of a sample into rapidly moving gaseous ions and separate them on the basis of their mass-to-charge ratios. The distributions of isotopes or isotopologues of ions, or ion fragments, may thus be used to measure the isotopic enrichment in one or more metabolic derivatives.

Generally, mass spectrometers include an ionization means and a mass analyzer. A number of different types of mass analyzers are known in the art. These include, but are not limited to, magnetic sector analyzers, electrostatic analyzers, quadrapoles, ion traps, time of flight mass analyzers, and fourier transform analyzers. In addition, two or more mass analyzers may be coupled (MS/MS) first to separate precursor ions, then to separate and measure gas phase fragment ions.

Mass spectrometers may also include a number of different ionization methods. These include, but are not limited to, gas phase ionization sources such as electron impact, chemical ionization, and field ionization, as well as desorption sources, such as field desorption, fast atom bombardment, matrix assisted laser desorption/ionization, and surface enhanced laser desorption/ionization.

In addition, mass spectrometers may be coupled to separation means such as gas chromatography (GC) and high performance liquid chromatography (HPLC). In gas-chromatography mass-spectrometry (GC/MS), capillary columns from a gas chromatograph are coupled directly to the mass spectrometer, optionally using a jet separator. In such an application, the gas chromatography (GC) column separates sample components from the sample gas mixture and the separated components are ionized and chemically analyzed in the mass spectrometer.

When GC/MS is used to measure mass isotopomer abundances of organic molecules, hydrogen-labeled isotope incorporation from labeled water is amplified 3 to 7-fold, depending on the number of hydrogen atoms incorporated into the organic molecule from labeled water.

In one embodiment, isotope enrichments of metabolic derivatives may be measured directly by mass spectrometry.

In another embodiment, the metabolic derivatives may be partially purified, or optionally isolated, prior to mass spectral analysis. Furthermore, hydrolysis or degradation products of metabolic derivatives may be purified.

In another embodiment, isotope enrichments of metabolic derivatives after hydrolysis of the metabolic derivative are measured by gas chromatography-mass spectrometry.

In each of the above embodiments the biosynthesis rate of the biological molecule can be calculated by application of the precursor-product relationship using either labeled precursor molecule enrichment values or asymptotic isotope enrichment in the relevant metabolic derivative of a fully turned over biological molecule to represent the true precursor pool enrichment. Alternatively, the biosynthesis or breakdown rate may be calculated using an exponential decay curve by application of exponential or other die-away kinetic models.

b. Liquid Scintillation

Radioactive isotopes may be observed using a liquid scintillation counter. Radioactive isotopes such as $^3H$ emit radiation that is detected by a liquid scintillation detector. The detector converts the radiation into an electrical signal, which is amplified. Accordingly, the number of radioactive isotopes in a metabolic derivative may be measured.

In one embodiment, the radioisotope-enrichment value in a biological sample may be measured directly by liquid scintillation. In a further embodiment, the radio-isotope is $^3H$.

In another embodiment, the metabolic derivative or components thereof may be partially purified, or optionally isolated, and subsequently measured by liquid scintillation counting.

In each of the above embodiments the biosynthesis rate of the biological molecule can be calculated by application of the precursor-product relationship using either labeled precursor molecule enrichment values or asymptotic isotope enrichment in the relevant metabolic derivative of a fully turned over biological molecule to represent the true precursor pool enrichment. Alternatively, the breakdown rate may be calculated using an exponential or other die-away model decay curve.

(iv) Determining the Rate of Biosynthesis or Breakdown

Biosynthetic and breakdown rates may be calculated by combinatorial analysis, by hand or via an algorithm. Variations of Mass Isotopomer Distribution Analysis (MIDA) combinatorial algorithm are discussed in a number of different sources known to one skilled in the art. Specifically, the MIDA calculation methods are the subject of U.S. Pat. No. 5,338,686, incorporated herein by reference. The method is further discussed by Hellerstein and Neese (1999), as well as Chinkes, et al. (1996), and Kelleher and Masterson (1992), all of which are hereby incorporated by reference in their entirety. For example, Hellerstein and Neese teach that mass isotopomer distribution analysis (MIDA) is a technique based on combinatorial probabilities and the labeling patterns in intact polymers that can be said to provide a fundamental "equation for biosynthesis." The first rule of MIDA is that there must be combinations possible in the molecule analyzed. Polymers studied must be analyzed intact, or with at least two subunits present, because the distribution of isotopomeric species carries the essential information. The second rule of MIDA is that subpopulations of molecules must be distinguishable and quantifiable. The variations within a population of assembled polymers carry the information crucial for MIDA. The notion that there is a homogenous precursor pool and a uniform product pool is replaced by the notion of subpopulations of precursors (some A, some B) and subpopulations of products (of characteristic isotopomeric composition in quantifiable proportions). Any analytic modality must therefore be capable of discriminating among different polymeric subpopulations (species) present within the population. The third rule of MIDA is that dilution of the monomeric (precursor) and polymeric (product) pools affects abundance distributions differently. Both sources of dilution can alter the relative proportion of polymeric species containing no labeled subunits vs. labeled subunits, but only dilution in the precursor pool can alter the internal quantitative relationships among labeled species. It is this differential effect on "amount" (proportion of the polymer population containing any labeled subunits) vs. "pattern" (relationships within the population of labeled polymers) that allows independent calculation of p and f, respectively.

In addition to the above-cited references, calculation software implementing the method is publicly available from Professor Marc Hellerstein, University of California, Berkeley.

The biosynthesis rate (k) of biological molecule may be calculated, using the standard isotope dilution equation, for example $$A_t = A_0 \cdot e^{-kt},$$

where $A_t$=the proportion of labeled metabolic derivative in a sample at time t
$A_0$=the proportion of labeled metabolic derivative in sample at time zero
t=time
k=biosynthesis rate constant $$k = \frac{-\ln\left(\frac{A_t}{A_0}\right)}{t}.$$

Similarly, breakdown rate constants may be calculated based on an exponential or other kinetic decay curve, known to those skilled in the art.

IV. Methods of Use

The method disclosed herein has many biological and medical applications. The measurements described herein are applicable for numerous medical utilities such as monitoring pre-existing physiological conditions, diagnosis of disease states, and assessing risk of development of disease states or physiological conditions, in addition to pharmaceutical research utilities, such as screening of candidate gene or protein targets, phenotypic validation of candidate drug agents, FDA phase I and II human validation studies of candidate drug agents, FDA phase III approval of candidate drug agents, and FDA phase IV approval studies, or other post approval market positioning or mechanism of drug action studies. Table 2 shows a number of diseases and disorders that correlate to different inaccessible biological molecules.

In one aspect, the invention provides the determination of tissue synthesis or breakdown rates of the molecule of interest. Such molecules of interest can be indicative of a particular disease state or indicative of an inclination to develop a particular disease state. In another aspect, the invention provides the ability for diagnosis and medical management of a number of disease states or physiological states or conditions characterized by alterations in biological molecular synthesis and/or turnover rates, including, but not limited to, osteoporosis (e.g., bone collagen synthesis and turnover rates); liver, cardiac, lung, and skin collagen synthesis rates in fibrogenic disorders (e.g., hepatic cirrhosis, congestive heart failure, fibrotic lung disease, scleroderma and photo-aging); central nervous system amyloid precursor protein and amyloid fibril synthesis rate, proteolytic pathways, life-span and residence time in Alzheimer's disease; muscle myosin synthesis and turnover rates in wasting disorders, athletic training, and anabolic therapies; multiple sclerosis (brain myelination, demyelination and remyelination rates); rheumatoid arthritis and osteoarthritis (synovial fluid and articular cartilage synthesis and breakdown rates of joint protective glycosaminoglycans, and proteoglycans).

Other physiological states that can be diagnosed by the methods of the invention include, but are not limited to, osteoporosis, left-ventricular hypertrophy, liver cirrhosis, liver fibrosis, congestive heart failure, scleroderma, black-lung (coal-miner's pneumoconiosis), cardiac fibrosis, lung fibrosis, Alzheimer's disease, multiple sclerosis, rheumatoid arthritis, diabetes mellitus, muscle wasting syndromes, muscular dystrophies, athletic training, and cancer.

In another aspect, the invention is a method for monitoring a response of a disease or a condition in an individual to a therapeutic or disease-preventative intervention by assessing the rate of synthesis or breakdown of an biological molecule before the initiation of such intervention and then assessing the rate of synthesis or breakdown of the same biological molecule after the initiation of such therapeutic or disease-preventative intervention; and comparing both rates of synthesis or breakdown to monitor the response of a disease or a condition to the therapeutic intervention. In one embodiment, the therapeutic intervention is an anabolic therapy. The rate of synthesis and breakdown of myosin in muscle is measured by the incorporation of a labeled precursor (e.g., $^2H_3$-leucine, $^2H_5$-histidine, $^{13}C$-serine, $^2H_2O$) into urinary 3-methlhistidine, both before anabolic therapy (e.g., recombinant growth hormone, androgens, etc.) and after anabolic therapy. The rates after therapy are compared to the rates before therapy, to establish the effects of therapy.

In another aspect, the invention is a method for determining a risk for developing a disease state in an individual by determining the rate of synthesis or breakdown of an biological molecule indicative of the disease state and comparing the rate of synthesis or breakdown to a reference rate of synthesis or breakdown of the biological molecule wherein the reference rate reveals risk for the disease state. In one embodiment, the disease state is osteoporosis and the rate of synthesis and/or breakdown of bone collagen is the risk factor for developing this disease. The rate of synthesis and/or breakdown of bone collagen is measured based on the incorporation of a labeled precursor (e.g., $^{13}C_1$-lysine, $^2H_2O$) into a secreted metabolic derivative of bone collagen (e.g., N-terminal telopeptides, deoxypyridinoline) in a subject and compared to reference values, to assess risk for the subsequent development of osteoporosis.

In another aspect, the invention is a method for determining a whole-body pool size of an biological molecule in an individual by: (1) measuring a daily fractional synthesis rate by the method using the method described above; (2) collecting the total excretion of an indicative metabolic derivative; (3) measuring the complete daily excretion rate (ER); and (4) dividing the daily ER by the daily fractional replacement rate of the metabolic derivative to calculate whole-body pool size of the biological molecule in the individual by use of the following equation:

$$\text{pool-size}(g) = \frac{E.R.(g/d)}{k(d^{-1})}$$

where k=fractional replacement rate constant. This can be used for assessing for the presence of cancer as exemplified in Example 5.

V. Advantages Provided by Current Invention

The invention has numerous advantages over previous techniques for measuring rates of biosynthesis and breakdown of biological polymers that require direct sampling of tissues by physical means. Most importantly, there is no requirement for direct tissue sampling, which in many circumstances is impractical, inconvenient, potentially risky, anxiety-provoking, or impossible in practice (e.g., such as brain tissue sampling).

When comparing this invention to previous methods that measure the concentration or amount of a catabolic product released into the blood or urine, the present invention has a number of advantages. First, there is no requirement for quantitative recovery of metabolic derivatives. Previous techniques required complete or near-complete quantitative recovery of the metabolic derivatives from a biological sample in order to estimate the rate of production of the metabolic derivative (and from this, the rate of biosynthesis or breakdown of the molecule from which the metabolic derivative was derived). Factors that affect these techniques include in vivo clearance, storage or further metabolic transformations of the metabolic derivative. In contrast, the current invention requires only isolation of a quantity of the metabolic derivative that is sufficient for measurement of its isotopic labeling fraction, because the ratio of labeled to unlabeled metabolic derivatives or catabolic products is independent of the yield of metabolic derivatives or catabolic products attained. Accordingly, yield or recovery of the metabolic derivative is not a limiting factor or assumption of this invention and the method taught in the present invention can be performed rigorously regardless or variables such as in vivo clearance efficiency, metabolic transformation rate, storage, etc. of the metabolic derivative.

Second, in techniques in the prior art that involve measuring the concentration or amount of a metabolic derivative released into the bloodstream or urine, direct estimation of only the breakdown rate of the biological molecule of interest was allowed (6), based on the rate of release of a metabolic derivative. In contrast, the present invention teaches a method for measuring aspects of biosynthesis (e.g., synthesis rate, transit time, tissue residence time, etc.) in addition to breakdown rates of the molecule of interest.

TABLE 2

Disease and Disorder, Tissues and Organs, and Associated Inaccessible Biological Molecule

| Disease/Disorder | Tissue/Organ | "Inaccessible" Molecule |
| --- | --- | --- |
| Osteoporosis | Bone | Collagen |
| Photoaging (wrinkles) | Skin | Collagen |
| Liver fibrogenesis | Liver | Collagen |
| Cardiac fibrogenesis | Heart | Collagen |
| Pulmonary Fibrogenesis | Lung | Collagen |
| Scleroderma | Skin | Collagen |
| Arthritis (rheumatoid, osteo) | Joint | Glycosaminoglycans and proteoglycans |
| Alzheimer's Disease | Brain | Amyloid fibrils |
| DNA damage/mutation | Any tissue | Oxidized polynucleotides |
| Cell Proliferation Disorders, Cancer | Any tissue | Polynucleotides |
| Multiple Sclerosis | Brain | Myelin Basic Protein, Myelin membrane lipids (galactosyl-cerebrosides) |

TABLE 2-continued

Disease and Disorder, Tissues and Organs, and Associated Inaccessible Biological Molecule

| Disease/Disorder | Tissue/Organ | "Inaccessible" Molecule |
| --- | --- | --- |
| Frailty, wasting | Skeletal Muscle | Myosin |
| Brain development | Brain | Membrane lipids |

LITERATURE CITED AND INCORPORATED BY REFERENCE IN ITS ENTIRETY

1. Wolfe, R. R. 1984. Tracers in Metabolic Research. Radio-Isotope and Stable Isotope/Mass Spectrometric Methods. Alan R. Liss, Inc., NY.
2. Hellerstein M K, Neese R. Mass isotopomer distribution analysis: a technique for measuring biosynthesis and turnover of polymers. Am J Physiol 263:E988-E1001, 1992.
3. Hellerstein M K, Neese R A. Mass isotopomer distribution analysis at eight years: theoretical, analytic and experimental considerations. Am J Physiol 276 (Endocrinol Metab 39): E1146-E1162, 1999.
4. Zilversmit, D. B., C. Entenman, and M. Fishler. 1943. The calculation of turnover rate and turnover time from experiments involving the use of labeling agents. J. Gen. Physiol. 26:325-331.
5. Hellerstein M. Methods for measuring polymerisation biosynthesis: three general solutions to the problem of the "true precursor." Diabetes Nutr Metab 13(1):46-60, 2000.
6. Waterlow, J. C., P. J. Garlick, and D. J. Millward, eds. 1978. Protein Turnover in Mammalian Tissues and in the Whole Body. North Holland, Amsterdam.
7. Ho D D, Neumann A U, Perelson A S, Chen W, Leonard J M, Markowitz M. Rapid turnover of plasma virions and $CD_4$ lymphocytes in HIV-1 infection. Nature 373:123-6, 1995.
8. Wei X, Ghosh S K, Taylor M E, Johnson V A, Emin E T, Deutsch P, Lifson J D, Bonhoeffer S, Nowak M A, Hahn B H et al. Viral dynamics in human immunodeficiency virus type 1 infection. Nature 373 117-120, 1995
9. Schimke R T, Doyle D. Control of enzyme levels in animal tissues. Annu Rev Biochem 39: 929-76, 1970.
10. Eyre D R. Bone biomarkers as tools in osteoporosis management. Spine 22(24 Suppl): 17S-24S, 1997.
11. Young V R, Munro H N. Ntau-methylhistidine (3-methylhistidine) and muscle protein turnover: an overview. Fed Proc 37(9): 2291-300, 1978.

Example 1

Bone Collagen Biosynthesis Using Urinary Pyridinoline/Deoxypyridinoline (Free or Bone-Collagen N-Terminal Peptide-Derived) as the Metabolic Derivative An individual with suspected or diagnosed osteoporosis or other disorder of bone collagen biosynthesis or breakdown is given a labeled precursor molecule that is incorporated into newly synthesized collagen in the body. In one such embodiment, this is $^{13}C_1$-lysine (at a dose of 20 mg/ml, in water, for example) given orally to drink (25 ml) with morning and evening meals for 7 days (total of 14 doses). A urine aliquot (10 ml) is collected from the individual at a defined time point or points (e.g., on the final day of the $^{13}C_1$-lysine protocol (day 7) and 7 days after completing the $^{13}C_1$-lysine intake protocol (day 14)).

In another embodiment, the individual is given labeled water in similar way to the $^{13}C_1$-lysine (for example, 50 ml of 70% $^2H_2O$ twice a day for 7 days).

Urinary free or peptide-bound pyridinoline/deoxypyridinoline (HP/DP) are isolated (e.g., size exclusion chromatography or filtration to separate free from peptide-bound HP/DP; MW 1,000 cut-off; immunoprecipitation or immunoaffinity chromatography). Alternatively or in addition, to isolate specific N-terminal collagen peptides derived from bone, liver and heart are isolated (using antibodies available commercially), acid hydrolysis (6N HCl/110° C. in sealed tube for 24 hr.); clean up of HP/DP by push-through SPE reversed-phase column; collection of HP/DP off reversed-phase C-18 HPLC column).

The HP/DP from a fraction of interest (e.g., total free or from a bone-collagen derived N-terminal peptide) that derives from bone collagen is injected into an LC/MS (e.g., BioQ electrospray/MS). Mass isotopomer peaks of HP (m/z 429.2, 430.2, and 431.2) and DP (413.2, 414.2, 415.2) are monitored. Relative abundances of above mass isotopomers are quantified in the sample analyzed and in unlabeled standards (e.g., m/z 430.2/(429.2+430.2+431.2)=0.1650 in the day 14 sample and 0.1500 in the unlabeled standard). The proportion of labeled:unlabeled HP or DP molecules present is then calculated by MIDA methods.

By one such method, the proportion of excess labeled HP/DP molecules is calculated by subtraction of unlabeled standards from labeled samples (e.g., 0.0150, or 1.5%). Free lysine is isolated from the urine sample taken on the final day of $^{13}C_1$-lysine intake protocol (day 7) using an SPE column; then derivatized to butyl-ester acetamide-lysine, using butanolic HCl followed by acetic anhydride. The derivatized lysine is injected into a gas chromatograph/mass spectrometer (e.g., HP model 5973 instrument) using a DB-225 column. The mass spectrum of the lysine peak is collected, monitoring masses at m/z 287 and 288 and quantifying their relative abundances compared to unlabeled standards (e.g., m/z 288/(287+288)=0.3752 in day 7 sample and 0.1433 in unlabeled standard).

The proportion of labeled:unlabeled free lysine molecules is calculated using mass isotopomer calculations, to establish the maximum proportion of label that could have been incorporated into tissue collagen during the $^{13}C_1$-lysine intake period (e.g., 30%). The ratio of the labeled proportion of HP or DP molecules derived predominantly from bone (total free HP/DP) or exclusively from bone (bone collagen N-terminal peptide), corrected for the 3 lysine labeling positions present, is compared to the labeled proportion of free lysine molecules and the ratio is calculated (e.g., 0.0050/0.3000, or 1.67%), based on the precursor-product equation; this ratio represents the fraction of bone collagen that was newly synthesized during the 7-day period of $^{13}C_1$-lysine intake.

The biosynthesis rate of bone collagen in the individual, during the period of $^{13}C_1$-lysine intake, is calculated (e.g., 0.24% per day, reflecting a doubling-time or replacement half-life of 289 days).

The above procedure and calculations are repeated in the same individual after a therapeutic intervention (e.g., treatment with conjugated estrogens, parathyroid hormone, calcium, bisphosphates, etc.), to determine the effects of the treatment on tissue collagen biosynthesis in the individual, or after a potential change in disease activity (e.g., bed-rest) to determine progression of osteoporosis in the individual.

Example 2

Tissue Fibrogenesis Using Urinary Pyridinoline/Deoxypyridinoline Derived from Liver, Heart, Lung, or Skin Collagen N-Terminal Peptide as the Metabolic Derivative An individual with a suspected or diagnosed fibrogenic disorder (e.g., hepatic fibrosis and/or cirrhosis, pulmonary insterstitial fibrosis (PIF), or progressive cardiac failure) or with problematic skin photoaging (wrinkles) is given a labeled precursor that is incorporated into collagen during biosynthesis in the body. In one such embodiment, this is $^2H_2O$ (at a dose of 50 ml, for example) given orally to drink with morning and evening meals for 42 days (6 weeks). A urine aliquot (10 ml) is collected from the individual at a defined time point or points (e.g., on the final day of the $^2H_2O$ protocol (day 42).

Urinary N-terminal collagen-peptides specific for liver, heart, or skin are isolated by, e.g., filtration to separate free HP/DP from collagen-derived peptides; immunoprecipitation or immunoaffinity chromatography to isolate specific N-terminal collagen-peptides released from liver or heart using antibodies available commercially; acid hydrolysis (6N HCl/110° C. in sealed tube for 24 hr.); clean up of released HP/DP by push-through SPE reversed-phase column; collection of HP/DP off reversed-phase C-18 HPLC column. In one embodiment, the alanine and glycine released by hydrolysis from the peptide fraction of interest reflecting liver or heart collagen are derivatized (e.g. N-acetyl-butyl-ester of glycine or alanine, formed by reaction with butanolic HCl and acetic anhydride) is injected into a GC/MS according to conditions. Mass isotopomer peaks of glycine (m/z 174, 175, and 176, representing parent, $M_{+1}$ and $M_{+2}$ ions) and alanine (188, 189, and 190 representing parent, $M_{+1}$ and $M_{+2}$ ions) are monitored.

Relative abundances of the above mass isotopomers are quantified in both the sample(s) and the unlabeled standards [e.g., m/z 189/(188+189+190)=0.1050 in the day 14 sample and 0.0900 in the unlabeled standard of alanine; m/z 174/(174+175+176)=0.0935 for glycine in the day 14 sample and 0.0860 in the unlabeled standard]. The proportion of labeled:unlabeled alanine or glycine molecules present in the sample is then calculated.

By one such calculation method, the proportion of excess labeled:unlabeled alanine or glycine molecules present is calculated by subtraction of unlabeled standards from labeled samples (e.g., 0.0150, or 1.5% for alanine; 0.0075, or 0.75%, for glycine). The enrichment of body $^2H_2O$ is measured (e.g. conversion to acetylene by addition to calcium carbide, then derivatization to the tetrabromo-ethane for analysis by gas chromatography/mass spectrometry). The proportion of labeled alanine or glycine present in tissue protein biosynthetic pools is then calculated, based on body $^2H_2O$ enrichments, using precursor-product equations and MIDA (e.g. 0.1260 $M_{+1}$, or 3.1% excess $M_{+1}$ for alanine if $^2H_2O$=1.0%; 0.1020 $M_{+1}$ or 1.6% excess $M_{+1}$ for glycine, if $^2H_2O$=1.0%).

The labeled proportion of alanine or glycine molecules derived from liver or heart collagen is compared to the labeled proportion of alanine or glycine present in tissue protein biosynthetic pools and the ratio is calculated (e.g., 1.5%/3.1%=48% from alanine or 0.75%/1.6%=47% from glycine), based on the precursor-product equation. This ratio represents the fraction of liver, heart, lung, or skin collagen that was newly synthesized during the 7-day period of $^2H_2O$ intake. The biosynthesis rate of liver or heart collagen in the individual, during the period of $^2H_2O$ intake, is then calculated (e.g., 1.6% per day, or a doubling-time or replacement half-life of 45 days).

The above procedure and calculations, or other calculation methods appropriate for precursor-product mathematical relationships are repeated in the same individual after a therapeutic intervention (e.g., treatment with antifibrogenic agents) to determine the effects of the treatment on liver or cardiac fibrogenesis in the individual, or after a potential change in disease activity (e.g., cessation of alcohol intake in an individual with liver fibrosis, treatment of with antifibrigenic or anti-inflammatory agents in PIF, treatment of cardiac failure with angiotensin-converting enzyme inhibitors in an individual with cardiac fibrosis) to determine the progression of underlying fibrogenesis in the individual.

Example 3

Brain Amyloid Precursor Protein (APP) Biosynthesis Using Amyloid (A)-Beta 1-40 and 1-42 Peptides as the Metabolic Derivatives An individual concerned about risk for Alzheimer's disease or who has been diagnosed with early Alzheimer's disease is given a labeled precursor that is incorporated into newly synthesized proteins in the body. A 10% solution of $^{13}C_1$-glycine is given orally (100 mg/ml, in water) every 2 hours for a total of 3 doses (time zero, two and four hours; 30 ml doses, for total of 90 ml). A plasma (2 ml) sample is collected from the individual after a known time (e.g., 6 hours) of $^{13}C_1$-glycine intake. A urine aliquot (20 ml) is collected from the individual at a defined time point or points (e.g., day 3 after administration of the $^{13}C_1$-glycine). From the urine aliquot, total amyloid-beta (A-beta) peptides are immunoprecipitated, for example, using a monoclonal anti-A-beta antibody coupled to Sepharose beads (Senetek, Inc.), then eluted from the beads with isopropanol/water formic acid (4:4:1), plus cyano-4-hydroxycinnamic acid. The A-beta peptides are loaded onto matrix-assisted laser desorption (MALDI)/time-of-flight (TOF) mass spectrometer (1.5 microliter added). Mass isotopomers in the A-beta 1-40 envelope (e.g., m/z 4,327-4,335) and A-beta 1-42 (e.g., m/z 4,511-4,519) are monitored.

Relative abundances of the above mass isotopomers are quantified in the sample and compared to values from unlabeled standards to calculate the proportion of labeled molecules present in the sample.

By one such calculation method, the proportion of excess labeled A-beta molecules is calculated by subtraction of unlabeled standards from labeled samples (e.g., sum of m/z 4,327-4,335=0.0040 above the value in standards of A-beta 1-40 and the um of m/z 4.511-4.519 is 0.0030 above this value in standards of A-beta 1-42). Free glycine is isolated from the plasma sample using an SPE column and converted to the butyl ester-acetamide derivative, e.g. by using butanolic HCl followed by acetic anhydride. The derivatized glycine is injected into a gas chromatograph/mass spectrometer (e.g., HP Model 5973) using a DB-225 column and conditions. The mass spectrum of the glycine peak is collected, monitoring masses m/z 174 and 175, and quantifying their relative abundances compared to unlabeled standards (e.g., m/z 175/(174+175)=0.4349 in sample and 0.0872 in standard). The proportion of labeled:unlabeled glycine molecules present is calculated, to establish the maximal possible label incorporation into brain APP during the period of $^{13}C_1$-glycine intake (e.g., 40%).

The ratio of the labeled proportion of A-beta 1-40 or A-beta 1-42 molecules is then compared to the labeled proportions of free glycine molecules, by one calculation method, correcting for the number of glycine subunits in A-beta 1-40 or A-beta 1-42; these ratios represent the fraction of brain APP converted to A-beta 1-40 and A-beta 1-42 that were newly synthesized during the $^{13}C_1$-glycine labeling period; any differences between A-beta 1-40 and A-beta 1-42 represent differences in biosynthesis of brain APP destined for A-beta 1-40 and A-beta 1-42, respectively.

The biosynthesis rate of APP in the brain of the individual during the period of $^{13}C_1$-glycine administration is calculated by MIDA, (e.g., 1.0% biosynthesis/6 hour, or 4.0% per day, or a residence time of 25 days (1.0/0.04) for brain APP in the individual).

The same procedure is repeated in the individual after an experimental intervention (e.g., secretase inhibitor; estrogen treatment), to determine the effects of the treatment on brain total APP biosynthesis and turnover, as one example, or on partitioning between A-beta 1-40 and A 1-42, as another example, as an index of efficacy of the intervention, or after a potential change in disease activity (e.g., subjective change in mental status) as an index of progression of underlying Alzheimer's risk or disease activity.

Alternatively, said individual is given $^2H_2O$ (70%, 50 ml twice a day by mouth) for 14 days. A plasma, saliva or urine sample is taken from the subject at days 7 and 14 of $^2H_2O$ intake. A urine aliquot is collected from the individual at day 14. From the urine aliquot, total A-beta peptides or A-beta 1-40 and A-beta 1-42 peptides are isolated by immunoprecipitation, as described above. The A-beta peptides are then subjected to acid hydrolysis (HCl 100° C., 60 min.) to release free amino acids. The amino acids are derivatized for GC/MS analysis.

By one such method, the N-acetyl-butyl-ester derivative of alanine is formed, using butanolic HCl followed by acetic anhydride.

The derivatized amino acids are injected into a GC/MS (e.g. HP 5973 instrument) using a DB-225 column. The mass spectrum of the alanine and glycine peaks are collected. Relative abundances of m/z 188–190 are measured in alanine in samples and unlabeled standards (e.g. alanine m/z 188/(m/z 188+189+190)=0.1025 in samples and 0.0950 in standards). The proportion of labeled:unlabeled alanine molecules present in the sample is then calculated.

By one such method, the proportion of excess labeled alanine molecules in the sample is calculated by subtraction of the relative abundance of $M_{+1}$ alanine in unlabeled standards from labeled samples (e.g. 0.1025–0.0950=0.0075, or 0.75% labeled $M_{+1}$ alanine molecules).

These relative abundances are compared to calculated maximal possible abundances at the measured body $^2H_2O$ enrichment present (e.g. in body $^2H_2O$ enrichment=1.0%, alanine excess $M_{+1}$ abundance=3.1%). The fractional synthesis rate of the A-beta peptide isolated is calculated using standard precursor-product equations known in the art (e.g. measured alanine excess $M_{+1}$=0.75%, calculated maximal alanine excess $M_{+1}$=3.1%, ratio=0.75/3.1%=24% new A-beta synthesis over 14 days, or 1.96% replacement of brain A-beta from APP per day).

The above procedure is repeated in the individual after an experimental intervention, for example, as described above.

Example 4

Synovial Fluid and Cartilage Hyaluronan or Other Glycosaminoglycans or Proteoglycan Biosynthesis and Breakdown Rates Using Hyaluronic Disaccharide Polymers and Chondrottin-Sulfate Polymers as the Metabolic Derivative An individual with established or suspected rheumatoid arthritis (RA) or osteoarthritis (OA) or at risk for RA or OA is given a labeled precursor that is incorporated into a glycosaminoglycan or proteoglycan in the synovial joint fluid or cartilage (such as hyaluronan, chondroitin sulfate, heparan-sulfate or others). Examples of labeled precursors include $^2H_2O$ (incorporated into the N-acetyl-glucosamine and glucuronic acid moieties of hyaluronan; into the N-acetyl-galactosamine-sulfate and glucuronic acid moieties of chondroitin-sulfate, or the N-acetyl-glucosamine-sulfate and glucuronic acid-sulfate moieties of heparan-sulfate); $^2H$- or $^{13}C$-glucose (incorporated into the N-acetyl-galactosamine and N-acetyl-glucosamine moieties of these glycosaminoglycans and proteoglycans); $^{13}C$-acetate (incorporated into the acetyl-moieties of N-acetyl-galactosamine or N-acetyl-glucosamine); and $^{15}N$-glycine (incorporated into the nitrogen component of N-acetyl-galactosamine or N-acetyl-glucosamine). A blood or urine aliquot is collected from the individual. High performance-liquid-chromatography (HPLC) is performed to isolate polymers of hyaluronic acid-disaccharide ($HA_n$), polymers of chondroitin-sulfate-disaccharide ($CS_n$) and/or polymers of other glycosaminoglycan disaccharides, such as the polymer of heparan-sulfate-disaccharide ($HS_n$), using HPLC procedures understood in the art. Alternatively, the polymers of these glycosaminoglycan-disaccharides can be converted to their free disaccharide units (e.g. by incubation of the sample with hyaluronidase). The glycosaminoglycan disaccharide polymers or free disaccharide units are then derivatized, to allow one of its components to be analyzed by GC/MS (by treating with methanolic HCL [100° C.] followed by acetic anhydride:pyridine, to produce the methyl, triacetyl, N-acetylglucosamine derivative from $HA_n$ or HA, for example).

Figure 9A:
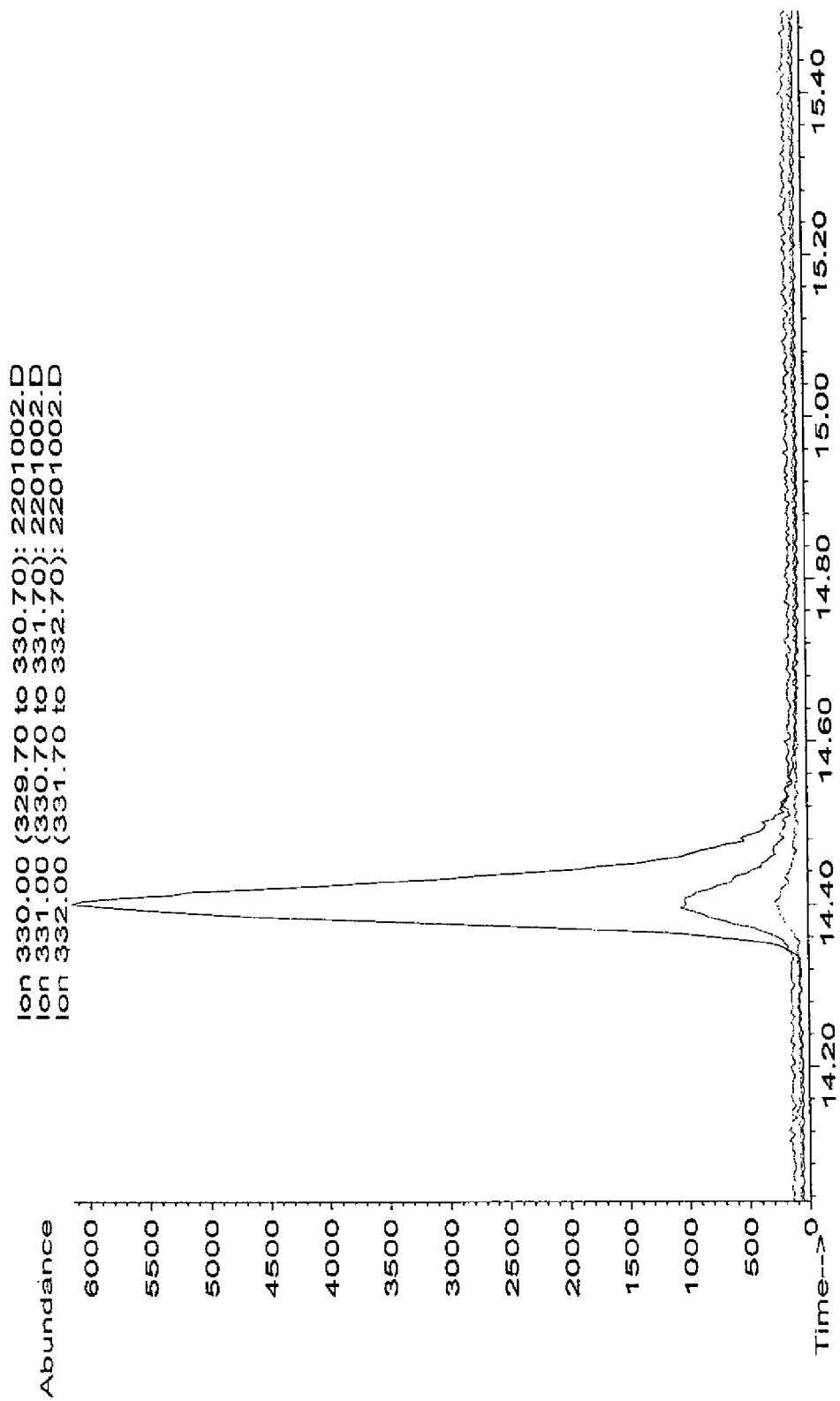
FIGS. 9A and 9B depict a gas chromatograph and mass spectrum of methyl, triacetyl acetate, N-acetyl glucosamine derivative of hyaluronic acid (HA).
Figure 9B:
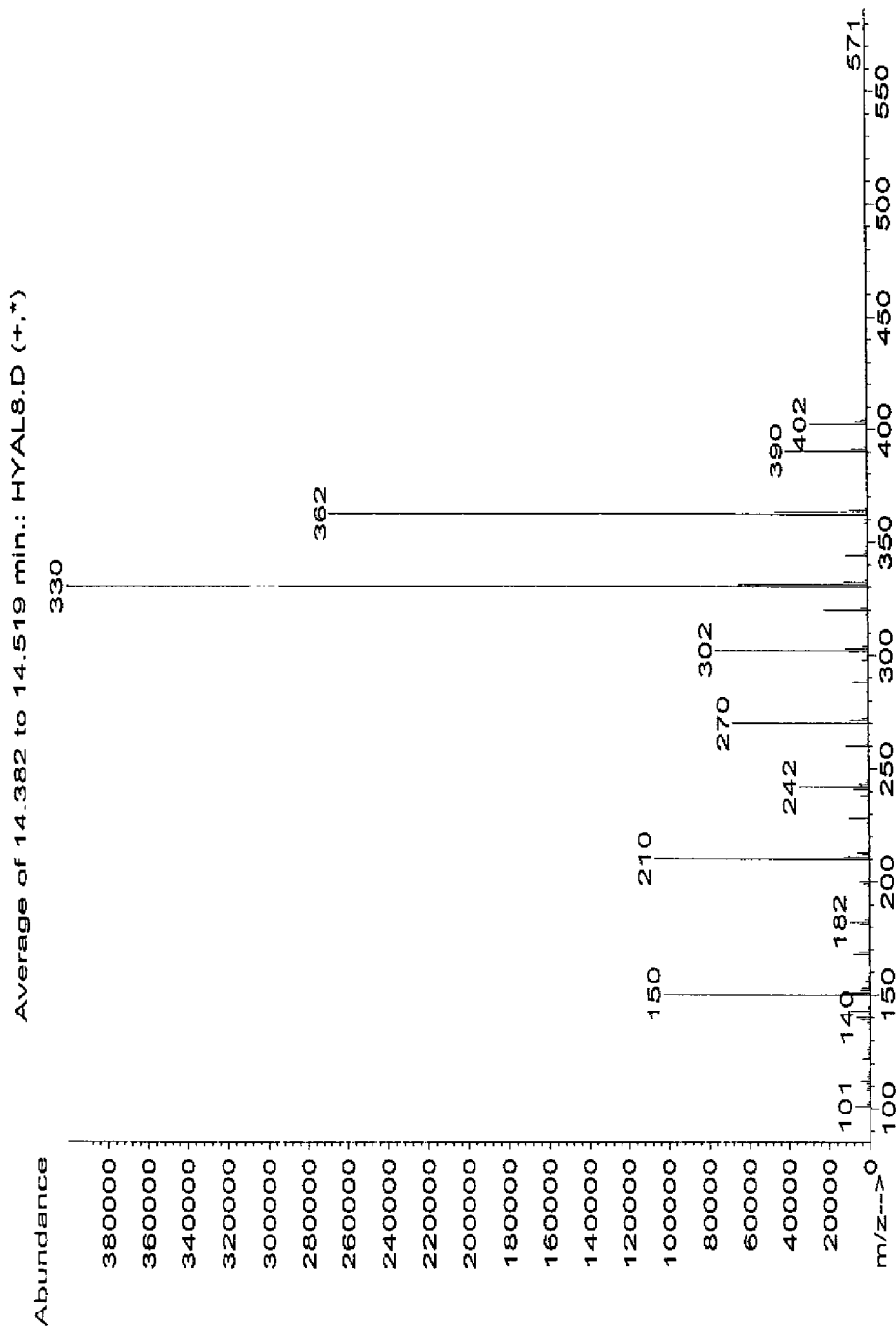

The isotopic enrichment of said derivatized component is then measured by GC/MS, such as selected ion monitoring of the appropriate masses. For example, the methyl, triacetyl, N-acetylglucosamine derivative is analyzed as m/z 331-333 (representing the $M_0$, $M_{+1}$ and $M_{+2}$ masses). Relative abundances of the above mass isotopomers are quantified in labeled samples and compared to unlabeled standards (e.g. 332/(331+332+333)=0.1370 in unlabeled standards). An example of one such mass spectrum is shown in FIG. 9.

The proportion of labeled to unlabeled molecules present in each sample is then calculated. By one such calculation method, the proportion of excess labeled methyl-triacetyl-N-acetyl-glucosamine molecules in the sample is calculated by subtracting unlabeled standards from labeled samples (e.g. 0.1540 $M_{+1}$ in samples, 0.1370 $M_{+1}$ in standards, or 0.0170 $M_{+1}$=1.70% labeled $M_{+1}$ methyl-triacetyl-N-acetyl-glucosamine). The proportion of labeled N-acetyl glucosamine molecules present in tissue hyaluronan biosynthetic pool is calculated based on body $^2H_2O$ enrichments, using MIDA (e.g. 0.1710 $M_{+1}$ N-acetyl-glucosamine in tissue pools if body $^2H_2O$ enrichment is 1.0%, or 3.4% labeled $M_{+1}$ N-acetyl-glucosamine). The biosynthesis and breakdown rates of synovial fluid or hyaline cartilage hyaluronan are then calculated by comparison of the proportion of labeled N-acetyl-glucosamine molecules in the sample to the proportion of labeled molecules in tissue N-acetylglucosamine pools (e.g. 1.70%/3.4%=50% newly synthesized HA molecules in synovial fluid and cartilage).

The rate of hyaluronan or other glycosaminoglycan biosynthesis and breakdown in synovial fluid and cartilage reflects the replacement and destruction rates of joint glycosaminoglycans and can be used as a measure of disease activity and/or therapeutic efficacy in RA or OA, particularly for assessment of joint protective anti-rheumatic agents.

The above procedure and calculations may be repeated after an intervention intended to stimulate production of hyaluronan, chondroitin-sulfate or other synovial glycosaminoglycans (such as glucosamine-sulfate) and to slow the progression of RA or OA, as an index of efficacy of the intervention, or after an apparent change in disease activity (e.g. a new set of symptoms), as an index of or test for disease activity or progression.

Example 5

Muscle Myosin Biosynthesis Using Urinary 3-Methyl-Histidine as the Metabolic Derivative An individual undergoing a physical training program or medical therapeutic regimen intended to increase muscle mass by increasing muscle myosin biosynthesis (e.g., an athlete; an elderly person receiving physical therapy after a stroke; a patient with cachexia related to cancer or AIDS who is receiving nutritional or anabolic agent therapy) is given a labeled precursor that is incorporated into the body's proteins during biosynthesis. Examples of labeled precursors include $^{15}N$-histidine (50 mg/ml in water), given orally every 2 hours for 4 doses (10 ml/dose). A urine aliquot (10 ml) is collected from the individual at a defined time point or points (e.g., at the conclusion of the $^{15}N$-histidine or 3-$^{13}C$ serine administration protocol and again at day 3 after administration of the $^{15}N$-histidine. In an alternative embodiment, $^2H_2O$ is given (50 ml of 70% $^2H_2O$) twice a day for 7 days. Total urinary amino acids are isolated with an SPE column. The amino acids are derivatized for gas chromatographic/mass spectrometric analysis.

By one such method, the amino acids are converted to the butyl-ester acetamide derivative, using butanolic HCl followed by acetic anhydride.

The derivatized amino acids are injected into a gas chromatograph/mass spectrometer (e.g., HP 5973 instrument), using, e.g., a DB-225 column. The mass spectrum of the 3-methyl histidine peak is collected while monitoring mass isotopomers at m/z 267 and 268 (parent and M+1 ions, respectively). Relative abundances of the above mass isotopomers are quantified in samples and compared to unlabeled standards (e.g., m/z 267/[m/z 267+268]=0.1200 in samples and 0.0960 in standards). The proportion of labeled:unlabeled molecules present in the sample is calculated for 3-methylhistidine using MIDA.

By one such calculation method, the proportion of excess labeled 3-methyl-histidine molecules in the sample is calculated by subtraction of unlabeled standards from labeled samples (e.g., 0.0240, or 2.4%). The mass spectrum of the derivatized-histidine or serine peaks (from the timepoint collected at the conclusion of the isotope administration protocol) are collected while monitoring mass isotopomers at 263 and 264 (parent and M+1 ions, respectively) for histidine or mass isotopomers at 246 and 247 (parent and M+1 ions, respectively) for serine. The relative abundances of the above mass isotopomers in samples are quantified and compared to unlabeled standards (e.g., m/z 264/(263+264)=0.4450 in samples and 0.0950 in standards, for histidine). The ratio of labeled to unlabeled molecules is calculated for histidine or serine (e.g., 0.3500, or 35%).

From the proportion of labeled 3-methylhistidine molecules present compared to the proportion of labeled free histidine or free serine molecules present, the biosynthesis rate of new muscle myosin in the individual during the 8 hour period of $^2H_5$-histidine administration is calculated, using standard precursor-product equations (e.g., 0.0240/0.3500=6.8%).

The above procedure is repeated periodically, to establish the efficacy of the individual's athletic training program or medical therapeutic program intended to increase muscle myosin biosynthesis.

Figure 8A:
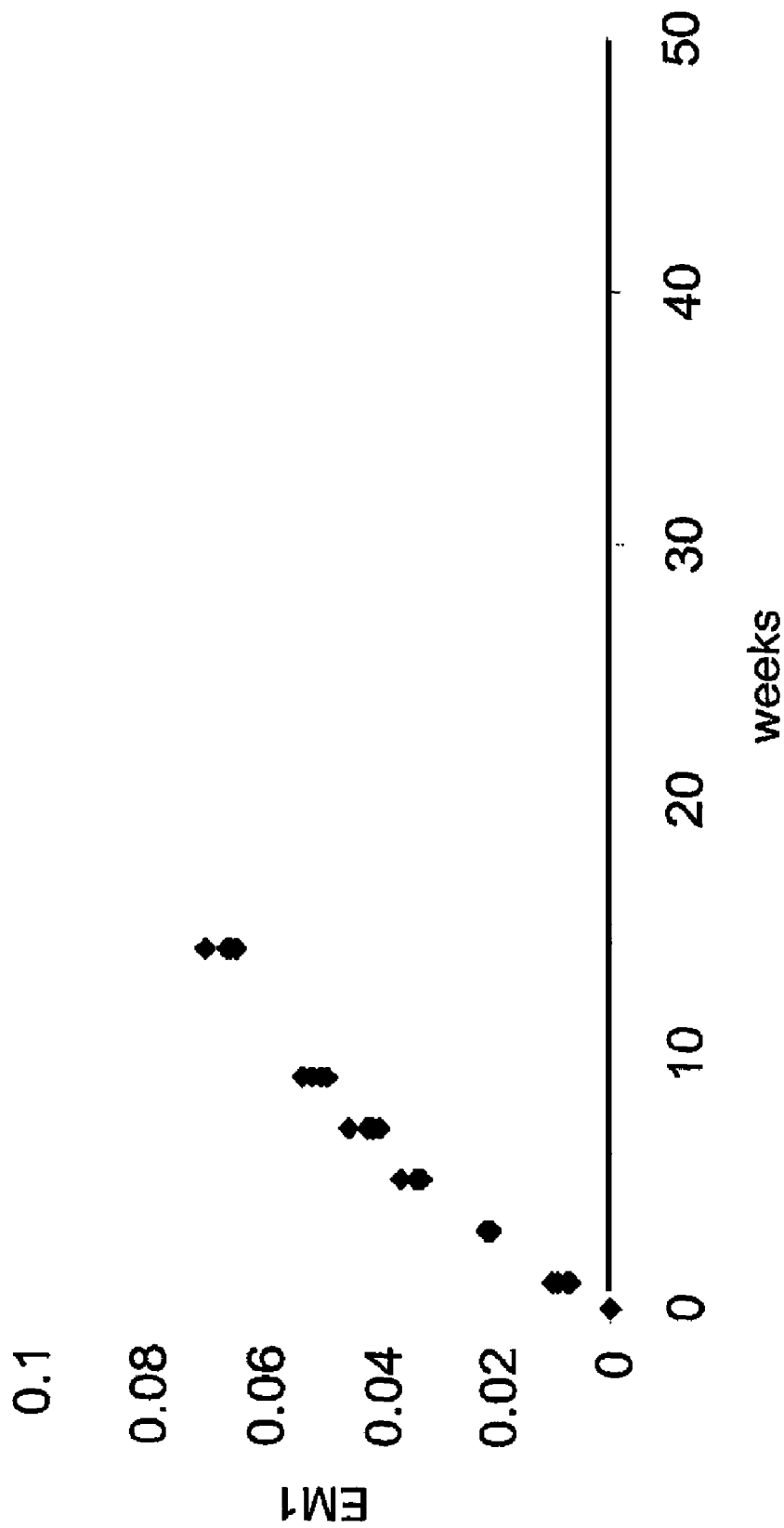
FIG. 8A depicts the course of $^2H$ incorporation from $^2H_2O$ into galactose moiety of brain galactosyl cerebroside in mice maintained on 8% $^2H_2O$ as drinking water. Each time point represents five mice. EM1 is the excess abundance of M+1 mass isotopomer in methyl tetraacetyl galactose.
Figure 8B:
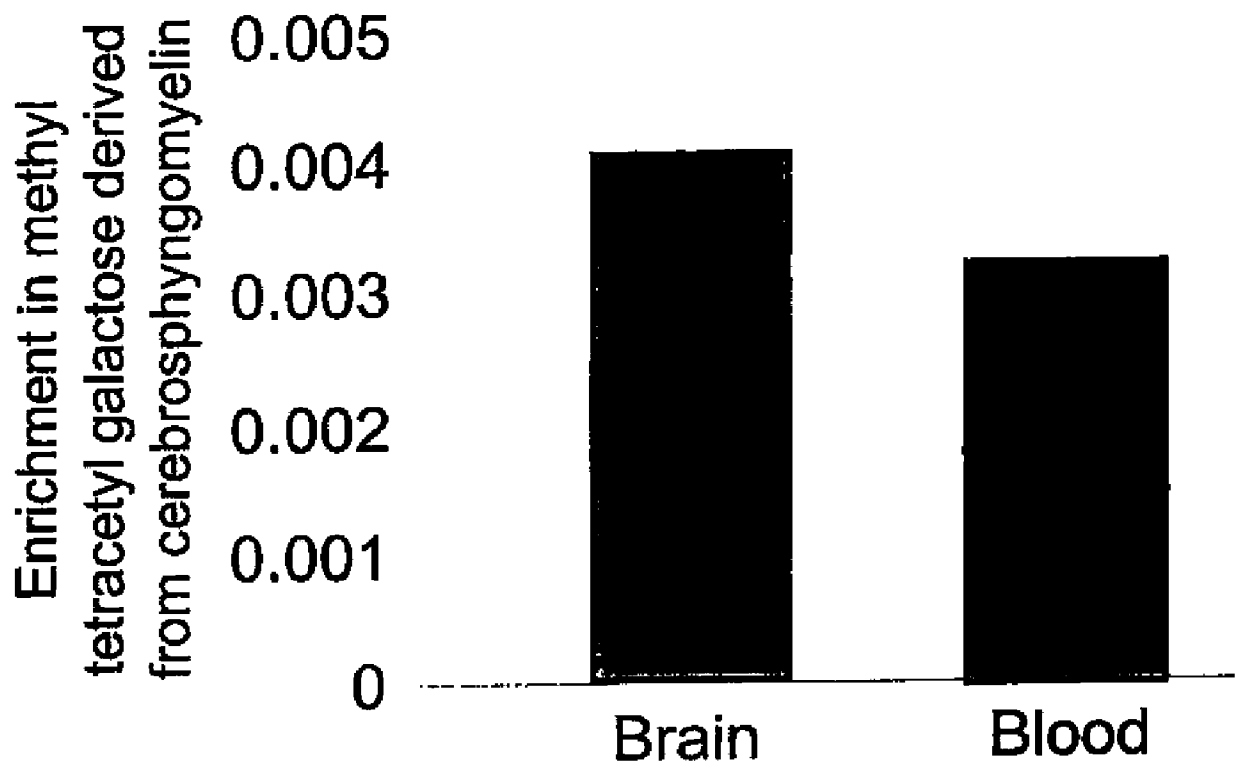

An example of this procedure in human subjects is shown in FIG. 8, which demonstrates that metabolic derivative in blood may be used to reflect label incorporation in molecule in brain. Table 3 shows the incorporation of $^2H$ from $^2H_2O$ into urinary 3-methyl-histidine in human subjects during intake of $^2H_2O$ for 4-8 weeks. The data suggest a half-life of roughly 3 weeks for muscle myosin in these human subjects.

TABLE 3

Incorporation of $^2H$ from $^2H_2O$ into urinary 3-methyl-histidine in human subjects during intake of $^2H_2O$ for 4-8 weeks.

| EM1 | $^2H_2O$ (%) | $A_1^\infty$ | f (%) | k (d$^{-1}$) |
|---|---|---|---|---|
| 2.6 ±1.5 | 1.8 ±0.3 | 3.3 ±0.5 | 78 | 0.037 |

EM1: excess M + 1 mass isotopomer in t-butyl dimethyl silyl derivative of 3-methyl histidine;
$^2H_2O$ (%): body water enrichment;
$A_1^\infty$: calculated maximal EM1 of 3-methyl histidine at measured $^2H_2O$;
f (%): fractional synthesis;
k: replacement rate constant of 3-methyl-histidine.

Example 6

Whole-Body Cell Division (DNA Biosynthesis) Using Methyldeoxycytosine as the Metabolic Derivative A human individual at risk for cancer or other disorder related to cell proliferation is given a labeled precursor that is incorporated into newly synthesized DNA in the body. $^2H_2O$ is given orally (70% $^2H_2O$ as drinking water, 80 ml once a day for 14 days). A urine aliquot (<10 ml) is collected from the individual at a defined time point (e.g., at the completion of the 14-day $^2H_2O$ administration period). Total urinary nucleosides are isolated with an SPE column, then the fractions enriched with deoxycytosine and methyl-deoxycytosine are eluted with a water wash. The isolated nucleosides including methyldeoxycytosine are derivatized for gas chromatographic/mass spectrometric analysis, according to methods known calculation methods. By one such method, the trimethylsilyl (TMS) derivative of methyldeoxycytosine and other nucleosides present is formed with bis(trimethyl[silyl]) acetamide. The TMS methyl-deoxycytosine is injected into a gas chromatograph/mass spectrometer (e.g., HP model 5973), with a DB-17 column.

The mass spectrum of the methyldeoxycytosine peak is collected monitoring mass isotopomers at m/z 457-459 (parent, M+1 and M+2 ions). Relative abundances of the above mass isotopomers are quantified in samples and compared to unlabeled standards (e.g., 0.0950 M+1 in samples, 0.0820 M+1 in unlabeled standards). The proportion of labeled:unlabeled molecules present in the sample is calculated for methyldeoxycytosine.

By one such calculation method, the proportion of excess labeled methyldeoxycytosine molecules in the sample is calculated by subtraction of unlabeled standards from labeled samples (e.g., 0.0130 or 1.3% labeled methyldeoxycytosine).

From the proportion of labeled methyldeoxycytosine molecules present, the biosynthesis of total body DNA during the 14 day $^2H_2O$ labeling period is calculated using standard precursor-product equations and estimates or direct measurements of the maximal deoxycytosine enrichment at these $^2H_2O$ administration rates (e.g., 15% new DNA/14 days, or biosynthesis rate of ca. 1.1% per day).

The above procedure is repeated after an intervention intended to reduce cell proliferation (DNA biosynthesis) throughout the body, such as caloric restriction, vitamin D administration, or cell-cycle inhibitory drugs, and thereby reduce general cancer risk in the individual.

Example 7

Brain Membrane Lipid Biosynthesis (Brain Growth and Development) Using 24(S)-Hydroxycholesterol in Plasma as the Metabolic Derivative A human individual is given a labeled precursor that is incorporated into newly synthesized lipids in the body. $^2H_2O$ is administered orally for a defined period of time (e.g., 70% $^2H_2O$ as drinking water, 80 ml once a day, for 7 days). A blood aliquot is collected from the individual at a defined time point. 24(S)-hydroxycholesterol, a catabolite of tissue cholesterol that is uniquely synthesized from cholesterol in brain and escapes into the bloodstream, is extracted from blood, and derivatized for gas chromatographic/mass spectrometric measurement.

The isotopic enrichment of $^2H$-24(S)-hydroxycholesterol is determined by MIDA, from the ion abundances at m/z 458, 459 and 460 in samples compared to unlabeled standards (e.g., 0.1000 in sample, 0.0900 in unlabeled standards). The proportion of labeled to unlabeled molecules of 24(S)-hydroxycholesterol present in the sample is calculated.

By one such calculation method, the proportion of excess labeled 24(S)-hydroxycholesterol molecules in the sample is calculated by subtraction of unlabeled standards from labeled samples (e.g., 0.0100 or 1%). The isotopic enrichment of body water is determined by MIDA (e.g., 1.5%).

The biosynthesis rate of brain cholesterol, and thus brain myelin (ratio of 2:1, cholesterol:ceramide, in myelin), is determined by application of the precursor-product relationship from labeled hydrogen in body water to labeled hydrogen in newly synthesized cholesterol (e.g., 2.1% new 24(S)-hydroxycholesterol over 7 days, or biosynthesis rate of brain cell membranes of 0.3% per day, for a doubling-time or half-life of 231 days).

The above procedure is repeated after an intervention intended to stimulate brain growth and/or development (e.g., a dietary intervention, educational program or other stimulatory activity in children, pharmacologic therapy), to establish efficacy of the intervention.

Example 8

Brain Myelin Biosynthesis and Breakdown Rates (Myelination, Demyelination and Remyelination) Using Plasma Galactosyl-Cerebroside as the Metabolic Derivative A human individual with a known or suspected demyelinating disorder, such as multiple sclerosis, is given a labeled precursor that is incorporated into a lipid moiety that is exclusively or nearly exclusively present in the brain myelin sheath (such as galactosyl-cerebroside) and that is released into the bloodstream or cerebrospinal fluid after breakdown of brain myelin. Such labeled precursors include $^2H_2O$ (incorporated into the galactose, sphingosine and fatty acid moieties of galactosyl-cerebrosides in the myelin sheath), $^2H$-glucose or $^{13}C$-glucose (incorporated into the galactose moiety of galactosyl-cerebroside), $^{13}C$-serine (incorporated into the sphingosine moiety of cerebrosides) or $^{13}C$-fatty acids (incorporated into the fatty acyl-moiety of galactosyl-cerebrosides). A blood or urine aliquot is collected from the individual. Lipids are extracted from the blood or urine sample, for example, by Folch extraction. Galactosyl-cerebroside- or another characteristic lipid components of the myelin sheath is then separated from the lipid extract, such as thin layer chromatography. The galactosyl-cerebroside is then derivatized to allow one of its components to be analyzed by gas chromatography/mass spectrometry (GC/MS), such as methanolic HCl followed by acetic anhydride-pyridine to produce methyl, triacetyl-galactose, or methanolic HCl to produce fatty acid-methyl ester, to produce derivatives of sphingosine.

The isotopic enrichment of the labeled component of galactosyl-cerebroside analyzed (e.g. the derivatized galactose, fatty acid or sphingosine) is then measured by selected ion monitoring of the appropriate masses. In the example of an individual given $^2H_2O$ for 4 weeks and where the galactose moiety of galactocerebroside from plasma is analyzed, as m/z 331, 332 and 333 of methyl-tetracetyl-galactose, representing parent, $M_{+1}$ and $M_{+2}$ ions, is measured by selected ion monitoring during GC/MS analysis of samples and unlabeled standards. Relative abundances of the above mass isotopomers are quantified in samples and compared to unlabeled standards (e.g. 0.1450 $M_{+1}$ in samples, 0.1350 $M_{+1}$ in unlabeled standards). The proportion of labeled to unlabeled molecules present in each sample is then calculated. By one such calculation method, the proportion of excess labeled methyl, triacetyl-galactose molecules in the sample is calculated by subtraction of unlabeled standards from labeled samples (e.g. 0.0100 or 1.00% labeled $M_{+1}$ methyl-tetracetyl-galactose in the above example). The proportion of labeled galactose molecules present in tissue galactosyl-cerebroside biosynthetic pools is calculated based on body $^2H_2O$ enrichments, using MIDA (e.g. 0.1680 $M_{+1}$ in tissue pools if body water $^2H_2O$ enrichment is 1.0%, or 3.3% labeled $M_{+1}$). The biosynthesis and breakdown rates of brain myelin-sheath lipids are then calculated by comparison of the proportion of labeled galactose molecules in the sample to the proportion of labeled galactose molecules in tissue galactosyl-cerebroside biosynthetic pools (e.g. 1.00%/3.3%=30% newly synthesized galactosyl-cerebroside in brain myelin over the period of $^2H_2O$ intake by the subject). The rate of galactosyl-cerebroside biosynthesis and breakdown reflects the rate of myelination, demyelination and remyelination in brain and may be used as a measure of disease activity and/or therapeutic efficacy in multiple sclerosis or other clinical demyelinating conditions.

The above procedure and calculations may be repeated after an intervention intended to stimulate remyelination or reduce demyelination and slow the progression of multiple sclerosis, as an index of efficacy of the intervention, or after an apparent change in disease activity (e.g. a set of new symptoms), as an index of or test for disease activity or progression.

An example of this procedure is shown in FIG. 9, which demonstrates measurement of isotopic enrichment in HA through GC/MS procedures.

Example 9

Brain Myelin Biosynthesis and Breakdown (Myelination, Demyelination, and Remyelination), from Myelin Basic Protein Like Material (MBPLM) in Urine as the Metabolic Derivative A human individual with a known or suspected demyelinating disorder, such as multiple sclerosis, is given a labeled precursor that is incorporated into newly synthesized proteins in the body (e.g. $^2H_2O$ or a labeled amino acid such as $^{13}C$-leucine) for a defined period of time, such as 4 weeks. A blood aliquot is collected from the individual. Myelin basic protein like material (MBPLM) is isolated from blood by use of a specific antibody, for example, by using an immunoaffinity column. The MBPLM is hydrolyzed to free amino acids, using acid conditions or protease enzymes. The free amino acids are derivatized for analysis by gas chromatography/mass spectrometry.

The isotopic enrichment of the labeled amino acid(s) isolated from MBPLM is measured by selected ion monitoring on the appropriate masses (e.g., m/z 231, 232 and 233 for n-butyl-ester-acetamide of leucine, if $^{13}C_1$-leucine was administered to the subject or m/z 188-190 for the N-acetyl-butyl ester derivative of alanine, if $^2H_2O$ was administered to the subject) in samples and unlabeled standards.

The proportion of labeled to unlabeled leucine or alanine molecules present in the sample is calculated.

By one such calculation method, the proportion of excess labeled alanine molecules in the sample is calculated by subtraction of the relative abundance of $M_{+1}$ alanine in unlabeled standards from labeled samples (e.g. $M_{+1}$ alanine in unlabeled standards is 0.0950, $M_{+1}$ alanine in labeled samples is 0.1050, so the proportion of labeled alanine molecules in the sample is 0.0100 or 1.0%). The proportion of labeled alanine present in tissue protein biosynthetic pools is then established, based on the $^2H_2O$ enrichment of body water (e.g. 3.1% $M_{+1}$ alanine, or 0.1260 $M_{+1}$ alanine in tissue pools, if body water $^2H_2O$ enrichment is 1.0%). The biosynthesis and breakdown rates of brain MBPLM are then determined by comparison of the proportion of labeled alanine molecules present in the MBPLM to the proportion of labeled alanine present in tissue protein biosynthetic pools (e.g. 1.0%/3.1%=33% biosynthesis of MBPLM over 4 weeks), by application of the precursor-product relationship or other equations known in the art.

The rate of MBPLM biosynthesis and/or breakdown reflects the rate of myelination, demyelination and remyelination and may be used as a measure of disease activity, and/or therapeutic efficacy, in multiple sclerosis or other clinical demyelinating conditions.

The above procedure and calculations may be repeated after an intervention intended to stimulate remyelination or reduce demyelination and slow the progression of multiple sclerosis, as an index of efficacy of the intervention, or after a potential change in disease activity (e.g., new symptoms of uncertain cause), as an index of or test for disease activity or progression.

Example 10

Tissue Collagen Biosynthesis from the Rate of Dilution of Label in Pyridinoline/Deoxypyridinoline after Discontinuing Label Administration The same procedure as described above (see examples 1 or 2), for tissue collagen biosynthesis using pyridinoline/deoxypyridinoline (HP/DP), is followed (through calculation of the proportion of labeled:unlabeled HP and DP molecules present, at a defined time (e.g., time zero) after administration of $^{13}C_1$-lysine or other labeled precursor for tissue collagen biosynthesis). A urinary aliquot or a plurality of urinary aliquots (10 ml) are collected subsequently, at a defined timepoint or points after time zero (e.g., every 2 weeks for 2 months in one embodiment).

The same analytic procedure is followed as for the original urinary sample (see examples 1 or 2), to calculate the proportion of labeled:unlabeled HP and DP molecules present at each time point. From the dilution rate (i.e., the rate of decrease in the proportion of labeled DP/HP molecules present), the biosynthesis rate (k) of tissue collagen is calculated, using the standard isotope dilution equation using the formula:

$$A_t = A_0 \cdot e^{-kt},$$

where $A_t$=proportion of labeled DP/HP in sample at time t
$A_0$=proportion of labeled DP/HP in sample at time zero
t=time
k=rate constant for tissue collagen biosynthesis $$k = \frac{-\ln\left(\frac{A_t}{A_0}\right)}{t},$$

The same procedure is repeated in the individual after a therapeutic intervention intended to alter the biosynthesis rate of bone collagen or other tissue collagens is performed, as an index of efficacy of the intervention.

It is understood that the examples and embodiments described herein are for illustrative purposes only and that various modifications or changes in light thereof will be suggested to persons skilled in the art and are to be included within the spirit and purview of this application. All publications, patents and patent applications cited herein are hereby incorporated by reference in their entirety for all purposes to the same extent as if each individual publication, patent or patent application were specifically and individually indicated to be so incorporated by reference.

---

What is claimed is:

1. A method for determining the rate of biosynthesis of a biological molecule in an individual through the detection of a metabolic derivative of the biological molecule, the method comprising the steps of:
   a) administering a precursor molecule comprising an isotope label to the individual for a period of time sufficient for the isotope label to become incorporated into the biological molecule and for the biological molecule to be metabolized, in vivo, into the metabolic derivative, wherein at least a portion of the metabolic derivative comprises the isotope label;
   b) obtaining a biological sample from the individual, wherein the biological sample comprises the metabolic derivative; and
   c) detecting the incorporation of the isotope label in the metabolic derivative of the biological sample;
   d) calculating the abundance of one or more mass isotopomers of the metabolic derivative by mass isotopomer analysis; and
   e) applying a precursor-product equation to determine the rate of biosynthesis of the biological molecule based on the abundance of one or mass isotopomers of the metabolic derivative,
   wherein the biological molecule is selected from the group consisting of proteins, polynucleotides, lipids, glycosaminoglycans, proteoglycans, and carbohydrates.

2. The method according to claim 1 wherein the metabolic derivative is a polymer comprising two or more subunits and wherein the determination of step e) employs mass isotopomer distribution analysis (MIDA).

3. The method according to claim 1 wherein the isotope label is selected from the group consisting of $^2H$, $^3H$, $^{13}C$, $^{15}N$, $^{18}O$, $^3H$, $^{14}C$, $^{35}S$, $^{32}P$, $^{125}I$, and $^{131}I$.

4. The method of claim 3 wherein the label is $^2H$.

5. The method of claim 1 wherein the precursor molecule is water.

6. The method according to claim 1 comprising the additional step of partially purifying the metabolic derivative of the biological sample before said step c).

7. The method according to claim 1 wherein the precursor molecule is administered orally.

8. The method according to claim 1 wherein following step b), the method includes the additional step of degrading the metabolic derivative of the biological sample to form a degraded metabolic derivative.

9. The method according to claim 8 wherein the degraded metabolic derivative is further separated by gas chromatography or HPLC.

10. The method according to claim 1 wherein the individual is a human.

11. The method of claim 1 wherein the metabolic derivative is a product of in vivo catabolism of the biological molecule.

12. The method according to claim 1 wherein the biological molecule is a protein.

13. The method according to claim 12 wherein the precursor molecule is an amino acid or a metabolic precursor of an amino acid.

14. The method according to claim 12 wherein the metabolic derivative is a peptide or polypeptide.

15. The method according to claim 12 wherein the protein is collagen.

16. The method according to claim 15 wherein the metabolic derivative is a collagen-specific metabolic derivative selected from the group consisting of N-terminal telopeptide α1(I) (SEQ ID NO: 1), N-terminal telopeptide α2(I) (SEQ ID NO: 2), N-terminal telopeptide α2(I) (SEQ ID NO: 3), N-terminal telopeptide α1(II) (SEQ ID NO: 4), N-terminal telopeptide α1(III) (SEQ ID NO: 5), C-terminal telopeptide α1(I) (SEQ ID NO: 6), C-terminal telopeptide α2(I) (SEQ ID NO: 7), C-terminal telopeptide α1(II) (SEQ ID NO: 8), C-terminal telopeptide α1(II) (SEQ ID NO: 9), C-terminal telopeptide α1(II) (SEQ ID NO: 10), C-terminal telopeptide β1(III) (SEQ ID NO: 11), cross-linked carboxy-terminal peptide of type I collagen (ICTP), PINP(α1) (SEQ ID NO: 12), PICP(α1) (SEQ ID NO: 13), PINP(α2) (SEQ ID NO: 14), PICP(α2) (SEQ ID NO: 15), PIINP(α1) (SEQ ID NO: 16), PIICP(α1) (SEQ ID NO: 17), PIIINP(α1) (SEQ ID NO: 18), PIIICP(α1) (SEQ ID NO: 19), PIVNP(α1) (SEQ ID NO: 20), PIVNP(α2) (SEQ ID NO: 21), PIVNP(α2) (SEQ ID NO: 22), PIVNP(α3) (SEQ ID NO: 23), PIVNP(α4) (SEQ ID NO: 24), PIVNP(α5) (SEQ ID NO: 25), and PIVNP(α6) (SEQ ID NO: 26).

17. The method of claim 16 wherein the metabolic derivative is an N-terminal or C-terminal amino acid sequence.

18. The method according to claim 12 wherein the protein is myosin.

19. The method according to claim 12 wherein the protein is Amyloid Precursor Protein (APP).

20. The method according to claim 19 wherein the metabolic derivative is amyloid-beta 1-40 or amyloid-beta 1-42.

21. The method according to claim 12 wherein the metabolic derivative is a post-translationally modified amino acid or protein.

22. The method according to claim 21 wherein the post-translationally modified amino acid or protein is selected from the group consisting of phosphoryllated, methylated, hydroxylated, glycosylated, N-acetyl-glucosaminated, prenylated, palmitoylated, and gamma-carboxylated amino acids or peptides.

23. The method according to claim 12 wherein the protein is myelin basic protein.

24. The method according to claim 23 wherein the protein is brain myelin basic protein.

25. The method according to claim 23 wherein the metabolic derivative is myelin basic protein-like material.

26. The method according to claim 1 wherein the biological molecule is a lipid.

27. The method according to claim 26 wherein the lipid is a brain membrane lipid.

28. The method of claim 26 wherein the metabolic derivative is selected from the group consisting of 24(s)-hydroxy-cholesterol, galactosyl-cerebroside, sphingomyelin, and sphingosines.

29. The method according to claim 1 wherein the biological molecule is a polynucleotide.

30. The method according to claim 29 wherein the polynucleotide is deoxyribonucleic acid (DNA).

31. The method according to claim 30 wherein the isotope label is incorporated in the DNA, post-replication.

32. The method according to claim 29 wherein said one or more metabolic derivatives is a nucleic acid.

33. The method according to claim 1 wherein the precursor molecule is administered repeatedly or continuously.

34. The method of claim 1 wherein the biological molecules is a glycosaminoglycan or a proteoglycan.

35. The method of claim 34, wherein the metabolic derivative is selected from the group consisting of hyaluronic acid disaccharide, hyaluronic acid polymers, N-acetyl glucosamine, N-acetyl-galactosamine, chondroitin-sulfate disaccharide, chondroitin-sulfate polymers, heparin sulfate disaccharide, and heparin sulfate disaccharide polymer.

36. The method of claim 1 wherein the biological sample is selected from the group consisting of urine, blood, saliva, lachrymal fluid, inflammatory exudates, synovial fluid, abscess, empyema or other infected fluid, cerebrospinal fluid, sweat, pulmonary secretions, sputum, seminal fluid and feces.

37. The method of claim 36 wherein the biological molecule is not present in quantities detectable by mass spectrometry in the biological sample.

38. A method for determining the rate of breakdown of a biological molecule in an individual through the detection of a metabolic derivative of the biological molecule, the method comprising the steps of:
 a) administering a precursor molecule comprising an isotope label to the individual for a period of time sufficient for the isotope label to become incorporated into the biological molecule and for the biological molecule to be metabolized, in vivo, into the metabolic derivative, wherein at least a portion of the metabolic derivative comprises the isotope label;
 b) discontinuing the administering step;
 c) obtaining a biological sample from the individual, wherein the biological sample comprises the metabolic derivative;
 d) detecting the incorporation of the isotope label in the metabolic derivative of the biological sample;
 e) calculating the abundance of one or more mass isotopomers of the metabolic derivative by mass isotopomer analysis; and
 f) applying an exponential decay equation to determine the rate of breakdown of the biological molecule based on the abundance of one or mass isotopomers of the metabolic derivative,
 wherein the biological molecule is selected from the group consisting of proteins, polynucleotides, lipids, glycosaminoglycans, proteoglycans, and carbohydrates.

39. The method according to claim 38 wherein the metabolic derivative is a polymer comprising two or more subunits and wherein the determination of step f) employs mass isotopomer distribution analysis (MIDA).

* * * * *